United States Patent [19]

Bodick et al.

[11] Patent Number: 4,945,476
[45] Date of Patent: Jul. 31, 1990

[54] INTERACTIVE SYSTEM AND METHOD FOR CREATING AND EDITING A KNOWLEDGE BASE FOR USE AS A COMPUTERIZED AID TO THE COGNITIVE PROCESS OF DIAGNOSIS

[75] Inventors: Neil Bodick, Philadelphia; Andre L. Marquis, Devon, both of Pa.

[73] Assignee: Elsevier Science Publishing Company, Inc., New York, N.Y.

[21] Appl. No.: 161,188

[22] Filed: Feb. 26, 1988

[51] Int. Cl.$^5$ .............................. G06F 15/42
[52] U.S. Cl. .................. 364/413.02; 364/413.13; 364/275.7; 364/282.1
[58] Field of Search .............. 364/513, 413.02, 413.13, 364/300, 200 MS File; 382/57, 6

[56] References Cited

U.S. PATENT DOCUMENTS

| | | | |
|---|---|---|---|
| 3,566,370 | 2/1971 | Worthington | 364/900 |
| 4,122,518 | 10/1978 | Castleman | 364/300 |
| 4,130,881 | 12/1978 | Haessler | 364/900 |
| 4,290,114 | 9/1981 | Sinay | 364/900 |
| 4,346,442 | 8/1982 | Musmanno | 364/408 |
| 4,347,568 | 8/1982 | Giguere | 364/300 |
| 4,422,105 | 12/1983 | Rodesch | 358/335 |
| 4,489,387 | 12/1984 | Lamb | 364/514 |
| 4,622,013 | 11/1986 | Cerchio | 434/118 |
| 4,658,370 | 4/1987 | Erman et al. | 364/900 X |
| 4,672,683 | 6/1987 | Matsueda | 364/521 X |
| 4,731,725 | 3/1988 | Suto et al. | 364/415 |
| 4,733,354 | 3/1988 | Potter et al. | 364/415 |

FOREIGN PATENT DOCUMENTS

| | | |
|---|---|---|
| 0044642 | 1/1982 | European Pat. Off. . |
| 0134976 | 3/1985 | European Pat. Off. . |
| 0182460 | 5/1986 | European Pat. Off. . |
| 8501412 | 5/1985 | Israel . |
| 83/02705 | 8/1983 | PCT Int'l Appl. . |
| 85/00717 | 2/1985 | PCT Int'l Appl. . |
| 1107826 | 3/1968 | United Kingdom . |
| 1456317 | 11/1976 | United Kingdom . |
| 1516285 | 7/1978 | United Kingdom . |
| 1528909 | 10/1978 | United Kingdom . |

OTHER PUBLICATIONS

Siegel et al., "Expert Systems: Application of Artificial Intelligence in Medicine", 9/86, pp. 175–181.
U.S. P.T.O. Caspir User's Guide, 9/86.

Primary Examiner—Jerry Smith
Assistant Examiner—Steven G. Kibby
Attorney, Agent, or Firm—Curtis, Morris & Safford

[57] ABSTRACT

A knowledge base having particular utility as a medical/pathology knowledge base contains textual and pictorial information on various diseases. The knowledge base includes user-selectable designations of diagnostic features which are characteristic of respective conditions to be diagnosed. These features comprise a case record and several case records are stored and retrieved for subsequent display of the features therein and of one or more pictorial images of those features. The pictorial images preferably are stored on a device such as an optical disk; and these pictorial images are linked to case records which may be stored in other storage devices, such as magnetic disk, whereby the retrieval of a case record accesses the linked pictorial images, whereby those pictorial images and features of the case record are displayed.

78 Claims, 92 Drawing Sheets

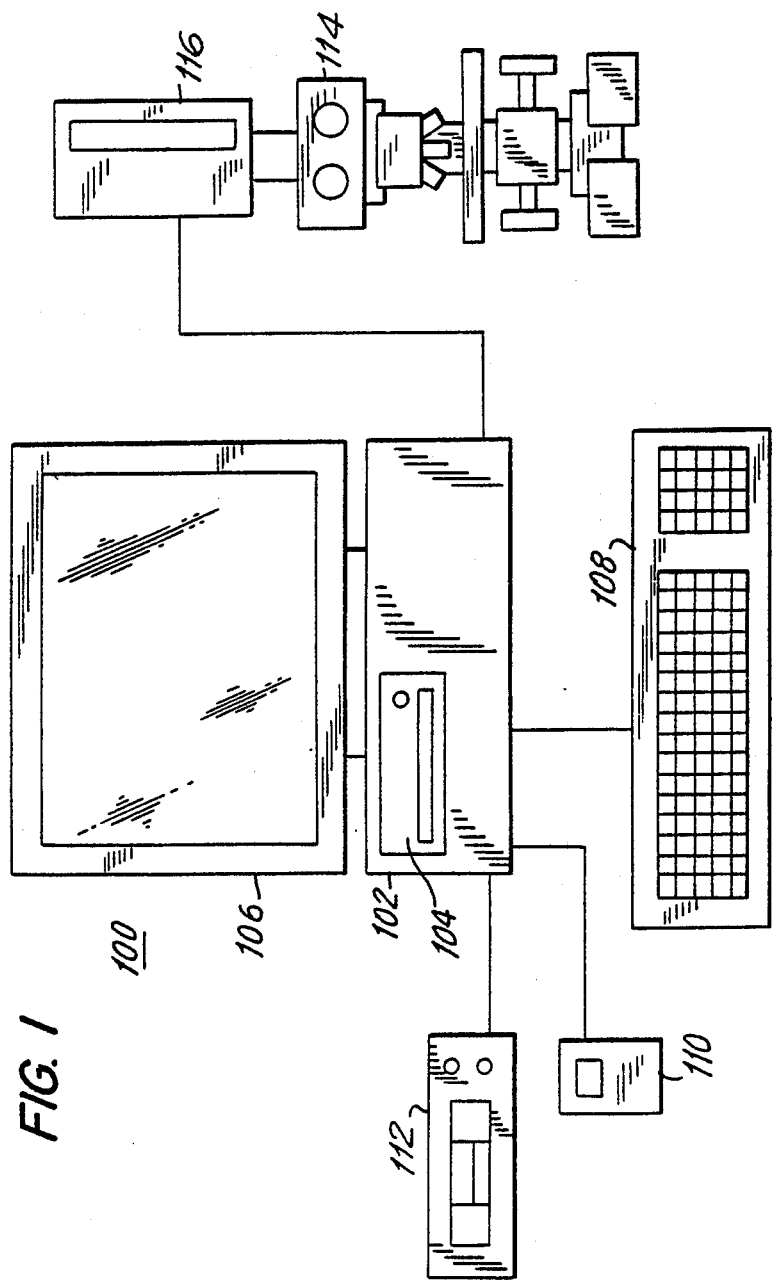

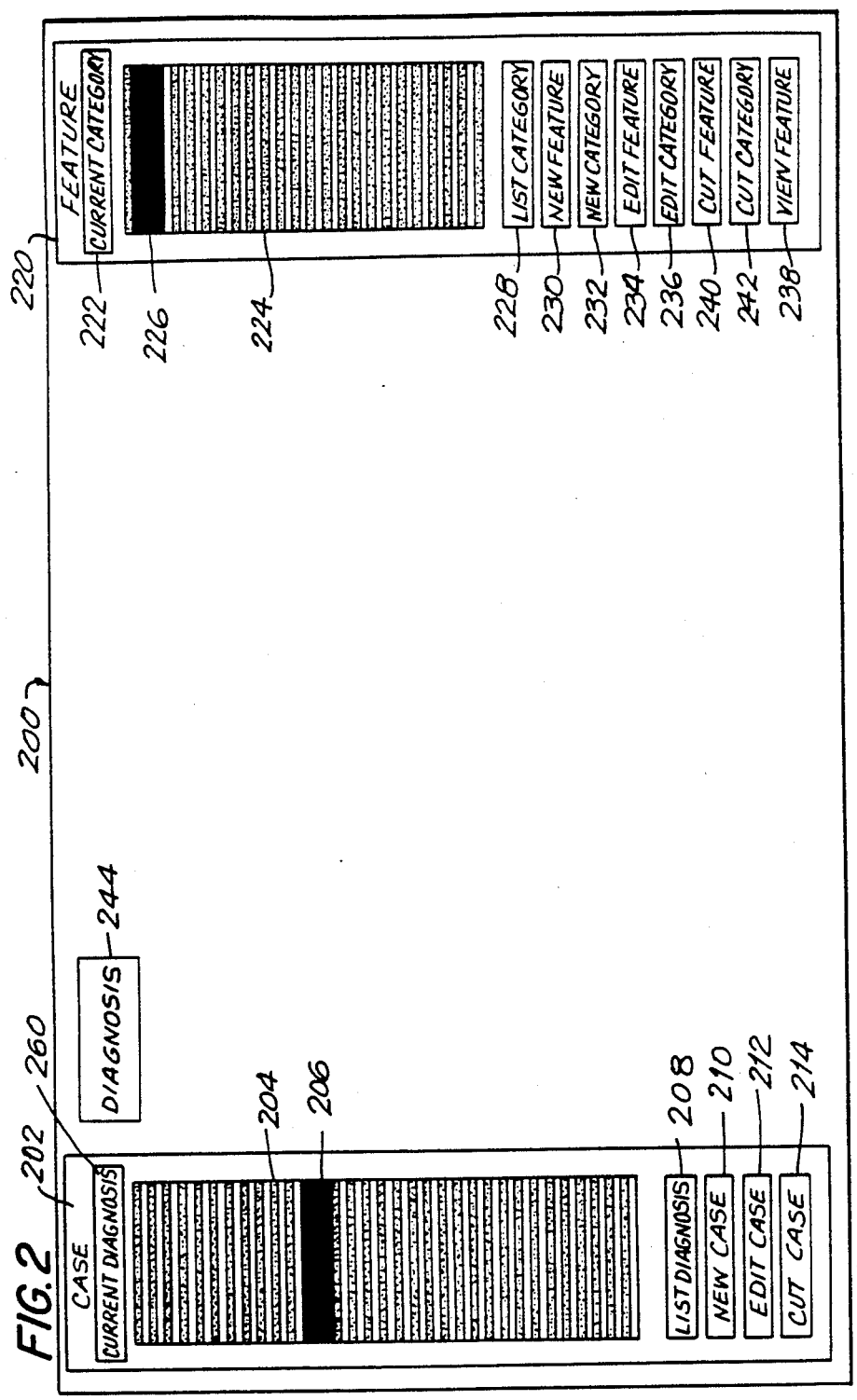

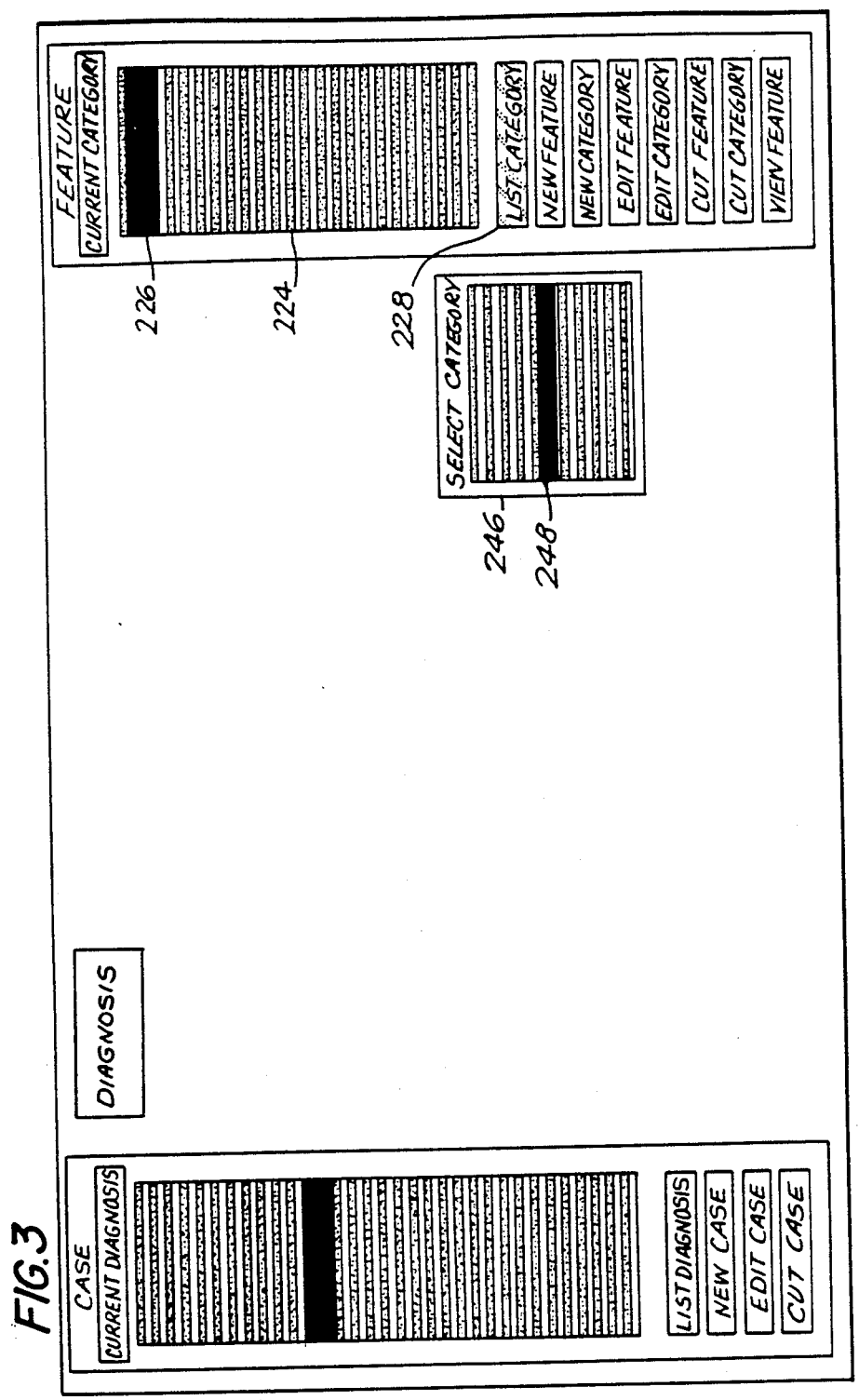

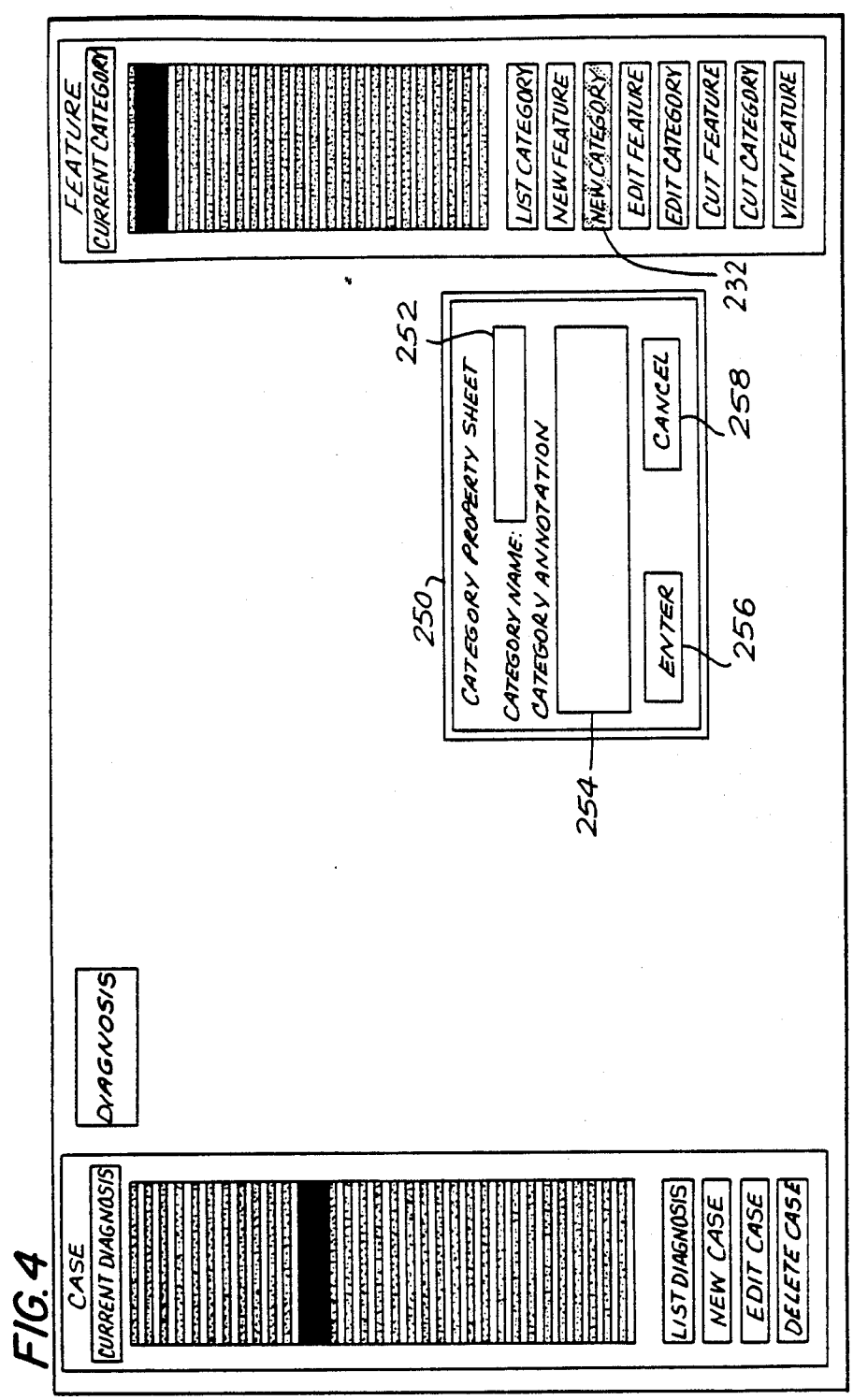

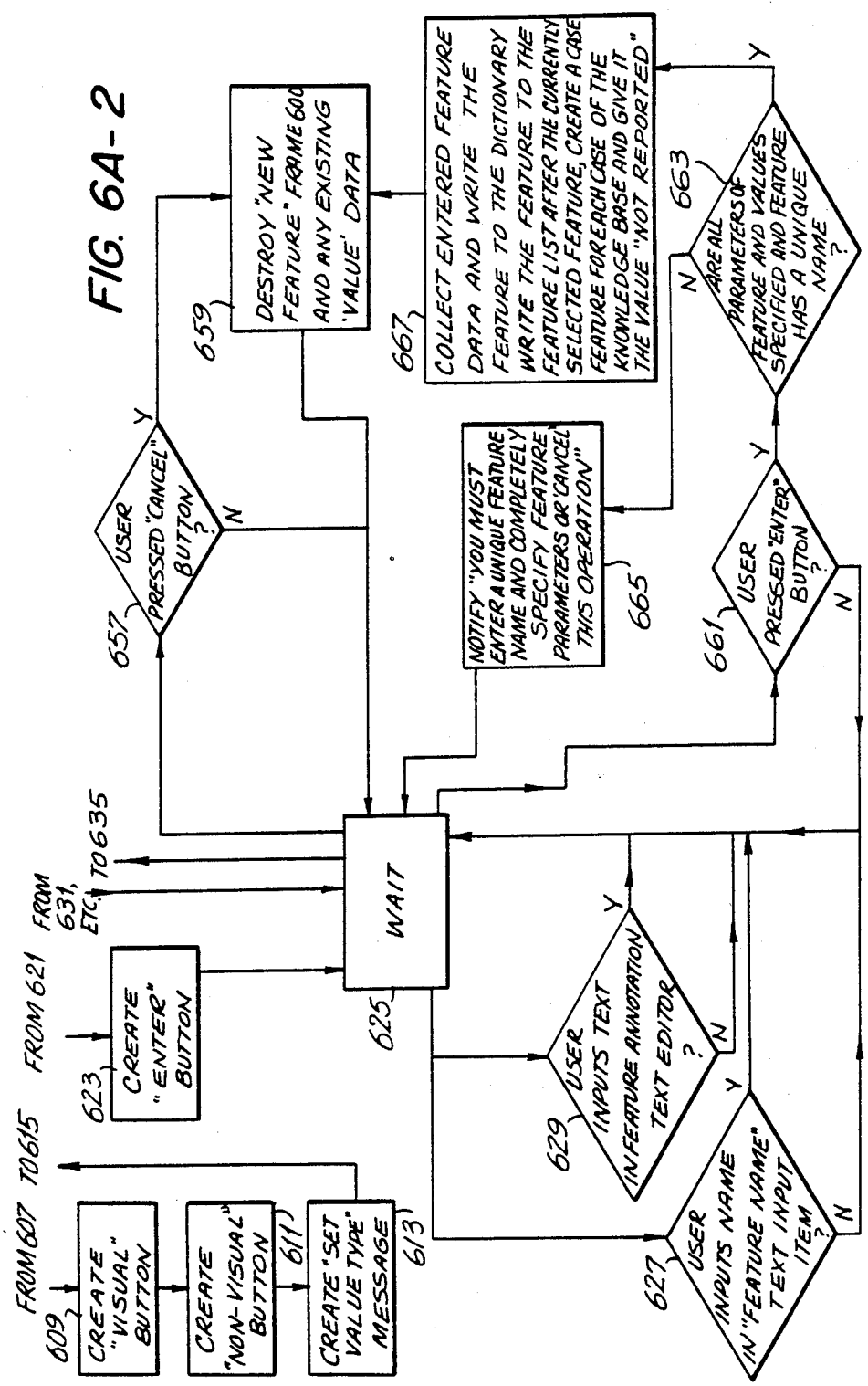

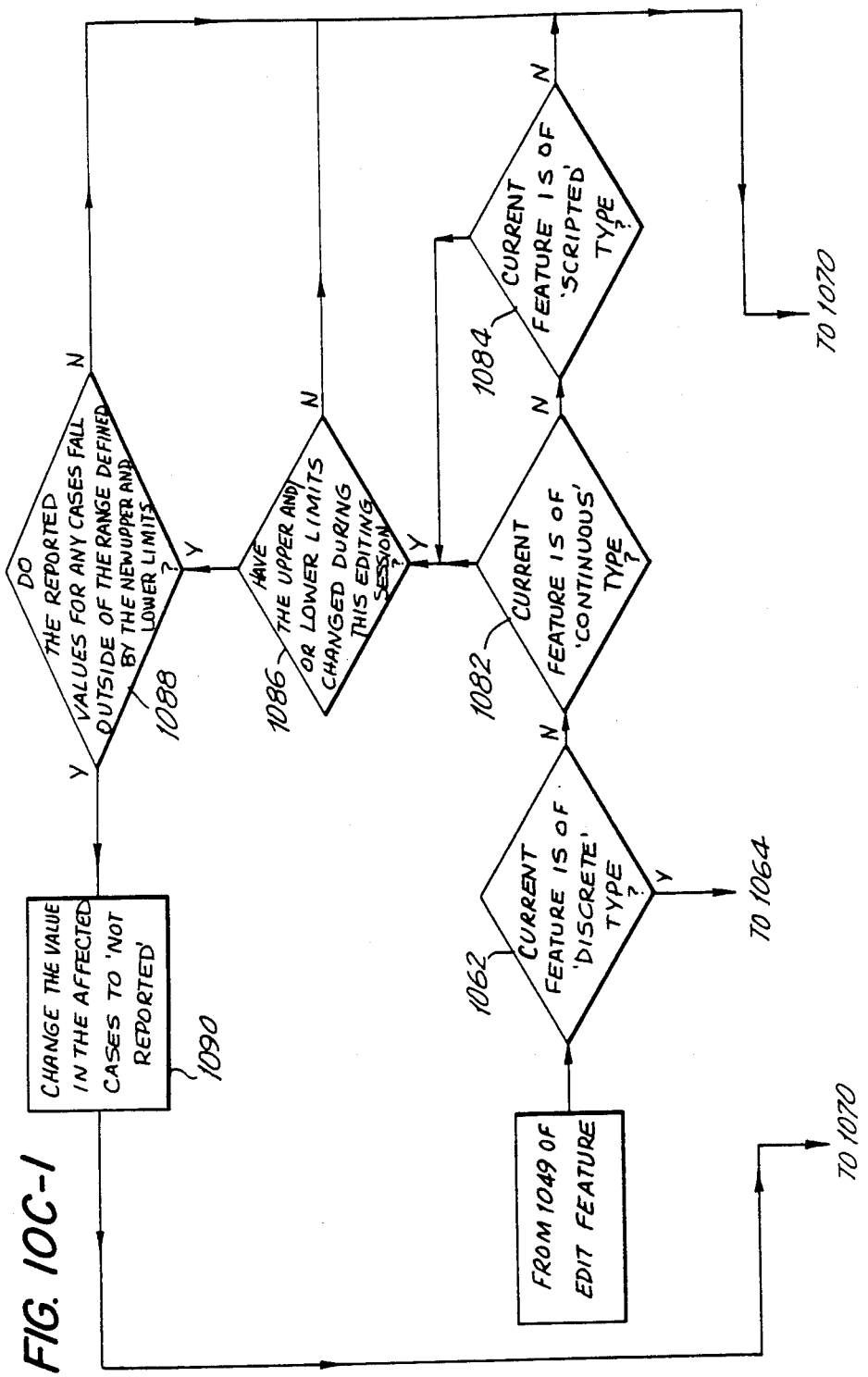
FIG. IOC-1

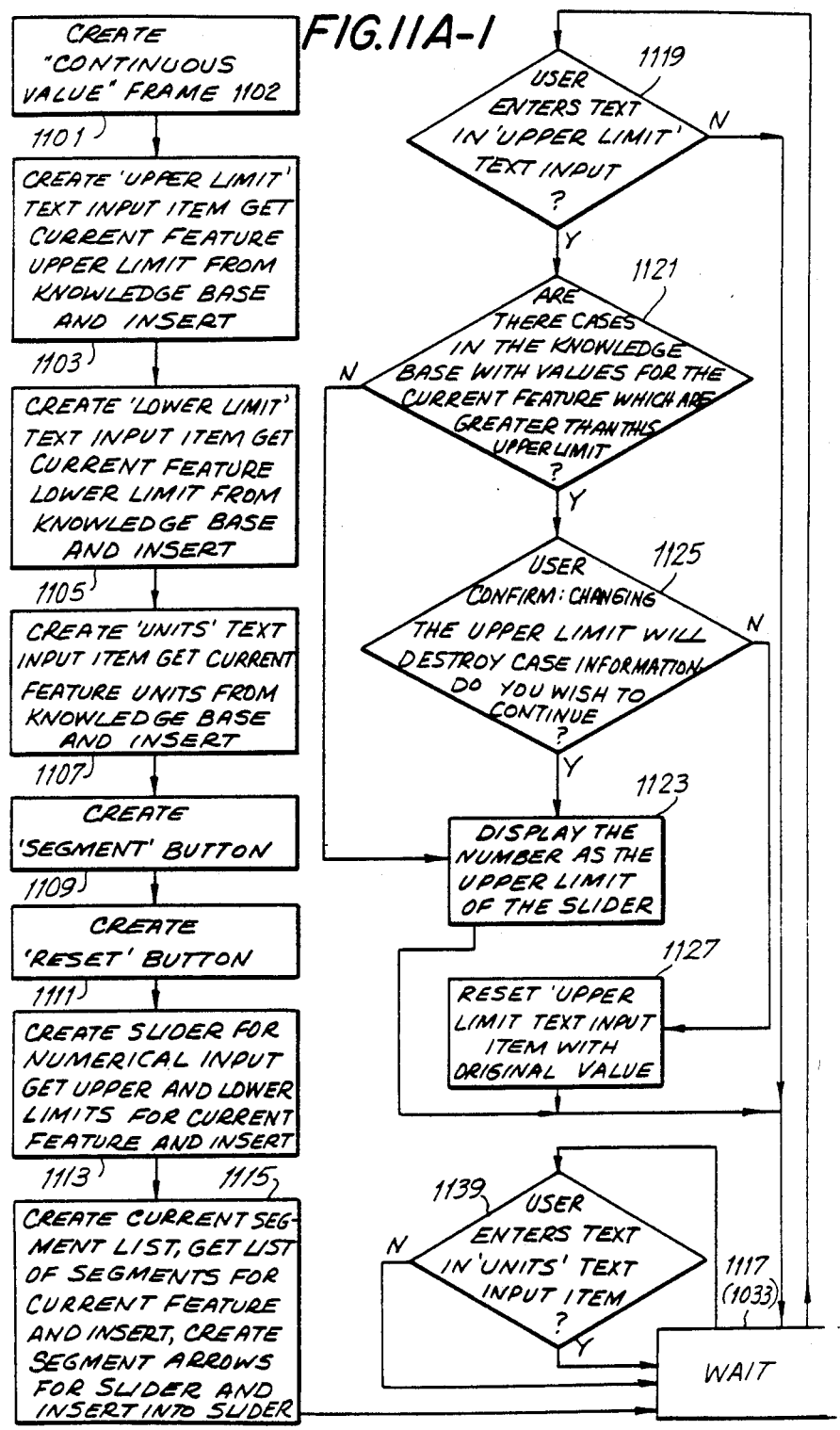

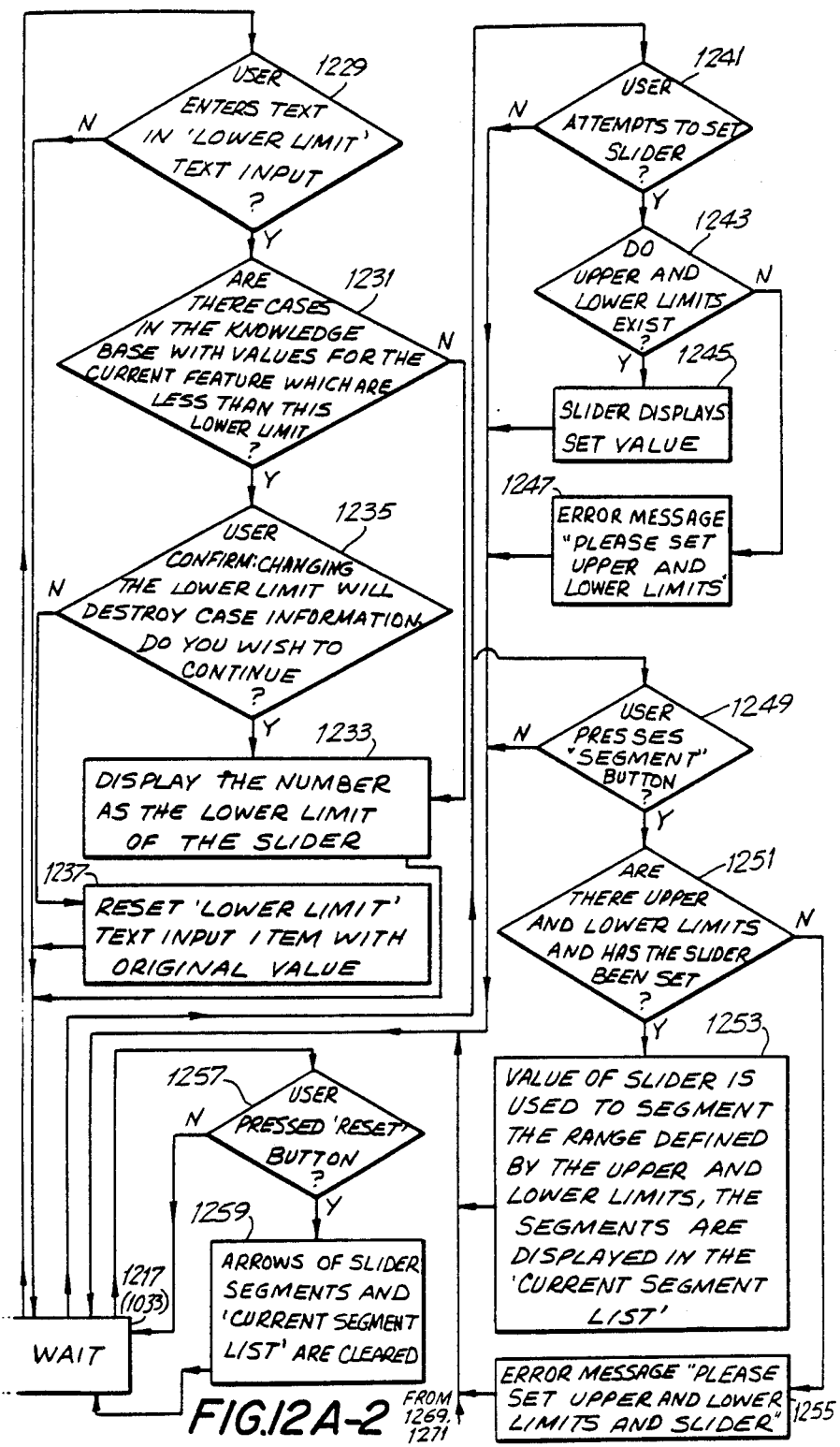

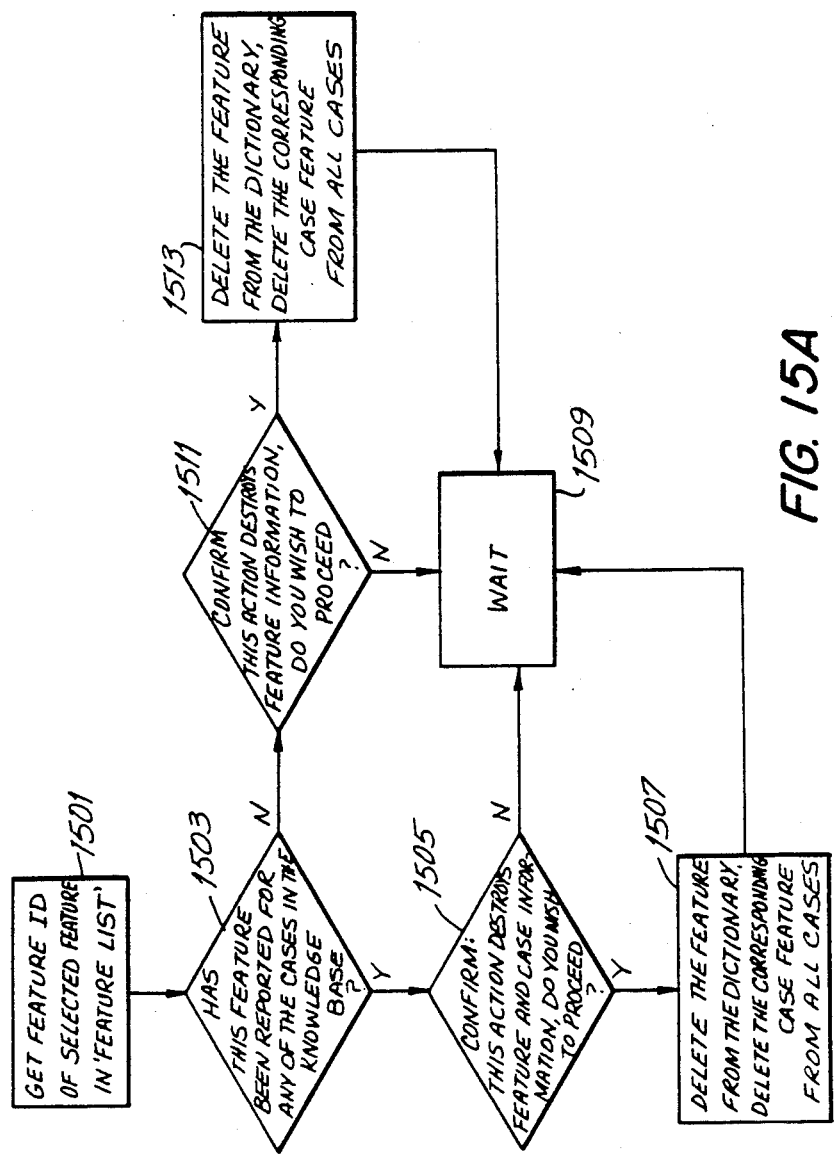

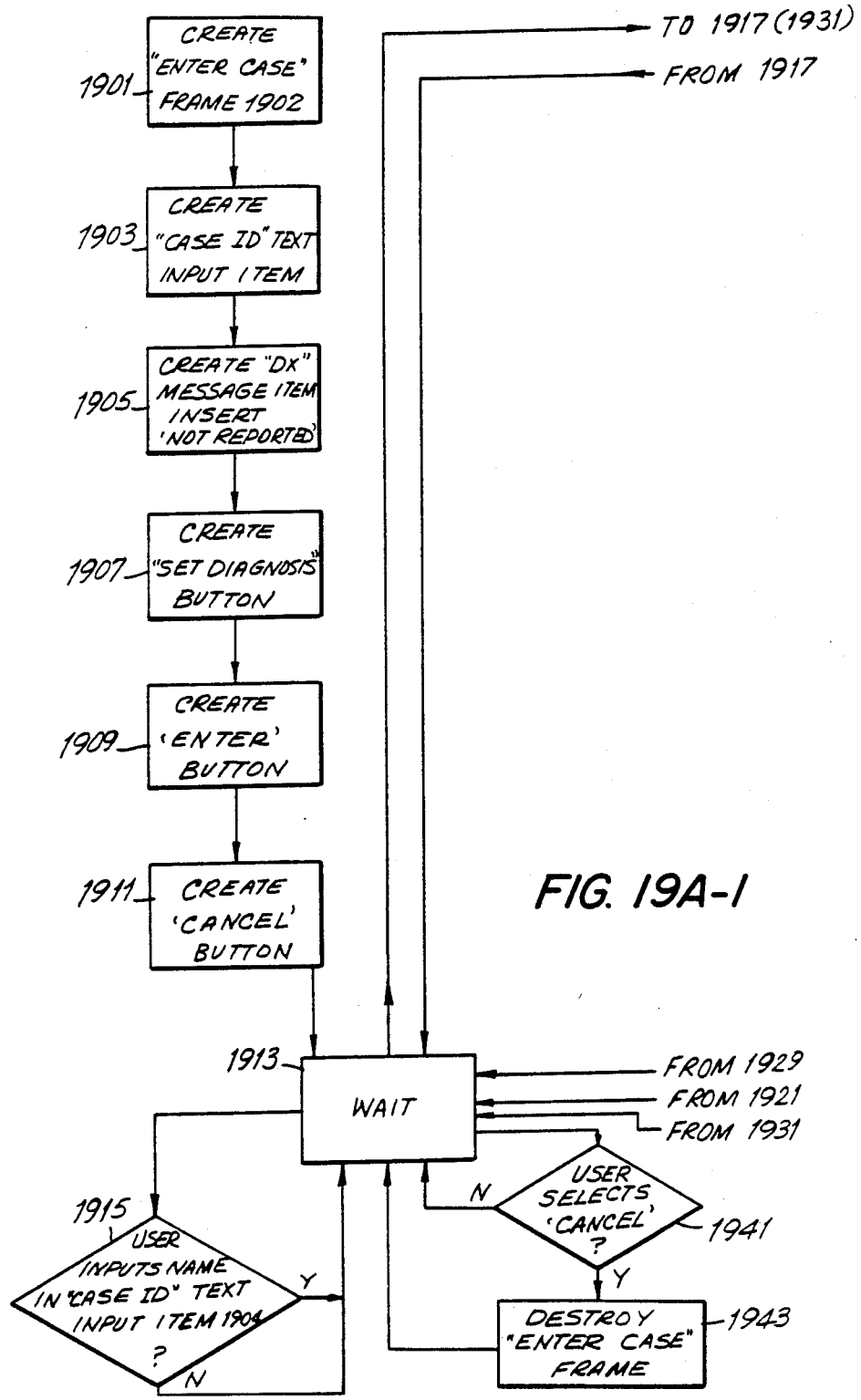

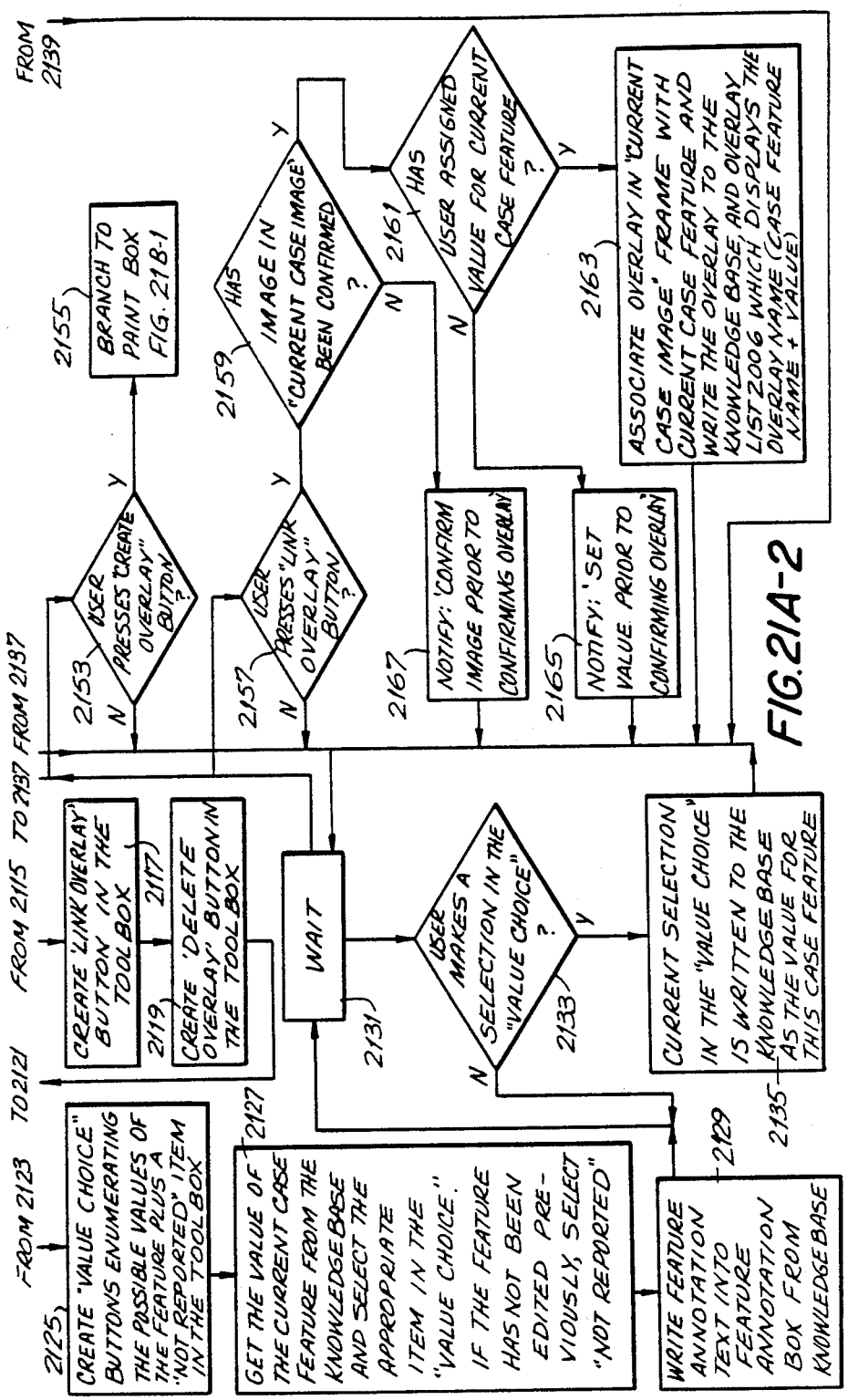

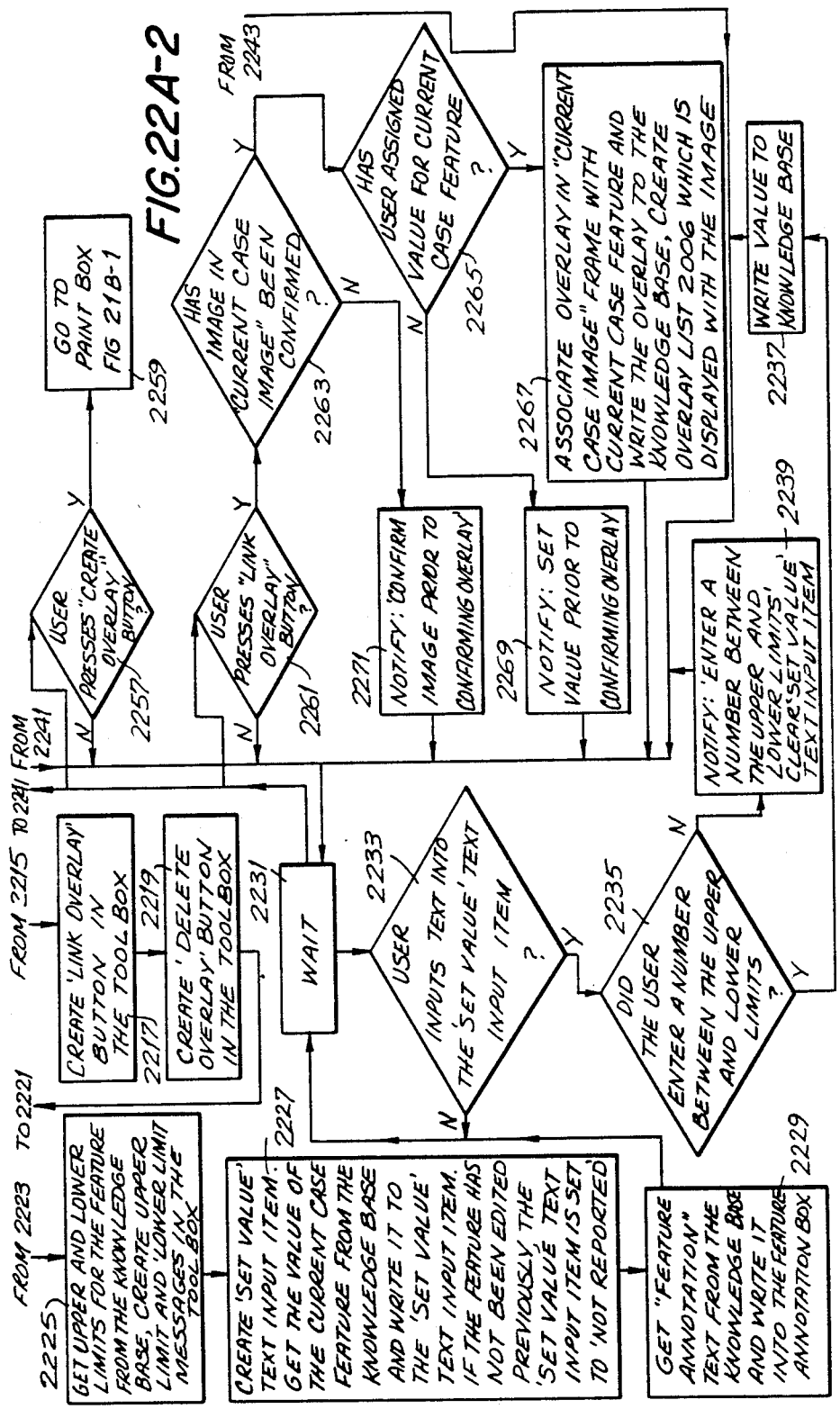

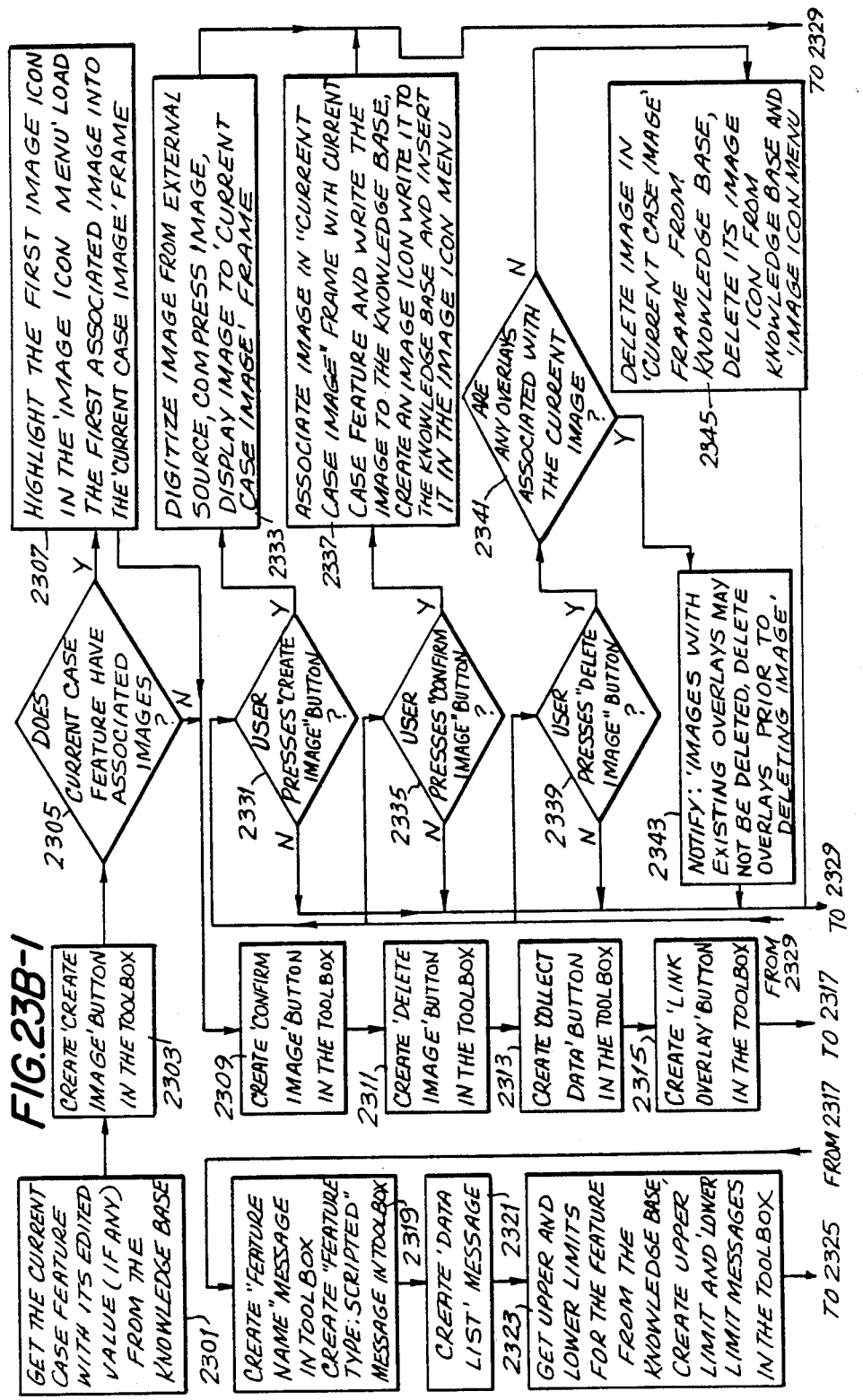

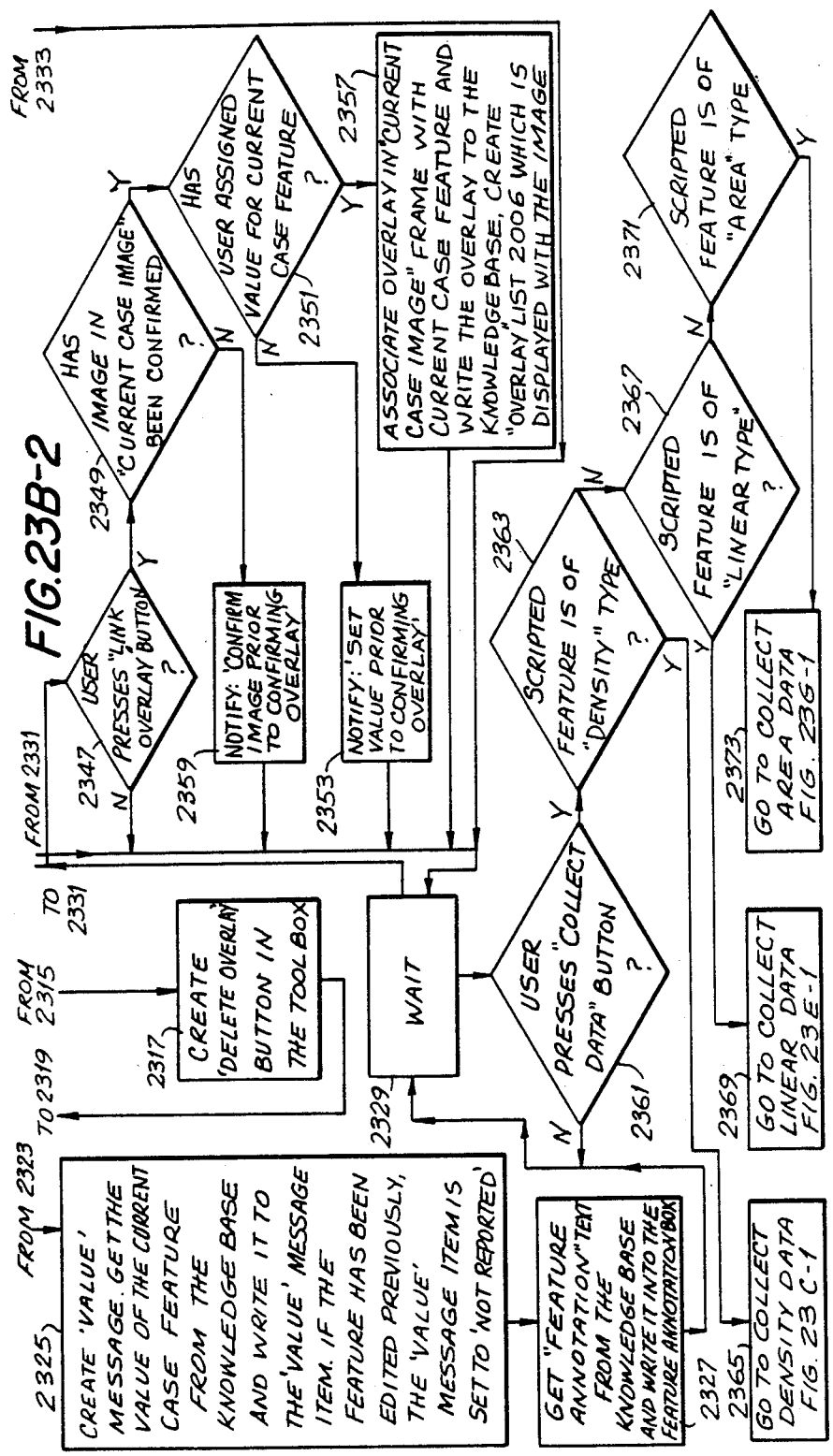

INTERACTIVE SYSTEM AND METHOD FOR CREATING AND EDITING A KNOWLEDGE BASE FOR USE AS A COMPUTERIZED AID TO THE COGNITIVE PROCESS OF DIAGNOSIS

FIELD OF INVENTION

This invention relates to the field of computerized data bases and, more particularly, to the creation of accessible knowledge bases which contain both pictorial images and textual information. Moreover, the invention provides an interactive system and method to create, edit and utilize such a knowledge base that finds particular application in medical diagnosis, and especially pathology and radiology diagnosis.

BACKGROUND OF THE INVENTION

Electronic information storage systems having data bases which can be accessed by computer are well known. Some examples of accessible data bases are the Lexis legal research system, a data base containing legal information, and the Dialog information retrieval system, which provides access to numerous scientific and business data bases. These and several other data bases have succeeded in offering the user a vast amount of textual information which is rapidly accessible and relatively inexpensive to retrieve. However, the ability to search electronically for desirable information in these data bases often requires extensive training and skill.

With some notably few exceptions, such as the experimental patent search and retrieval system of the United States Patent and Trademark Office, most data bases do not store and thus are unable to display pictorial or other photographic/visual information. One of the reasons for this is that such image information generally requires a great deal of computer memory to store it. Although computer memory has been a decreasing cost in computer systems recently, it is still an important factor in system design and application and the amount of storage required for images is very large. Also, as a consequence of the large amount of memory space required to store images, the time required to access, process and display image information can be lengthy, so lengthy as to be unacceptable.

In addition to their failure to provide pictorial image display, most, if not all data bases that are available commercially provide limited data access tools for the user to retrieve information. This has influenced the use of these data bases because there has been a general inability to assure internal consistency of the information represented by that data base. For example, consistency of data is extremely important for applications wherein that data represents observations by a human author in a subject under investigation. Since such observations are inherently subjective to some degree—the characterization of what one individual observes will not necessarily be the same as the characterizations observed by another, and what one perceives today may differ from his perceptions tomorrow—it is important that the author of the data base have the ability to verify his observations and conclusions over a period of time, and to correct or modify those observations and conclusions for the sake of consistency. Consequently, the users of such data bases in scientific disciplines may not have sufficient confidence in the reliability of the data therein or the dependability of observations, conclusions, characterizations or deductions that may be included in the data base.

A useful field of scientific endeavor in which a text and pictorial data base finds ready application is medical diagnosis. A physician, even a specialist, often needs assistance in diagnosing a medical condition or disease based upon his clinical observations of a patient. Of course, reference to various textbooks, learned journals and other sources of expert information are quite useful and, of course, have been relied upon, but the wealth of such information now available is substantially limited by the lack of any useful resource to access it. In general, state-of-the-art electronic libraries, although proposed for medical research, have not been enthusiastically embraced by many practicing physicians. It is believed that this is due, in part, to the high cost of providing a centralized, accessible data base, in part to the need for special training in using computerized systems for data retrieval and in part to the lack of existing reliable data bases. Nevertheless, the primary reason for limited use of such electronic libraries by physicians appears to be attributed to the lack of confidence in the reliability of medical data that may be stored therein, such as diagnoses based upon clinical or histological observations, characterizations and conclusions. There is little assurance that such data is internally consistent or authenticated or even verifiable; and it is difficult to build an internally consistent data set that is created with the authenticity needed for diagnoses.

The field of pathology offers an excellent opportunity for the creation and use of a data base which would assist the pathologist in identifying characteristics associated with various diseases and in formulating his diagnosis. An internally consistent data base, that is, a knowledge base, created by an expert from case histories of numerous patients would provide a pathologist with reference materials for comparison with his present observations, thereby facilitating his diagnosis. Preferably, the knowledge base should include both textual and pictorial information derived from clinical features, histological designations and features observed from cytology specimens, thereby providing the best evidence of cases which resulted in specific diagnoses by the expert. The knowledge base should be dynamic in the sense that during its creation, newly discovered characteristics observed in patients can be added thereto and other characteristics which prove to be of lesser diagnostic importance can be deleted therefrom, thereby improving, over time, the utility of the data base in aiding a pathologist in identifying maladies and diseases. Additionally, the knowledge base should be interactive not only to permit use thereof by the pathologist but also to provide the expert who is creating the knowledge base with the retrieval tools needed to observe and compare previous observations with present analyses so as to maintain consistency of the information in the knowledge base. Since histological and cytological characterizations are, to some extent, subjective, it is useful for the expert to compare a feature which he observes in one patient or sample to the same feature which he observed in a previous patient or sample. For example, it may be important to characterize the shape of a specimen cell; and what might presently be observed as an oval or round cell might previously have been characterized as an irregular cell.

It is believed, however, that at the present time no interactive system is available with the appropriate access tools for use by an expert to craft a knowledge base which that expert, as well as a jury of experts, can scrutinize for consistency and authenticity, and for subsequent access and use in the diagnosis of disease. More broadly stated, it is believed there are no presently available interactive systems for providing a knowledge base for use as a computerized aid to the cognitive process of diagnosis. Nor is there known to be available an electronic system for use by an expert to create a specific knowledge base of information which, when accessed by a user, serves as an aid in cognitive analysis of observed characteristics.

A knowledge base, as that term is used herein, differs from the classic concept of a data base in that the information represented by the knowledge base may be crafted to assure its consistency, and is based upon the recognized "knowledge" of the individual(s) who creates it.

OBJECTS OF THE INVENTION

Therefore, it is an object of this invention to provide a method and apparatus for crafting a knowledge base which contains both textual and pictorial information that is internally consistent and which can be accessed rapidly.

It is a further object of this invention to provide a knowledge base which contains both textual and pictorial information and which, when access to the knowledge base is requested by a user, retrieves both types of information corresponding to the particular request.

It is another object of this invention to provide a computerized pathology knowledge base which contains textual information on and pictures of various diseases and which a pathologist or other physician would use with a high degree of confidence.

Still another object of this invention is to provide a computer system which creates particular overlay images and links those overlay images to pictorial images to direct the user to important features present in electronically displayed pictures.

Another object of this invention is to provide pictorial images helpful in diagnosing a disease, wherein relevant portions of the images are highlighted by symbols and annotated with text.

A further object of this invention is to provide a system and method for creating a knowledge base which, when accessed, combines retrieved alphanumeric and pictorial information into individual, separately viewable video displays.

It is an additional object of this invention to provide a computerized pathology knowledge base which presents both textual information and related visual imagery for simultaneous display.

A further object of this invention is to provide a method and system for storing linked alphanumeric and visual information and which organizes the stored information into easily accessible categories.

A still further object of this invention is to provide a method and system which allows the user to select the manner and format used to organize alphanumeric information and visual images.

Another object of this invention is to provide a method and system for use by an expert pathologist to create and structure a computerized pathology knowledge base containing both text and visual images in a way which the expert believes will provide the most logical access to the information therein.

An additional object of this invention is to provide a method and system by which a user may modify or change the contents and organization of a stored knowledge base with a minimum number of computer commands.

Still another object of this invention is to provide a method and system for crafting a knowledge base comprised of alphanumeric and visual information which can be accessed and used to permit easy comparison between stored data and new data.

Yet another object of this invention is to provide a technique for creating a knowledge base for training a user in a particular field or domain represented by that knowledge base by providing a structured and preplanned examination of relevant data from within the knowledge base.

A further object of this invention is to provide a system which uses artificial intelligence to help assist the user in accessing and retrieving data from the knowledge base.

Still another object of this invention is to provide a computerized system which assists a physician to reach a diagnosis using a computerized pathology knowledge base that contains both text and visual images.

Yet a further object of this invention is to provide a technique for creating an electronically accessible knowledge base formed of case records of diseases, wherein each case is formed of features observed in a disease and each feature is either selected from a store of pre-established features and assigned one of plural preset values available for that feature, or is newly created by an author/user.

An additional object of this invention is to provide a technique as aforesaid wherein a user may edit the knowledge base to add or delete features from substantially all stored case records with a minimum of computer commands.

Another object of this invention is to provide a technique as aforesaid wherein the several features and values included in a case record are linked and wherein a case record is retrieved on the basis of selecting for display a feature included in that case record, whereby consistency in evaluating a feature in different case records is improved.

A still further object of this invention is to provide a technique as aforesaid wherein video image data of a subject, such as a microscope specimen, is generated, linked to a feature and stored in a case record for subsequent retrieval and display to demonstrate to a user the previously observed feature.

Yet an additional object of this invention is to provide a technique as aforesaid wherein the knowledge base is searched for all case records which contain one or more features selected by a user for retrieval and display of those case records, and particularly pictorial information included in those case records.

It is an additional object of this invention to provide a technique as aforesaid wherein the distribution of cases having different values of the selected feature(s) is displayed to indicate to the user the relative numbers of cases containing such different values and thereby apprising the user of the behavior of this feature in a particular diagnosis.

Another object of this invention is to provide a technique as aforesaid wherein the features are characterized as discrete or continuous, and wherein the values may be selected from a store of preset values or may be freely selected by the author/user, or may be measured.

Further objects and advantages of the invention will be apparent from the ensuing detailed description of a preferred embodiment thereof, and the novel features will be particularly pointed out in the appended claims.

SUMMARY OF THE INVENTION

In accordance with one application of this invention, a medical/pathology knowledge base containing textual and pictorial information on various diseases is created and stored in computer-readable form. In one embodiment, the knowledge base includes user-selectable designations of diagnostic features which the author of the knowledge base (i.e. an "expert" author) determines are characteristic of respective conditions to be diagnosed. These features preferably comprise a case record of a patient diagnosed with a particular disease; and several case records are stored and retrieved for subsequent display of the features therein and of one or more pictorial images of those features. The knowledge base is used with a high speed computer system whose memory preferably includes a compact disc laser recorder/playback system. The laser disc (known as a "WORM") provides a very large memory suitable for storing pictorial images with relatively rapid access thereto. These pictorial images are linked to case records which may be stored in other storage devices, such as magnetic disc, whereby the retrieval of a case record accesses the pictorial images linked thereto and the retrieval of a pictorial image accesses the linked case record, thereby displaying the pictorial image and features of that case record.

Preferably, the knowledge base is organized and codified by a recognized expert in the field, for example, in pathology. The invention provides the expert with a highly flexible format and data access tools which allows the expert to structure the data in almost any manner he believes will provide the easiest and most rapid access thereto, thereby helping users of the knowledge base to reach correct diagnoses. Creation and editing the knowledge base can be made with only relatively few computer commands.

The present invention also provides the user/pathologist with numerous ways to access and use the knowledge base. Information on specific diseases may be requested, such as a request for retrieval of all cases having specified features or a request for all cases in which a particular disease was diagnosed. Side-by-side presentation of pictorial images and display of text information relating to different diseases or features assist evaluation and diagnosis.

The preferred embodiment of this invention includes a programmable processor which is in data communication with an input means, a display and an accessible storage means, the processor being programmed to respond to the input means to establish user-selectable designations of diagnostic features which the author determines are characteristic of respective conditions to be diagnosed and to establish user-selectable values of those features. Pictorial image data produced by an image input means is linked by the processor with one or more features and is stored in the storage means. Preferably, the image data is stored on the aforementioned WORM device, while the feature data is stored in another storage device, such as a magnetic disk.

In one aspect of this invention, the processor is programmed to cause the display to provide prompts for guiding the author in selecting respective ones of established features and to assign an established value to a selected feature which the author observes in a pictorial image. The processor is further programmed to enable the author to create new features (i.e. features which had not been established and stored previously) and to assign new values to those newly created features. One characteristic of this aspect is that the knowledge base created by the processor is comprised of case records, each case including feature, value and (in most but not necessarily all cases) pictorial image data; and the addition of a new feature to one case results in the addition of that feature to all cases, this newly added feature awaiting assignment of a value in such other cases. Likewise, the deletion of a feature from one case (as opposed to merely the assignment thereto of a "0" value) results in the deletion of that feature from all cases.

In accordance with another aspect of this invention, the linking of features and pictorial image data in a case record cooperates with the programming of the processor to retrieve all case records having the feature(s) selected by the author, from which case records the author may display text and pictorial information contained within a desired one of those retrieved case records.

In accordance with yet another aspect of this invention, the processor is programmed to respond to the input means to generate overlay data which, in turn, is displayed as an overlay superimposed over a pictorial image for the general purpose of identifying with greater particularity a particular feature which is included in the displayed pictorial image. The processor is programmed to link the overlay data with the pictorial image data and to store that overlay data such that subsequent retrieval of this pictorial image data will be accompanied by the retrieval of its associated overlay.

As yet another aspect of this invention, the processor is programmed to retrieve all case records having the particular feature(s) selected by the author; with the expectation that the values of such feature(s) normally will vary from one case to another. The processor is programmed to determine the distribution relative to each other of such cases having different respective values for the feature(s) and to display such distribution. Hence, the user of this invention is provided with an indication, such as a graph-type display, of the number of cases in which a particular feature exhibits a first value, the number of cases in which that feature exhibits a second value, and so on. For example, if the feature in question is age of a patient, a display is provided of the number of cases in which the patient is less than 20 years old, in which the patient is between 20 and 30 years of age, in which the patient is between 30 and 40 years of age, etc. These cases may be, for example, of those patients having non-inflammatory cells of a particular size and shape and of particular pleomorphic size and in which non-inflammatory cells exhibit a certain type of chromatin pattern, etc. The processor is additionally programmed to search for case records having those particular features which are entered by the user, in accordance with typical boolean combinations of those features (e.g. all cases having each and every one of the entered features or all cases having at least one of those entered features).

In accordance with yet another aspect of this invention, each case record may be linked with several pictorial images all of which may be retrieved from the storage means when the case record is accessed. As one characteristic of this aspect, all of the linked pictorial images are displayed concurrently, in relatively reduced size, and the processor is programmed to permit the user to select one of those reduced size images (as by operating the input means) for display in relatively magnified size. Thus, pictorial displays of different features contained in the case record, together with attendant overlays, may be selected, as desired, by the user.

As yet another aspect of this invention, the features which may be included in a case record may be characterized as exhibiting discrete or continuous values. The processor is further programmed to permit editing of already established features or newly created features; whereupon when a feature is designated by the author as having a discrete value, preset value data that has already been provided in the knowledge base is displayed for assignment by the author to the feature or, alternatively, the author may operate the input means to enter into the knowledge base a new discrete value. Alternatively, if the feature is designated by the author as having a continuous value, prompts are displayed for the author to select a range for the continuous value which may be assigned to that feature.

In accordance with a still further aspect of this invention, the processor is additionally programmed to measure a value for a feature. For example, the feature may be the length of a cell or the distance between substances observed in a cell; or the feature may be the area of a cell or cell nucleus or diseased portion of tissue; or the feature may be the density of certain material in a designated portion of a cell or cell tissue. Such length, area, density is measured by the processor.

In accordance with yet another aspect of this invention, to simplify the storage and display of features, the processor is programmed to establish author-selectable categories of features, each category being comprised of a unique set of features. Operation of the input means is used to establish such categories and to link an established category to those features which the author determines should be included therein. Hence, for review or display purposes, the author need not access each and every feature from the knowledge base, particularly if several features are not of interest to the author. Rather, the author merely need retrieve the far lesser number of categories from the knowledge base and then may select the particular category from which features are to be reviewed or displayed. The processor is additionally programmed to add or delete categories from the knowledge base, thereby adding or deleting those categories from the individual case records stored in the knowledge base.

BRIEF DESCRIPTION OF THE DRAWINGS

The following detailed description, given by way of example, and not intended to limit the present invention solely to the described embodiments, will best be understood in conjunction with the accompanying drawings in which:

FIGS. 2A-1,2 is a flow chart representing the manner in which the display of FIG. 2 is produced;

FIG. 3 illustrates a display in which stored categories are listed;

FIG. 4 is a display used when creating a new category;

FIG. 6A-1,2 is a flow chart representing the manner in which a new feature is created;

FIG. 8A-1,2 is a flow chart representing the manner in which the continuous value feature is created;

FIG. 9A-1,2,3 is a flow chart representing the manner in which the scripted value feature is created;

FIGS. 10A-1,2; 10B-1,2; 10C-1,2 constitute a flow chart representing the manner in which a discrete value feature is created;

FIG. 11A-1,2 is a flow chart representing the manner in which the continuous valued feature is edited;

FIG. 12A-1,2,3 is a flow chart representing the manner in which the scripted value feature is edited;

FIG. 13A-1,2 is a flow chart representing the manner in which a graphical display of the distribution of a particular feature in various case records is obtained;

FIG. 15A is a flow chart representing the manner in which a feature is deleted;

FIG. 17-1,2 is a flow chart representing the manner in which a case is created and utilized;

FIG. 19A-1,2 is a flow chart representing the manner in which new case information is created;

FIGS. 20A-1,2; 20B-1,2 are flow charts representing the manner in which case information is edited;

FIGS. 21A-1,2; 21B-1,2 are flow charts representing the manner in which the aforementioned features are highlighted;

FIG. 22A-1,2 is a flow chart representing the manner in which the continuous values features are highlighted;

FIGS. 23B-1,2; 23C-1,2 are flow charts representing the manner in which the scripted feature images are highlighted;

FIG. 23E-1,2 is a flow chart representing the manner in which those parameters are obtained;

FIG. 23G-1,2 is a flow chart representing the manner in which the measurements of scripted value features are obtained;

FIG. 26A-1,2 is a flow chart representing the manner in which the displayed diagnosis tree is produced;

FIG. 27A-1,2 is a flow chart representing the manner in which the display of FIG. 27 is produced;

FIG. 28A-1,2 is a flow chart representing the manner in which a diagnosis node is edited;

DETAILED DESCRIPTION OF PREFERRED EMBODIMENT

The present invention finds ready application in the field of pathology. Consequently, it is described in that environment. However, it will be apparent that the presentation of pictorial images in conjunction with textual data which relate to those images and assist in the evaluation of them is valuable in any area where the appearance of an object under study/examination is of critical importance. These areas may include other disciplines of medicine, such as dermatology and ophthalmology, as well as such non-medical areas as engineering, art history and biology, to name but a few examples. It will, therefore, be appreciated that this invention finds general utility in the cognitive process of diagnosis.

Although the equipment and computer components used in this invention are conventional and known in the art, it is nonetheless useful to describe the hardware, thereby placing the invention in its operational environment.

Figures 1, 2A:
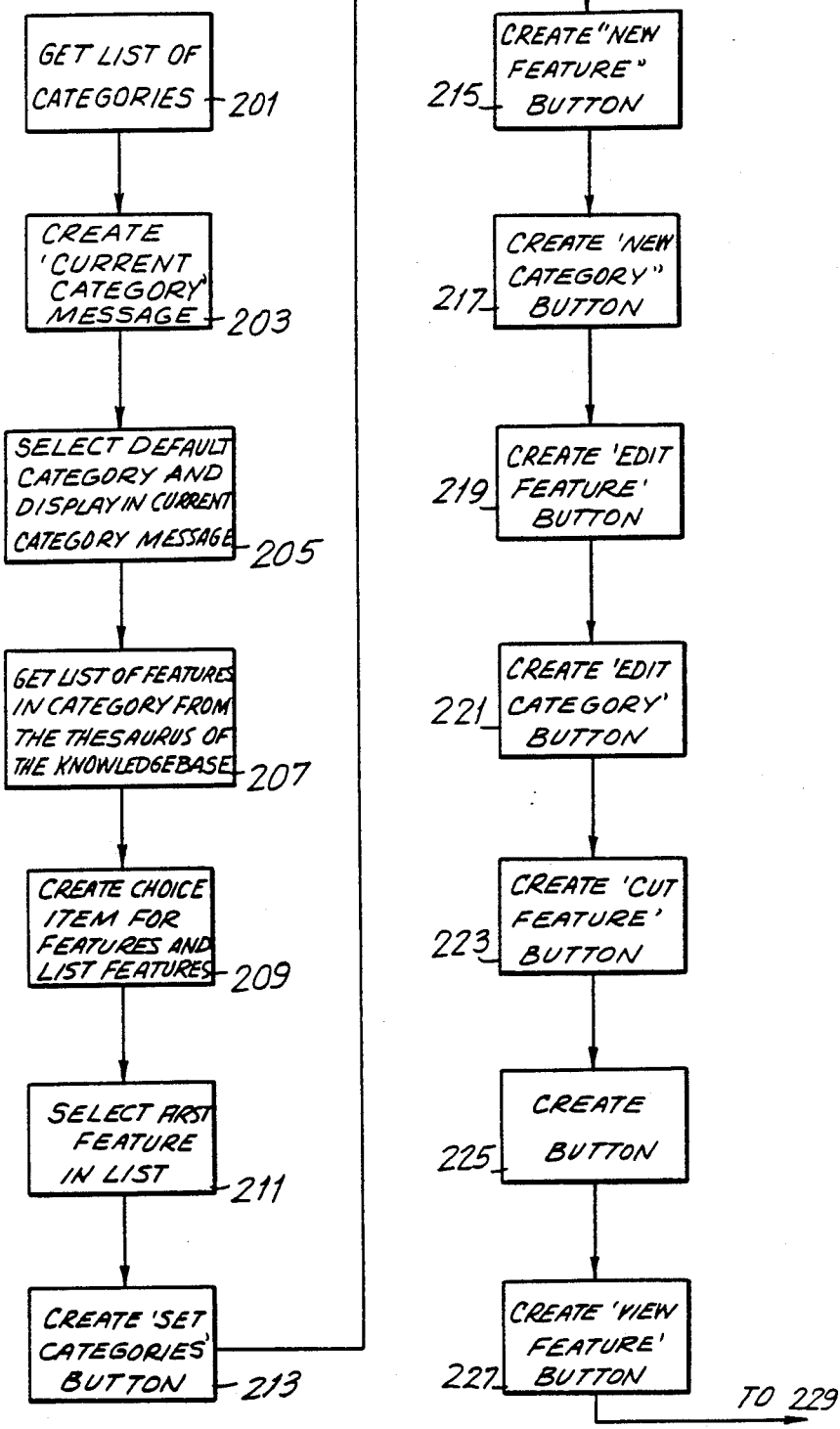

Referring now to FIG. 1, the present invention is comprised of a computerized authoring system 100 formed of a processor 102 which cooperates with a magnetic storage device 104, a monitor 106, a keyboard 108, a manually movable cursor controller 110 and a video camera 116. Processor 102 preferably is a microcomputer such as a Sun model 3/110 supermicrocomputer manufactured by Sun Microsystems operating under the Unix 4.2/5 operating system software and which uses an I.E.E.E. 696 bus with 1 megabyte of random access memory. Those of ordinary skill in the art, familiar with the Unix-controlled Sun microcomputer will recognize such advantageous operating features as layering of programs and displays, background operation of programs, and use of a manual cursor controller (conventionally known as a "mouse"), among others. Processor 102 is provided with graphics computer circuit cards which can capture, digitize, display and process a 512×512×8 bit image.

To capture images, a microscope 114, such as a Leitz 12, is fitted with a trinocular adapter for video interface with video camera 116, such as an Ikegami RGB camera. Preferably, the video signals produced by camera 116 are digitized either by a suitable analog-to-digital converter included in or coupled to the camera, or by a converter provided in processor 102. Video images are displayed on monitor 106 which is a high resolution RGB monitor adapted to display 1100×900 pixels.

The system also includes a video disk recorder/player 112, such as an optical disk Write Once Reproduce Many (WORM) device. The very large storage capacity of this device (e.g. on the order of about 1000M bytes), coupled with its rapid access time, make the optical disk an ideal medium for the storage of images derived from video camera 116. Roughly 2000 images each of 512×480×8 bits can be stored on a single optical disk. It will be recognized that a library of prepared optical disks enables the illustrated apparatus to be used in diagnosis, analysis or "problem-solving" in a particular field or discipline (i.e. in a particular "domain") for which the disks have been prepared.

Although other computers and a different selection of peripheral equipment may be used in the present invention, such equipment should be selected with an awareness that high processing speeds and large memory capacity are important considerations.

The system shown in FIG. 1 relies upon image compression techniques to enhance its video image storage capability. This results in an effective increase in the number of images that may be stored on optical storage device 112. The storage and manipulation of visual images, either color or black-and-white, is known in the art. Such images are typically processed to form a pattern of pixels, with each pixel representing the color or black and white value at a particular location. For example, in the present invention, images are divided in rectangular grids measuring 512 pixels in length and 480 pixels in width, with a total of approximately 246,000 pixels being used to represent the image. In a typical black and white image system, each of these pixels is assigned a value of from 0 to 255, with 0 representing black and 255 representing white (or vice versa). In terms of the amount of memory required to store such an image, each pixel requires 8 bits to represent its darkness value. This results in a memory requirement of approximately 220K bytes per image. In a typical color system, the image is formed of the three primary colors, red, green and blue, with each pixel in the image being assigned an 8 bit value for each of the three colors. This method of digitizing a color image requires approximately 775K bytes to store a single color image. Although the cost of memory has decreased markedly, even with optical storage devices such as the laser compact disc recorder/player, which has both a very large storage capacity as well as rapid access to stored information, storage of color images in the conventional manner would require too much time both to manipulate the images and to access them.

The present invention employs a technique for digitizing and storing visual images which reduces the storage requirement of a single color image from 775K bytes to 220K bytes yet retains most of the information provided in the original image and provides a highly acceptable video image for display on monitor 106. Although the number of bits required for each original image is still large, a useful number, roughly 2000 images, can be stored on a single WORM device, and the processing and presentation of a single image may be performed in less than two seconds, which is an acceptable time delay.

Color video camera 116, which is mounted on microscope 114, supplies video signals to processsor 102 comprising three separate images, a red image, a blue image and a green image, where each pixel in each image is represented by an 8-bit value designating its respective red, green and blue value. Once a color "plane" (image) has been supplied to processor 102, a data reduction, or compression, process is carried out. For the purpose of the presently described embodiment of this invention, namely a knowledge base system for pathology, it has been determined that adequate color accuracy will be achieved if only 6 shades of red, 7 shades of green and 6 shades of blue, each shade being of increasing color intensity, are provided. Of course, the distribution of color shades may be altered or modified as desired.

As the data reduction process operates in substantially the same way on each of the three color images or "planes" which comprise a single visual image, only the red "plane" processing will be discussed. The red plane is acquired as a 512×480 pattern of pixels, with each pixel having a value of 0 to 255, thus providing 256 shades of red. However, only 6 shades of red need be stored. Instead of each pixel having a value representing one of 256 shades of red, each pixel of the red plane image is provided with a value representative of only one of 6 shades of red. Each of these shades represents the maximum shade of the color within a given range of the original 256 shades. The original 256 shades are divided into six ranges with each range encompassing 43 original shades (6×43=258). For six equal ranges, the original 256 shades are divided into (0–42), (43–85), (86–128), (129–171), (172–214) and (215–257), and these ranges are represented simply as the values 42, 85, 128, 171, 214 and 257. For example, if the original pixel had a "shade"value of 70, it would be assigned a value of 85, which represents the closest shade of red within the range (43–85) into which the original shade fell. Similarly, if the original pixel had a shade value of 51, it would be assigned a value of 42. Hence, these values are selected to divide the entire range of shades in a color plane into 6 evenly distributed ranges.

A potential negative consequence of this compression process is that resolution and contrast may be reduced because some visual information is lost when a range reduction process of this type occurs. To minimize this problem, an error averaging process is used. Each time a pixel's color value is reduced or increased to a value in the relevant range, the resulting net error is divided among the pixel's immediate neighbors, thus lightening or darkening their shade of color prior to their being processed. In terms of the array of pixels which comprises the image, the pixel to the right of the pixel being processed, as well as the pixels vertically below it receive a portion of the total error. For example, assume a given pixel has a red value of 74. As 74 is closer to 85 than 42, this pixel receives a value of 85. However, this introduces an error of 11 shades of red. As the final value of red assigned to this pixel is too large, the four neighbors of this pixel, designated as $N_1$–$N_4$, have their values reduced in the following manner: 7/16 of the total correction is applied to $N_1$ (the pixel to the right), 3/16 $N_2$ (the pixel below and to the left), 5/16 to $N_3$ (the pixel below), and 1/16 to $N_4$ (the pixel below and to the right). This is described more completely in "An Adaptive Algorithm for Spatial Greyscale" by Robert W. Floyd and Louis Steinberg. Other methods of distributing the collective errors could be used. In this case, the approximate result would be, that $N_1$'s shade would be reduced by 5, $N_2$'s shade by 2, $N_3$'s by 4 and $N_4$'s by 0. As can be appreciated, at the borders of the image, although the calculation of the corrections remains the same, corrections which would apply to pixels beyond the border of the image are discarded.

This method of reducing the number of color shades while maintaining resolution and contrast is applied to the green and blue color planes in the same manner is performed on the red plane. The final processing step combines the three color values into one 8 bit value per pixel. This is done by using a so-called "lookup" table, which resides in the system hardware, to assign a number from 0 to 255 which represents each particular combination of the 6 red, 7 green, and 6 blue shades. Consequently, the requirement for storing essentially three separate color images, each requiring 220K bytes of memory, is reduced to storing only one image of 220K bytes, without any serious deterioration of the image contrast or resolution.

Referring again to FIG. 1, processor 102 is in data communication with each of monitor 106, keyboard 108, cursor controller 110 (referred to herein by its conventionally understood designation of "mouse"), optical storage device 112 and video camera 116. The program provided for processor 102; described in greater detail below, enables the illustrated apparatus to function as a computerized authorizing system by which a user, also referred to as an "author" or "expert", operates keyboard 108, mouse 110 and video camera 116 to create a knowledge base adapted to be stored and retrieved from magnetic disk storage 104 and from optical disk storage 112. In this regard, the magnetic disk storage preferably is formed as a so-called hard disk drive, several models of which are manufactured and commercially available from various sources. As will become apparent, the knowledge base is comprised of both textual and pictorial information; and it is convenient to store the textual information on hard disk 104 while storing the pictorial information on optical disk 112. Nevertheless, the pictorial information is sufficiently linked to the textual information as to be easily and readily read from the optical disk to display on monitor 106 particular characteristics which are identified by the textual information read from hard disk 104.

In the domain of pathology, for which the illustrated system is quite useful, the knowledge base created by the author who uses this system preferably is comprised of case records which document various diseases that the author has observed in patients. Of course, the purpose of this knowledge base is to assist in subsequent diagnoses by pathologists or other physicians based upon a comparison of the characteristics presently being observed with those characteristics included in the knowledge base. Accordingly, while the illustrated system is described herein as a computerized authoring system, it will be appreciated that this system is not limited solely to the function of "authoring", that is, the function of creating the knowledge base. Indeed, and as will become apparent from the ensuing discussion, system 100 operates readily as a reference system for the particular domain of case records which have been created, thus supporting the cognitive process of diagnosis, and also as a training system for the education and training of users in that domain.

In the interest of simplification, system 100 is described in the environment of pathology. When used as an authoring system, case records are created as a compilation of designations selected by the author of those diagnostic features which the author determines are characteristic of respective conditions, or diseases, to be diagnosed. These are referred to herein as "features" and each case record is formed of several features. It is expected that substantially all case records will include some of the same types of features, such as the identification of the case, the name of the patient, the eventual diagnosis, the identification of various biological cell analyses (the cytology number), date of cytology, the age and sex of the patient, as well as various other features which are relevant to the disease in question. It is convenient to classify various related features as "categories", wherein each category is comprised of a unique set of features. As examples, for the domain of cytology, the category of "patient descriptor" may include the features of age, sex and exposure to asbestos. The feature of "age" may be divided into ranges of "values", such as the ranges 0–20, 21–30, 31–40, 41–50, etc. The feature of sex may be assigned one of two values: male or female. The feature of asbestos exposure may be assigned the value of present, absent, questionable, unknown or other. As another example, the category of "current sites with positive cytology" may include the feature of "positive cytology, right pleura", with the possible values of present, absent, questionable, unknown and other. Another feature included in this category is "positive cytology, left pleura", with the possible values: present, absent, questionable, unknown and other. Another feature included in this category is "positive cytology, peritoneum", with the possible values: present, absent, questionable, unknown and other. Finally, another feature included in this category is "positive cytology, pericardium", with the values: present, absent, questionable, unknown and other. The various categories of features and possible values for these features for the domain of cytology is set out in Appendix A.

Prior to the formulation of even the first case record, the author, or expert, creates a glossary of categories, features included in each category, and the possible values to be assigned to each feature. This glossary, or dictionary (or sometimes described in the drawings as a thesaurus), is prepared on the basis of the expert's familiarity with the knowledge base domain in which he is an expert. It is expected that each case record subsequently formulated by the expert will include some, if not all, of the categories contained in the dictionary, and it is further expected that some of the features within a category simply will not be present in the case being documented. However, by first creating the dictionary of categories, features and values, the author is provided with a "template" of substantially all of the diagnostic features which should be addressed in documenting a case and in diagnosing a disease. From experience, it has been found that this template permits a case record to be created in about 15–20 minutes.

It will be recognized that some of the values assigned to a particular features may be simply numerical values (e.g. age, number of cells in various groups, percentage of cells reacting with keratin, etc.); other values may be best described as "textual" (such as the value, or description, of cell shape—which may be oval, round, irregular or variable—or cytoplasm density—which may be variable, dense, delicate or pale—or the chromatin pattern of a cell nucleus—which may be clear, pale, even, finely granular, coarsely granular, hyperchromatic, irregular or variable—etc.); and still other features may have values which must be measured (such as pleomorphic size of a cell, density of cell cytoplasm, or cell area). These values may be thought of as being discrete (a text description constitutes the value) or continuous (a numerical value), or calculated from measured parameters. This last type of value is described herein as a "scripted" value because the measurement thereof is determined on the basis of a "script" of specified procedures and algorithms. Once created by the expert, the dictionary contains substantially all of the features which the expert determines are most useful or influential in diagnosing diseases, together with substantially all of the values which may be assigned to each feature. For those cases wherein the preestablished features are not sufficient to characterize an observed condition, the expert operates the system, as will be described, to create a new feature and assign a value thereto. Advantageously, when a new feature is created, it is added to the dictionary and thus is included in the store of features (i.e. the feature bank) and is available to the expert for selection in characterizing observed conditions in future cases and for editing existing cases. For example, in observing cases of malignant mesthelioma, the expert might not have observed the halo inside the cell border of Pap-stained cytology specimens. Hence, the feature "inside halo" might not have been created and, thus, will not exist in the data base dictionary. If, during observations of other cases of malignant mesthelioma, the expert now finds "inside halo" in Pap-stained cytology specimens, this feature may be added to the data base dictionary and the value that may be assigned thereto may be "absent", "occasional", "frequent" or "other". This newly-added feature will be added to previously created case records, but no value will be assigned thereto. However, since a value must be assigned to make a case record complete, even if it is "other" (e.g. not applicable to a particular case), the expert has the opportunity to edit those case records which he created previously so as to assign an appropriate value to this new feature.

Likewise, the feature of pleomorphism for cell orientation might have been observed by the expert in early cases resulting in the diagnosis of malignant mesthelioma. However, as the expert observes additional cases of malignant mesthelioma, he might find that this feature is relatively unimportant and has little, if any, bearing on the ultimate diagnosis. The expert may delete this feature of pleomorphism for cell orientation from the knowledge base dictionary, thereby deleting this feature and its value from all case records. Thus, features may be added to or deleted from the knowledge base, resulting in the addition or deletion of those features from previously created case records. It will be understood that each case record contains all of the features created for the dictionary, even if the value of a particular feature in a given case is "not applicable".

Notwithstanding the characterization of a feature as being discrete or continuous, the feature also may be visually observable (although some, such as age, sex and several other clinical features will not). For example, most of the features included in the category "general cell morphology" are visual features. Examples of these include the size and shape of the cell and of the nucleus, as well as pleomorphic size and shape. Similarly, the features included in the category of Pap-cytoplasmic morphology the features included in the category of cell block histochemical stains also generally are visual features. Such visual features in a specimen being examined are displayed on monitor 106 after being imaged onto video camera 116 by microscope 114. As is known by those of ordinary skill in the art, the operating system used with processor 102 is such that display 106 may be controlled as to provide textual information in one portion of the display and pictorial information in another. Thus, while the expert is viewing a specimen, the various features which characterize that specimen may be selected from the knowledge base dictionary and the appropriate preestablished values may be assigned thereto. In the event that the dictionary does not contain an appropriate feature characterization, the expert may operate keyboard 108 to create a new feature, assign an appropriate value to that feature and enter that newly created feature into the knowledge base dictionary. Thus, various characteristics that are observed in the displayed image are suitably identified by designating those characteristics as particular features retrieved from the knowledge base and by assigning proper values from the knowledge base to those designated features.

A graphics application program is included in the overall software of processor 102. This graphics application program is adapted to display various signals, referred to as "overlays", which the expert may select and position on display 106 so as to particularly point out or highlight particular features or other characteristics of a displayed pictorial image. This graphics application program is similar to a commercially available program designed for Apple and MacIntosh microcomputers and known as "MacPaint". Like the "MacPaint" gaphics aplilication system, mouse 110 is controlled to superimpose a cursor over a desired overlay symbol, select that symbol for use, and then reposition the cursor with the overlay symbol "attached" thereto to any desired location on the display screen. The final, desired position of the overlay symbol is identified by, for example, its position on the display screen, that is, its pixel location, and this location data together with overlay identification data are stored as part of the case record. When the pictorial image for which this overlay had been created subsequently is read from optical disk 112 and displayed on monitor 106, the overlay data linked to this image is read from magnetic disk 104 and is superimposed onto the displayed pictorial image. Thus, overlays may be created and positioned to illustrate particular features or other characteristics during subsequent displays of that image.

As mentioned above, optical disk drive 112 is known as a WORM drive and, thus, a pictorial image derived from video camera 116 and displayed on monitor 106 may be written onto the optical disk. Typically, this pictorial image is included in a case record and identification data is recorded in the case record to identify the location on the optical disk of that pictorial image. Hence, the pictorial images are linked to the case record to permit quick and easy retrieval and display.

As may be expected, two or more pictorial images may be linked to a particular case record. One type of feature may best be illustrated in one pictorial image, whereas a different feature might be present in a different image. Usually, the different images associated with the same case record are sufficiently distinct as to be quickly recognized by the expert. Because of this ready distinction among the images, only a small amount of data is needed to provide a rough or approximate display of each image. Accordingly, each case record stored on magnetic disk 104 and to which one or more pictorial images stored on optical disk 112 are linked includes image data which, when read from the magnetic disk, results in the display of the aforementioned rough or approximate images. These approximate images are displayed in relatively reduced size and are referred to herein as "icons", each icon corresponding to a pictorial image stored on optical disk 112. A desired icon may be selected, as by operating mouse 110 to position the cursor over the desired icon, causing processor 102 to read the corresponding pictorial image from optical disk 112 for display on monitor 106.

During his creation of a case record, the author is expected to identify those features which, in his opinion, are best illustrated in a displayed pictorial image. This may be achieved simply by linking the selected features to the displayed image, for example, by identifying in the case record the particular image (or images) in which the feature is illustrated. A feature may be linked to an image by designating a selected feature as a "visual" feature while a pictorial image is displayed. It is assumed that by selecting such a designated feature at the time that a pictorial image is displayed, the expert observes that feature in that image.

Of course, certain categories of features are not visual features. As an example, those features included in the category of "clinical features" typically are not visual. Examples of clinical features include the age and sex of a patient, whether the patient has been exposed to asbestos, whether the patient previously had a tumor and other selected diseases, and whether the patient has particular clinical symptoms (e.g. shortness of breath, pain, ascities or bowel obstruction). Nevertheless, such clinical features are selected and assigned values in the same manner as visual features are selected and valued.

Figures 2, 2A:
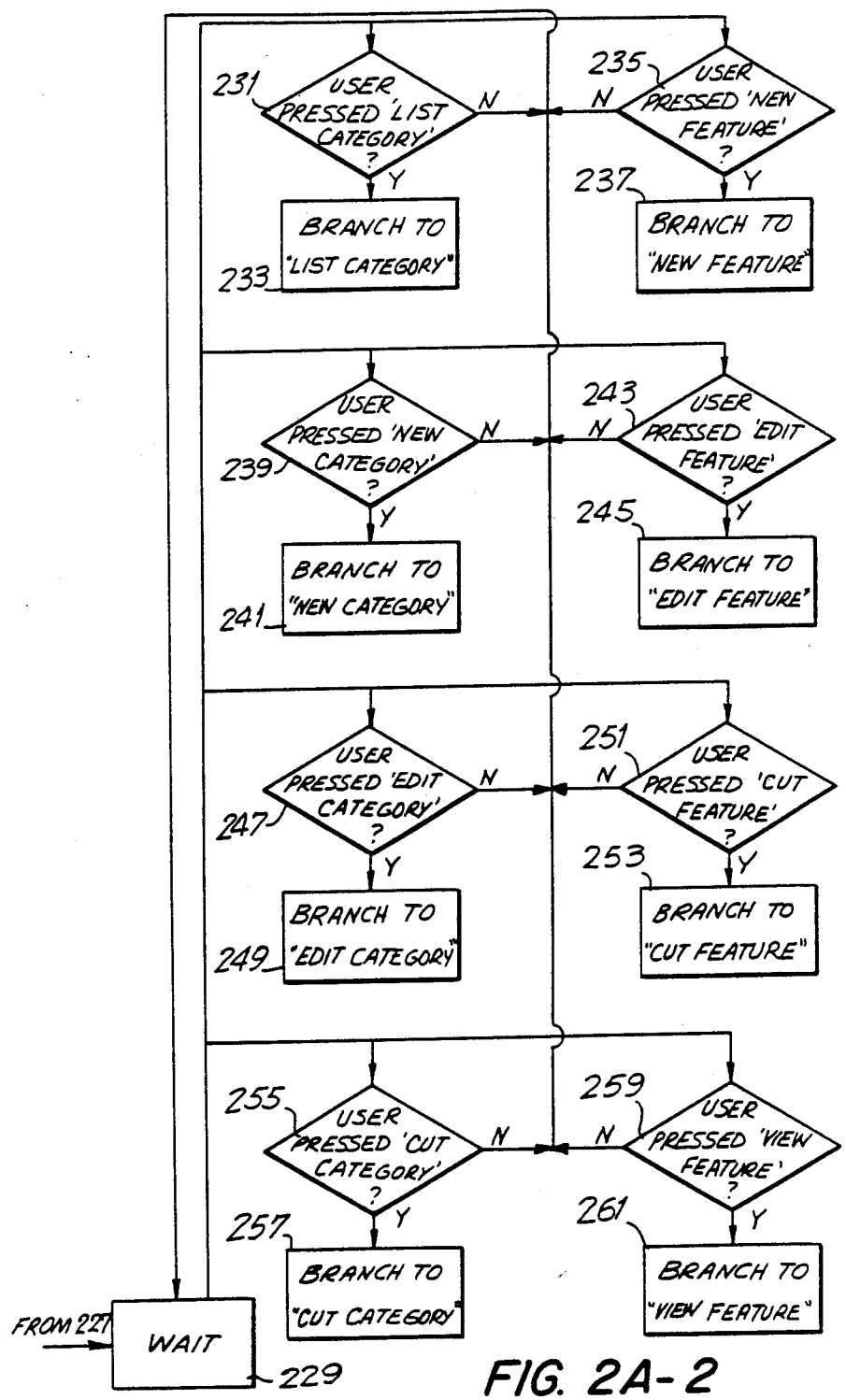

The manner in which system 100 is used interactively by an expert to craft a knowledge base of case records comprised of features now will be described in conjunction with the various display screens presented on monitor 106. The manner in which those screens are generated by processor 102 and the manner in which the processor responds to the operation of keyboard 108 and to mouse 110 by the expert also will be described. Referring first to FIG. 2, there is illustrated a basic display screen 200, referred to herein as the "home" screen. The operating and applications programs of processor 102 causes monitor 106 to display this home screen which is comprised generally of a case window 202 and a feature window 220. Those of ordinary skill in the art will understand what is meant by reference to "windows" in the environment of a computer.

Case window 202 displays a case list 204 which identifies the case records stored in the data base. It is appreciated that only a limited number of case identifications may be displayed in case window 202; and this case list may be scrolled to display additional identifications. A suitable scroll "button" may be displayed (not shown) and activated by operating mouse 110 to position the cursor on this scroll button, whereafter the user simply operates one of the selector switches provided on the mouse. Such a scrolling feature and scroll button are conventional and further description thereof need not be provided. It should be noted here that the operating and applications systems cause monitor 106 to display discrete areas which are referred to as "buttons". When used with mouse 110, a button is activated simply by superimposing the cursor on a desired button and then activating a selector switch on the mouse. Alternatively, monitor 106 may be provided with a touch-sensitive screen which senses a user's finger in contact with the location of a displayed button, whereupon that button is activated. As a further alternative, keyboard 108 may be operated to position the cursor at a desired button and to activate that button. As yet another alternative, various keys on keyboard 108 may be associated with respective buttons such that the actuation of a key correspondingly activates that button. As yet another alternative, system 100 may be provided with a light pen which the user may juxtapose opposite a desired button and thereby actuate that button. It will be appreciated that other input devices may be used in cooperation with the various display screens to be described for the purpose of entering data and interacting with the displayed information. For simplification, mouse 110 and keyboard 108 are described as such input devices.

A case 206 selected by the expert and included in the displayed case list 204 is highlighted to identify that it has been selected. In the absence of any deliberate selection by the expert, a so-called default case identification, such as the first case identified in case list 204, may be highlighted and, thus, selected.

Figure 18:
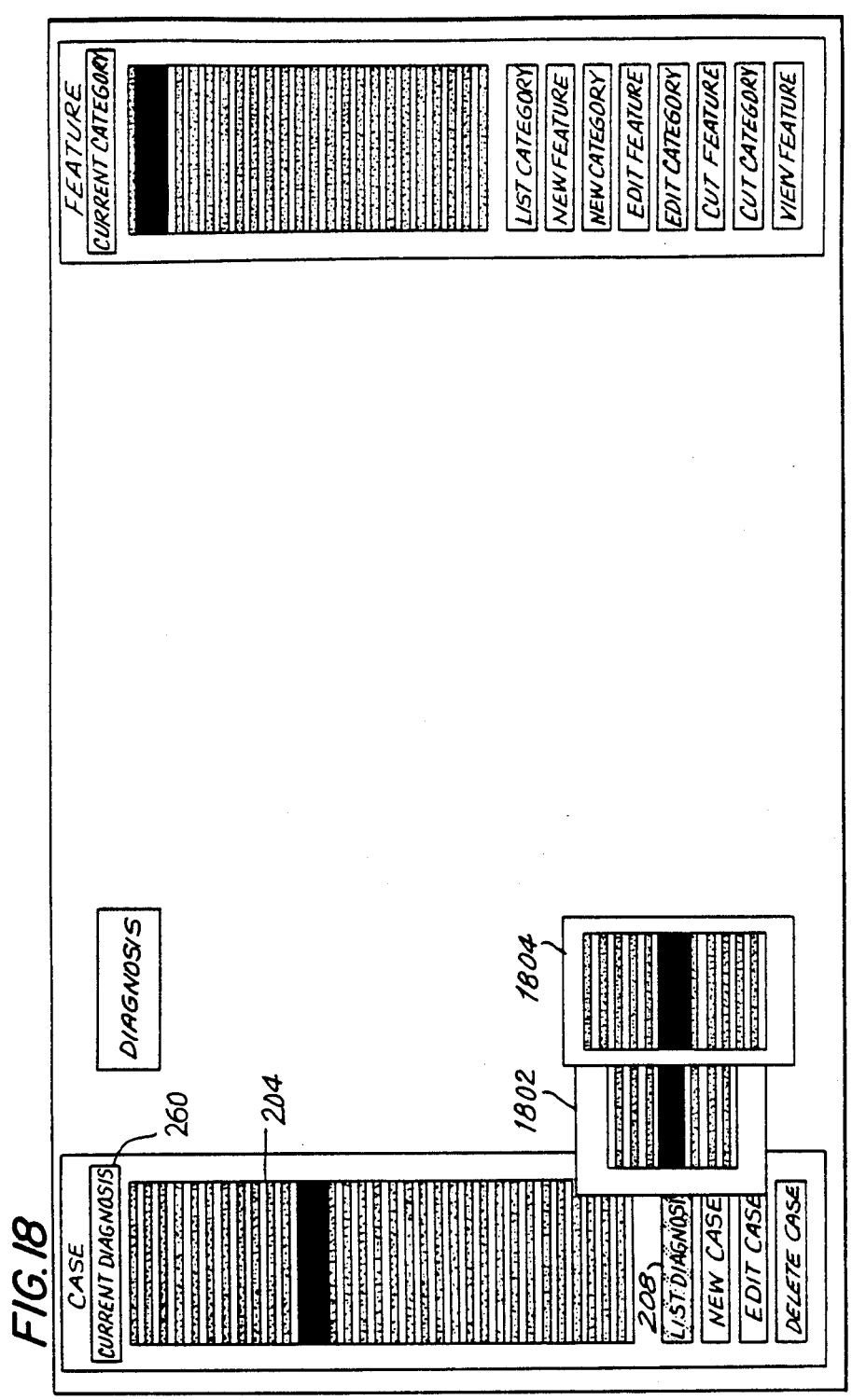
FIG. 18 is a display of diagnoses.

Case window 202 also displays a list diagnosis button 208, a new case button 210, an edit case button 212, and a delete (or cut) case button 214. Actuation of a respective button results in the operation or function so identified. For example, actuation of the list diagnosis button 208 results in a display on monitor 106 of a list of various diagnoses that have been entered into the knowledge base. Diagnoses are listed in a hierarchy, and the selection by the user of any diagnosis included in the displayed list results in a list of next lower level diagnoses, the selection of any one of which results in yet another list of a still lower level of diagnoses, and so on. These sequential levels of diagnoses indicate the dependence of a given diagnosis on the preceding higher levels of diagnoses. As shown in FIG. 18, these diagnoses lists are superimposed onto home screen 200 which remains as the "background".

Figure 19:
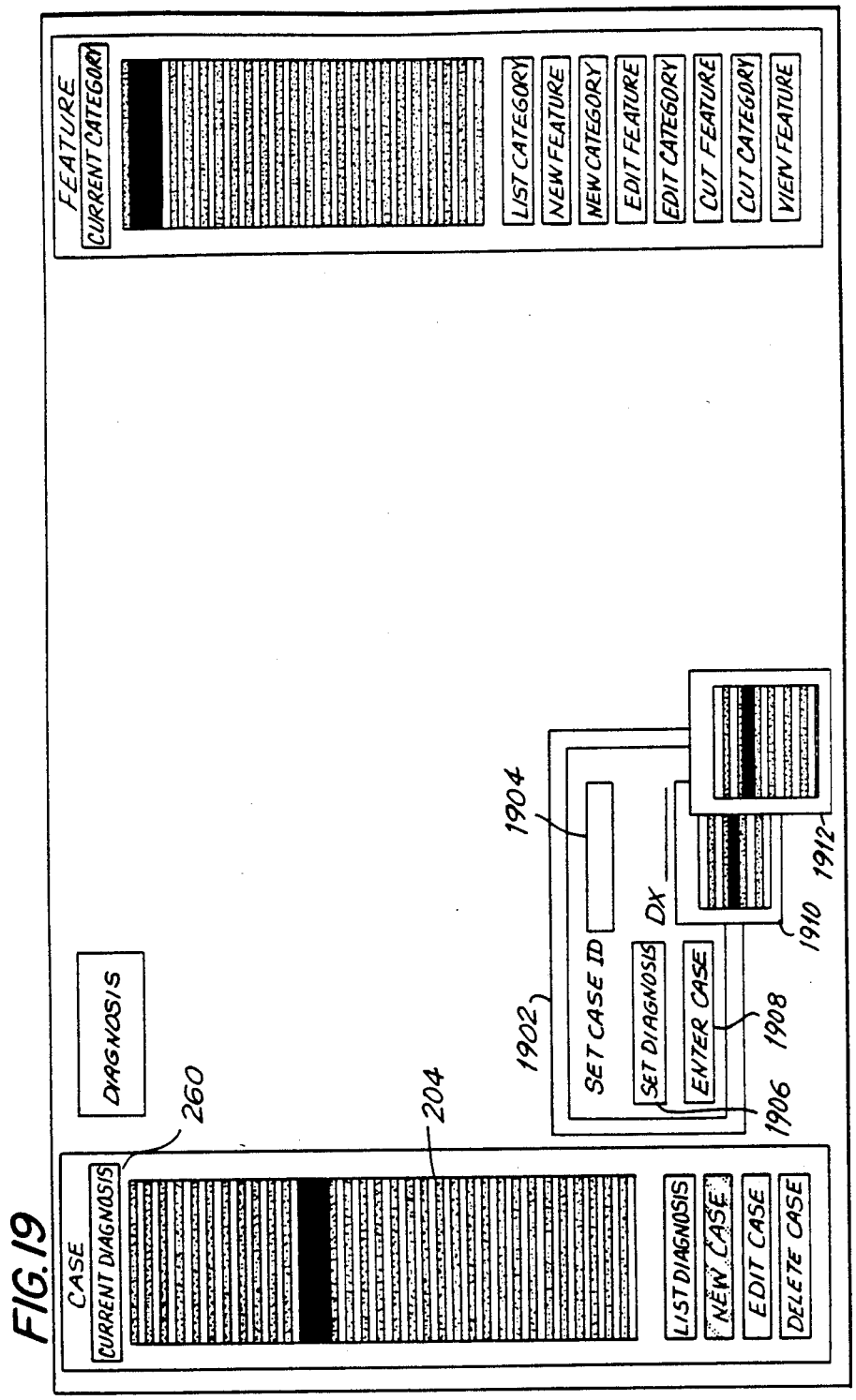
FIG. 19 is a display used when entering a new case into the data base.

New case button 210, when actuated, is used by the expert to create a new case. Data fields, referred to as "text input items", associated with basic case features are displayed and required the entry of particular values. For example, text input items requiring the entry of the case identification number and the particular diagnosis of this case are displayed, as described with reference to FIG. 19. Thus, the basis of the case record is created. Upon creation of a new case, the case identification number (or other suitable identification, such as a case name) is added to the case list and, typically, appears as the last item in that list.

Figure 20:
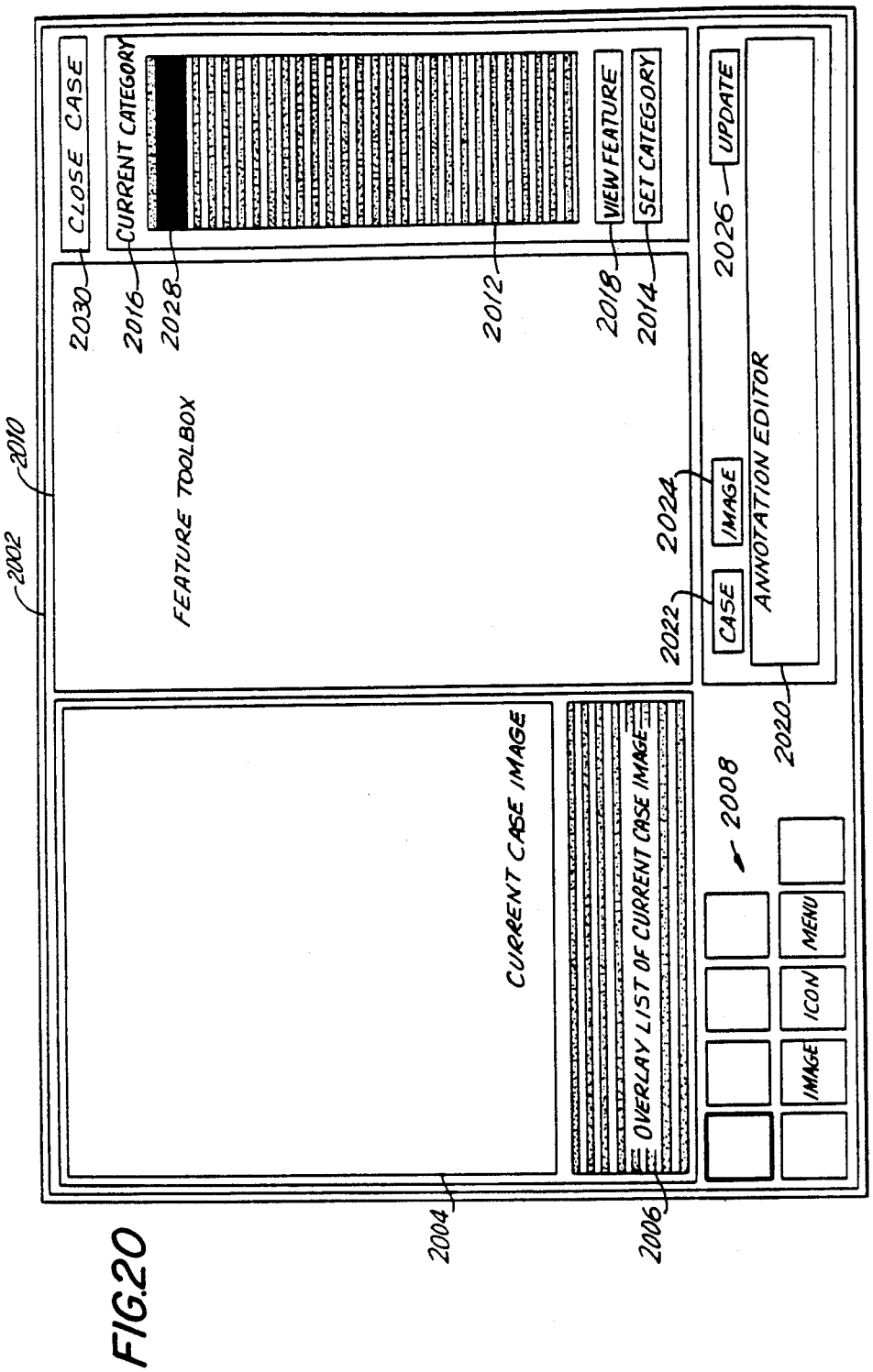
FIG. 20 is a display used when editing a case.

Actuation of the edit case button 212 retrieves from the knowledge base both the textual information and visual image information contained in the record of the particular case which is highlighted. (In a list of items, the one item which is highlighted is the "selected" item. Since the user has the choice of selecting any item in the list, the list is referred to as a choice of items, or simply a "choice".) Thus, actuation of edit case button 212 retrieves the case record of selected case 206. As a result, monitor 106 displays the icons of those pictorial images contained within the case record, as well as a more complete (i.e. magnified) pictorial image of the first icon, shown in FIG. 20. The icon of the displayed pictorial image is indicated, such as by highlighting the border of that icon; and a listing of those overlays which have been established for this pictorial image is provided. Additionally, a default category of features is indicated, as in selected category window 222 (also referred to as the current category message) of feature window 220 (to be described), and those features of the case (i.e. the case features) included in the indicated category are listed in feature list 224 (or feature choice). If the expert previously had annotated the case record with a text description, such as a description of why this case has been selected and what it represents, the annotation also is displayed.

Figure 21:
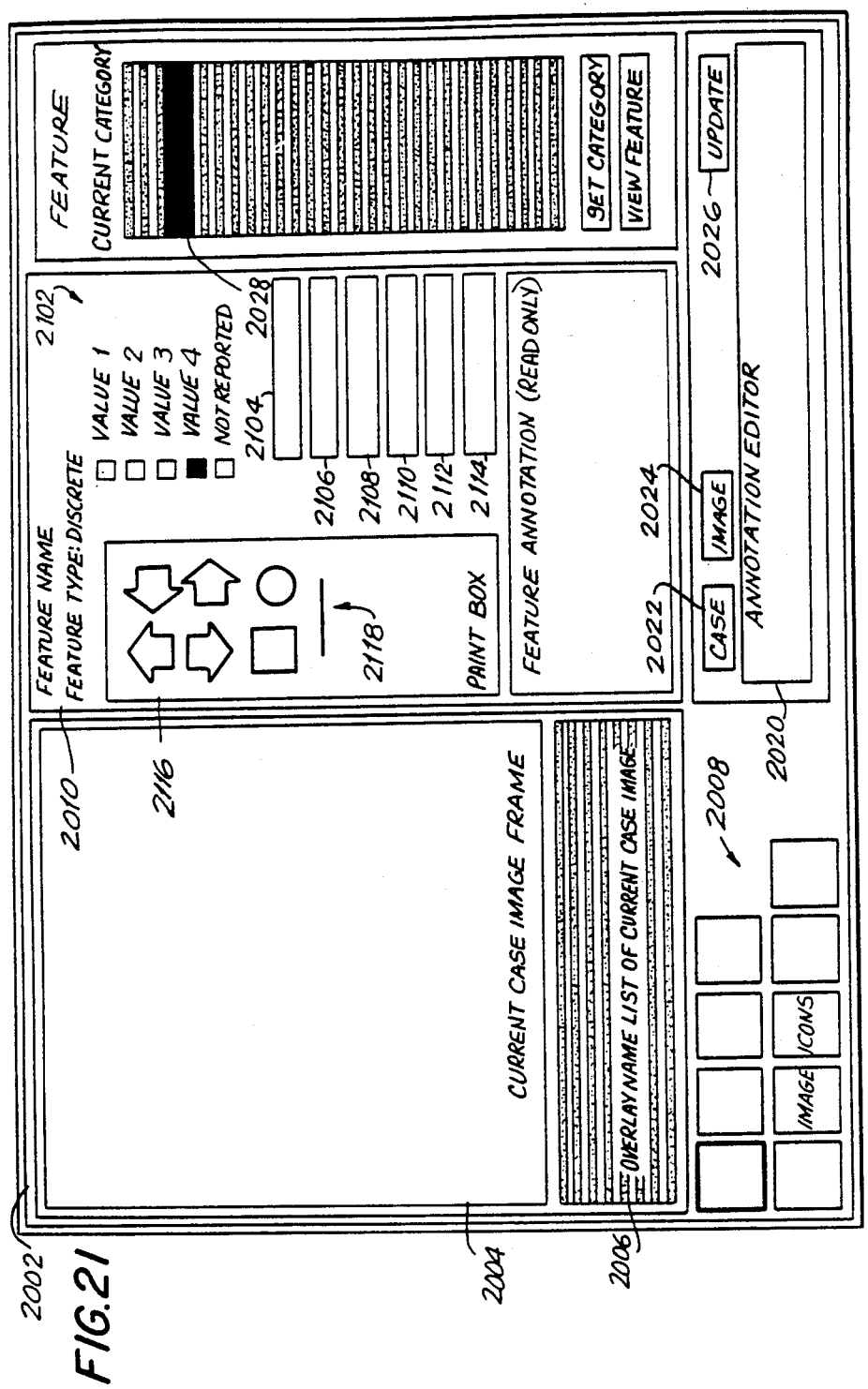
FIG. 21 is a display used in highlighting various viewable images of different features.
Figure 22:
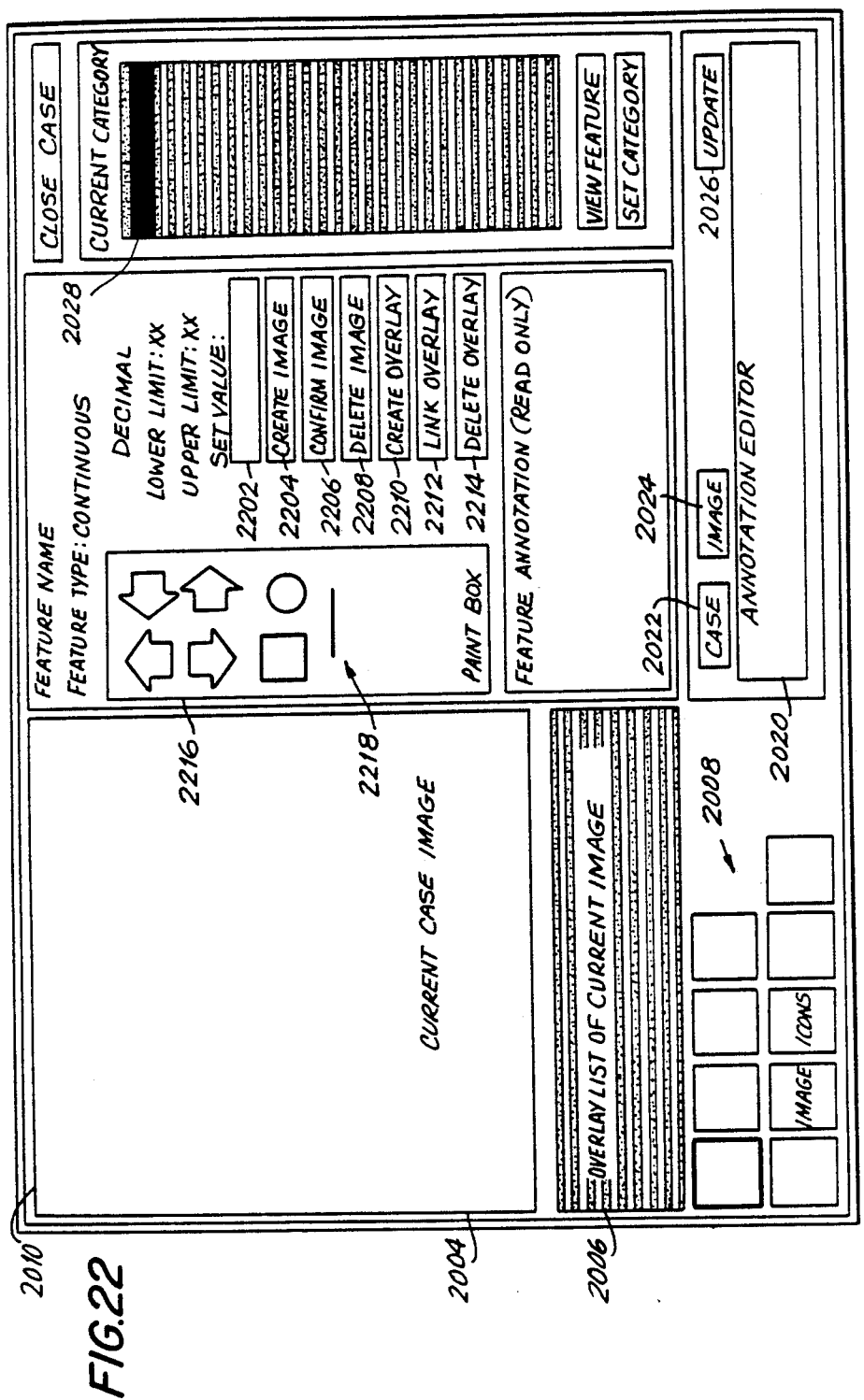
FIG. 22 is a display used in highlighting images of features having continuous values.
Figures 1, 22A:
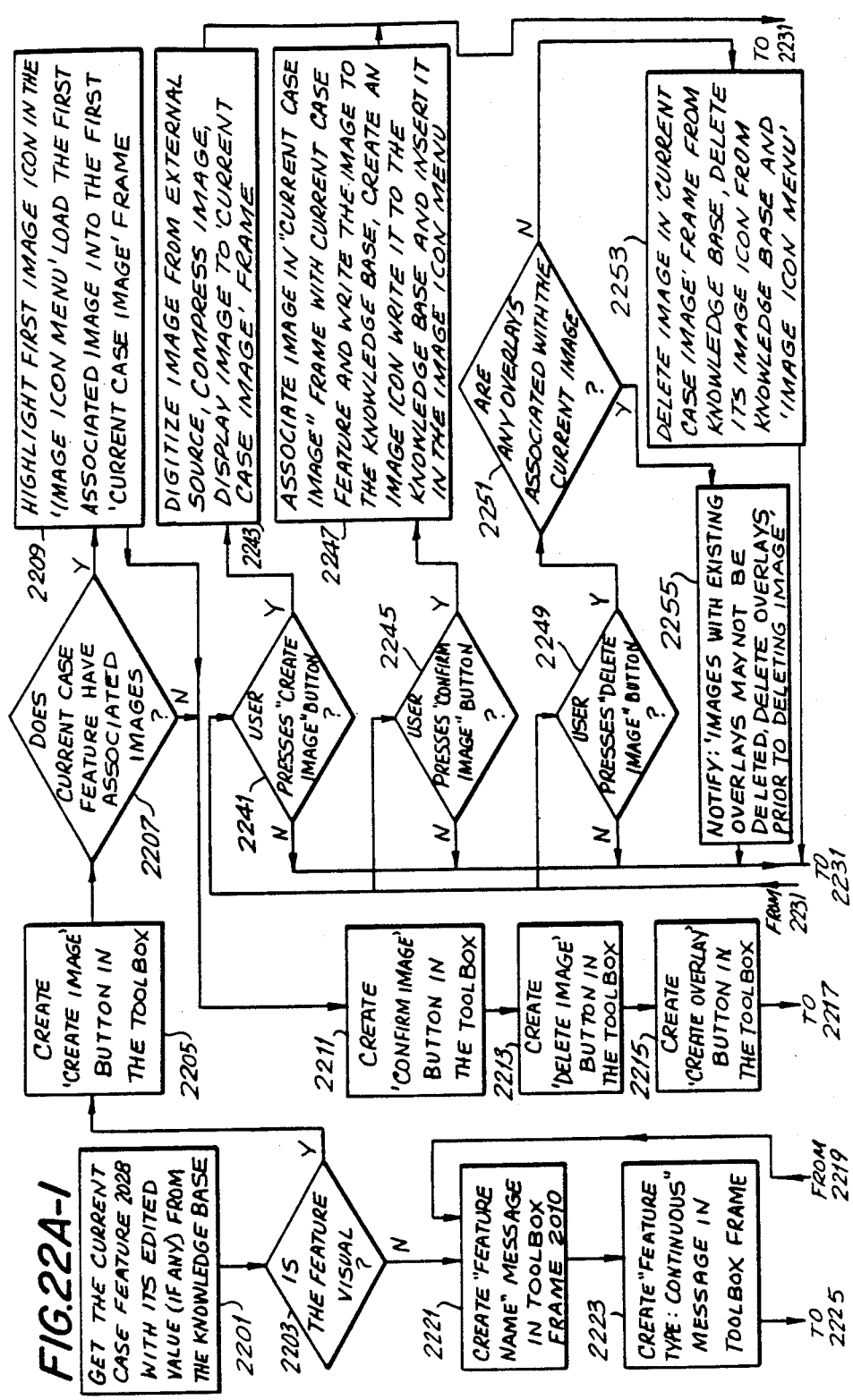
Figure 23A:
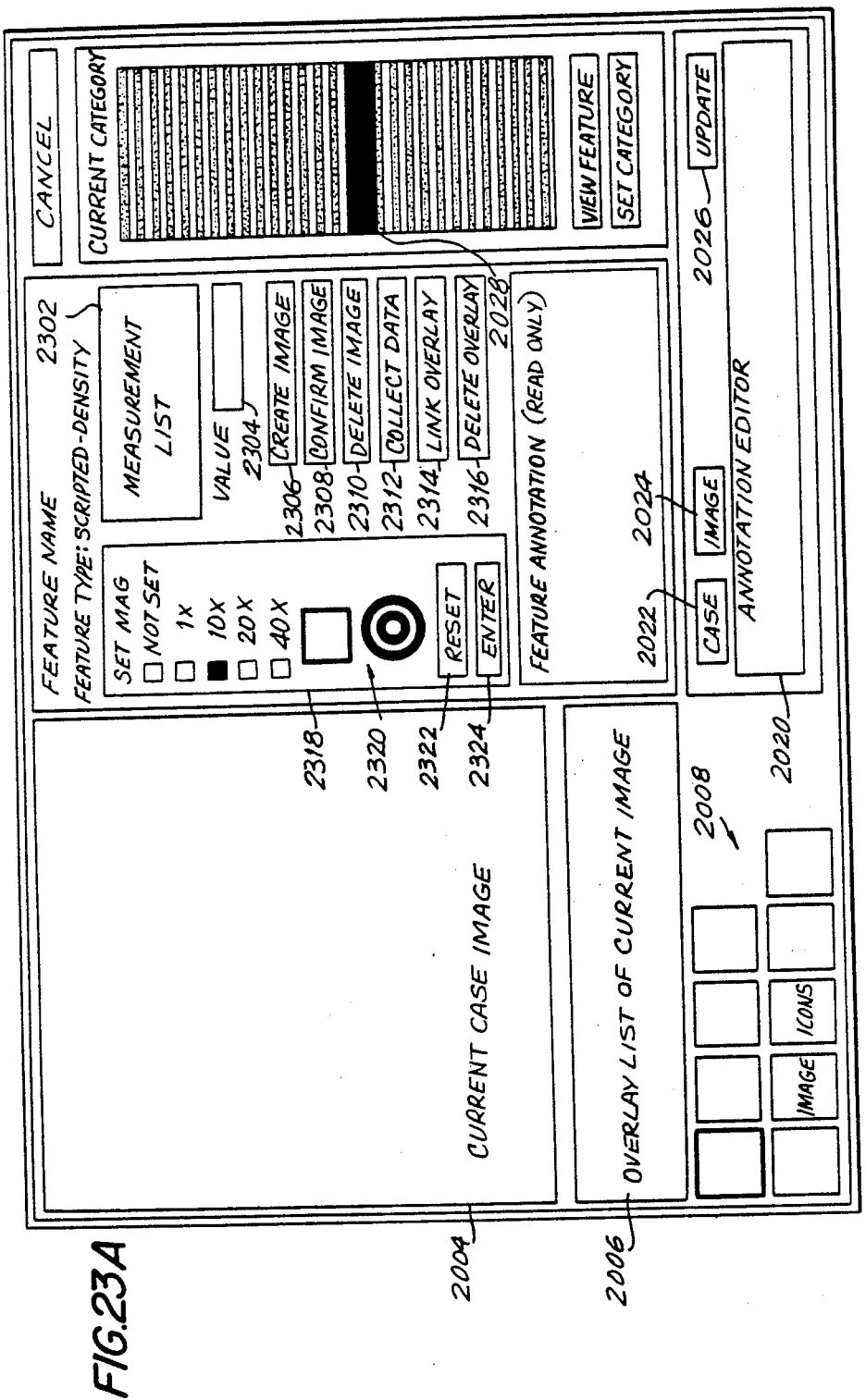
FIG. 23A is a display used in highlighting images of features having scripted values.
Figures 1, 23C:
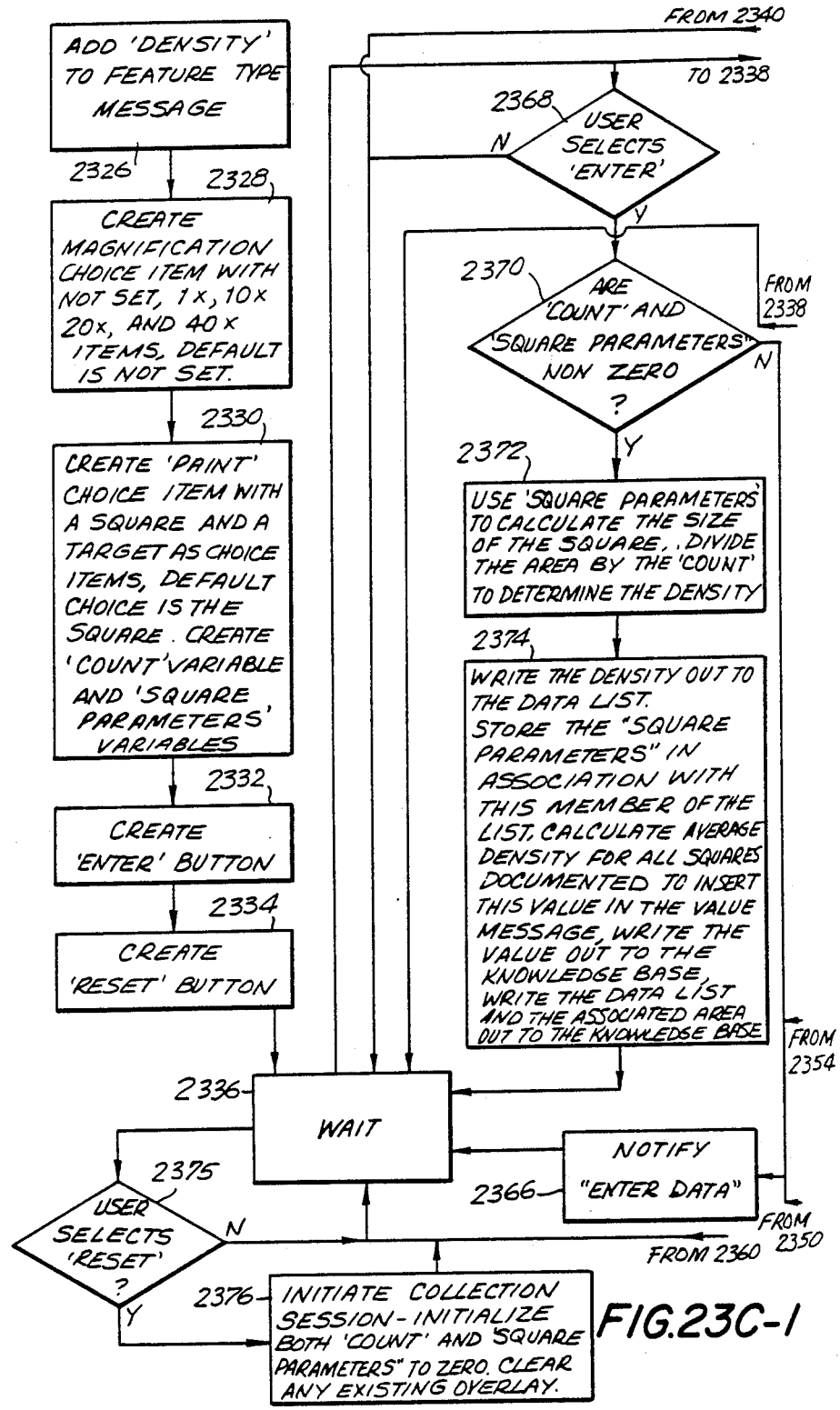
Figures 2, 23C:
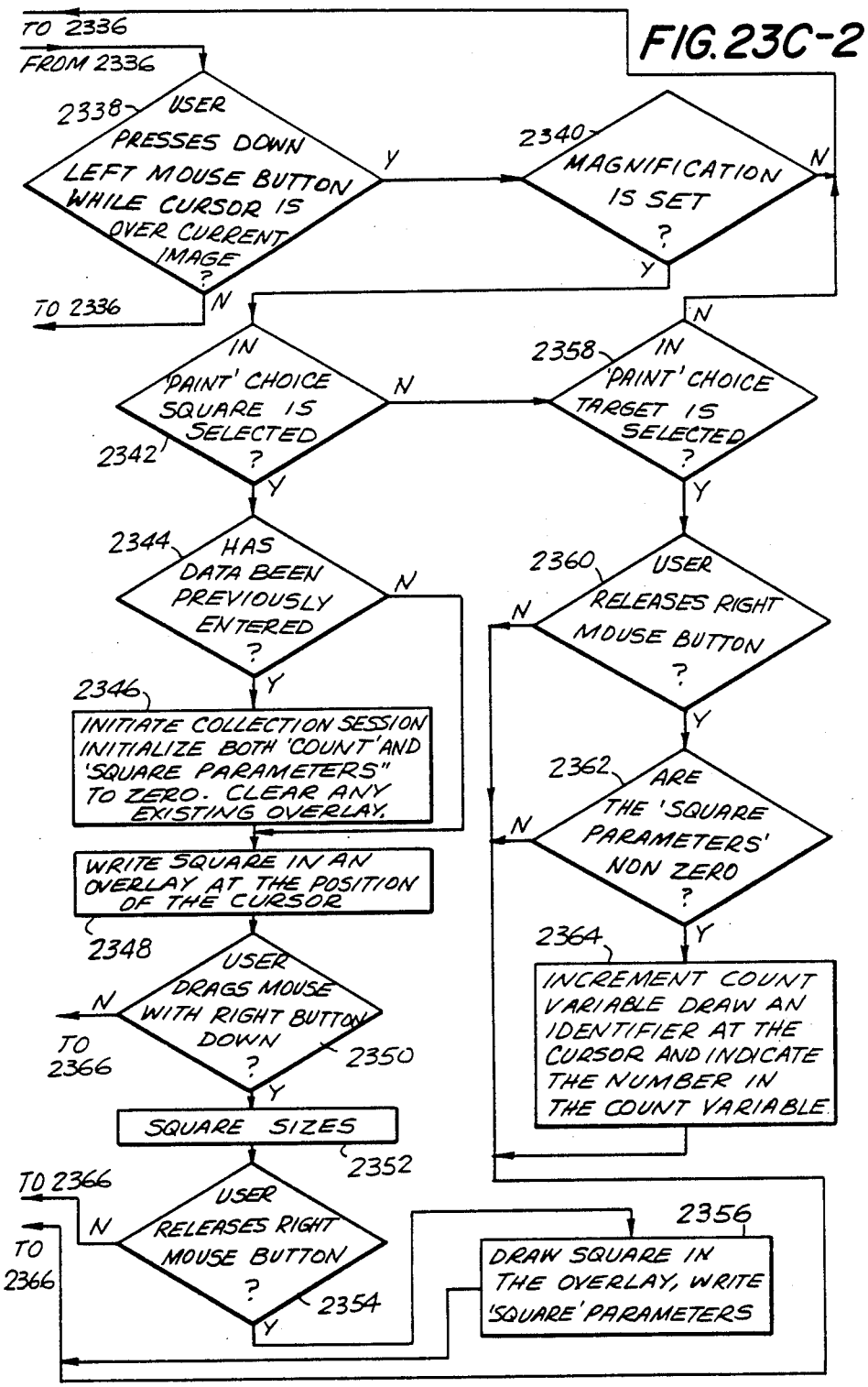
Figure 23D:
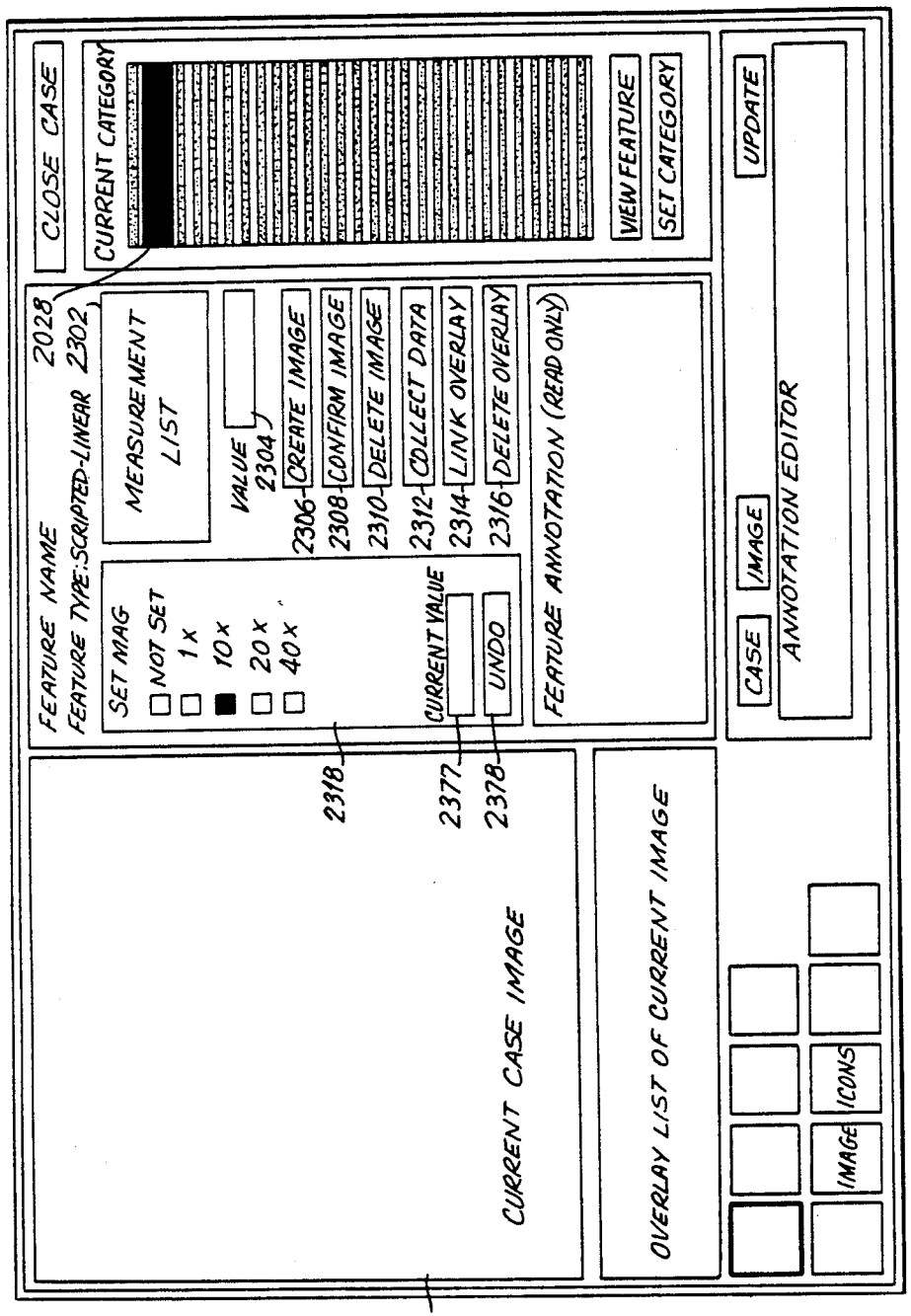
FIG. 23D is a display used in creating a list of parameters used to collect linear measurement data of displayed feature images.
Figures 2, 23E:
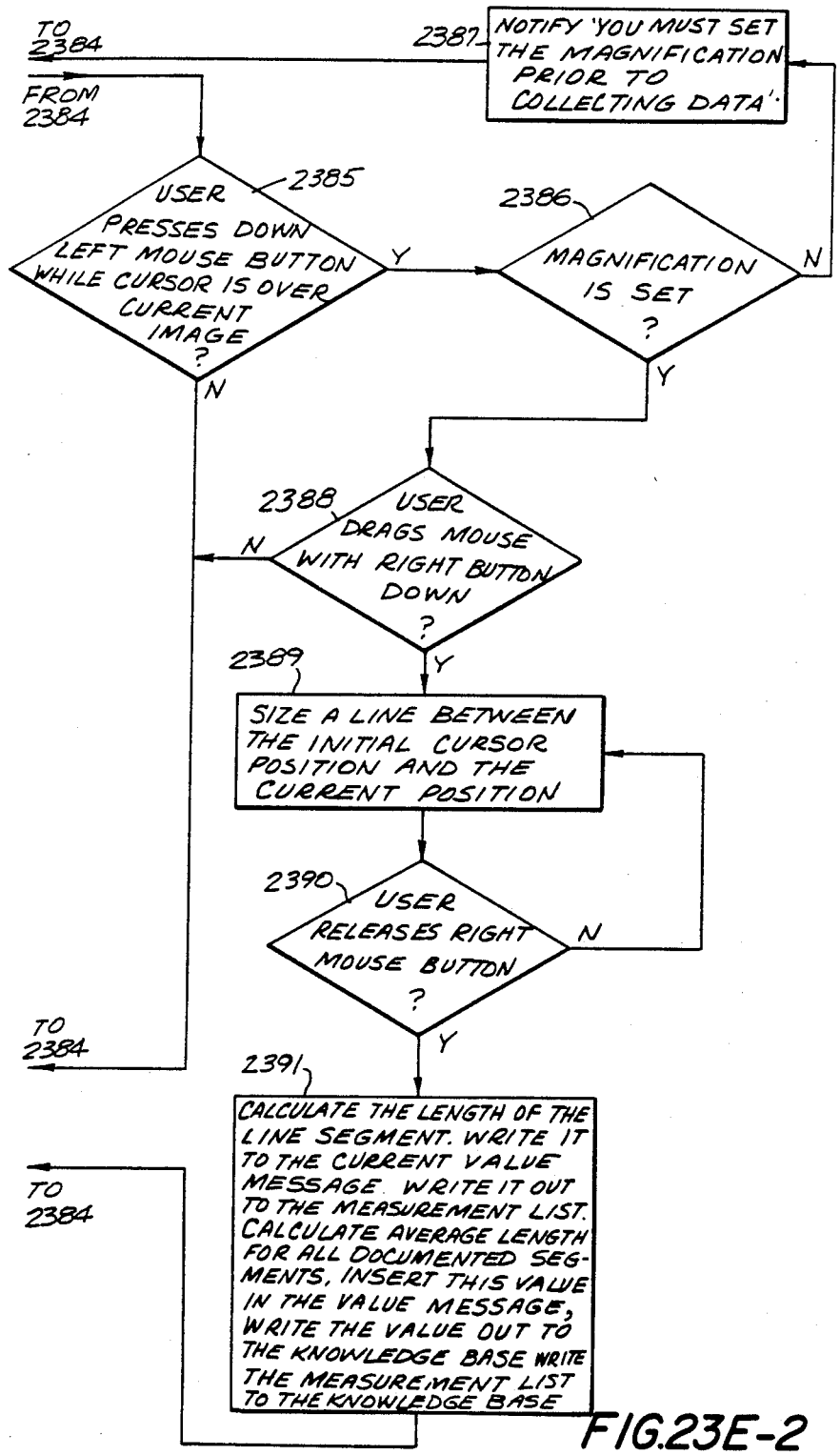
Figures 1, 23E:
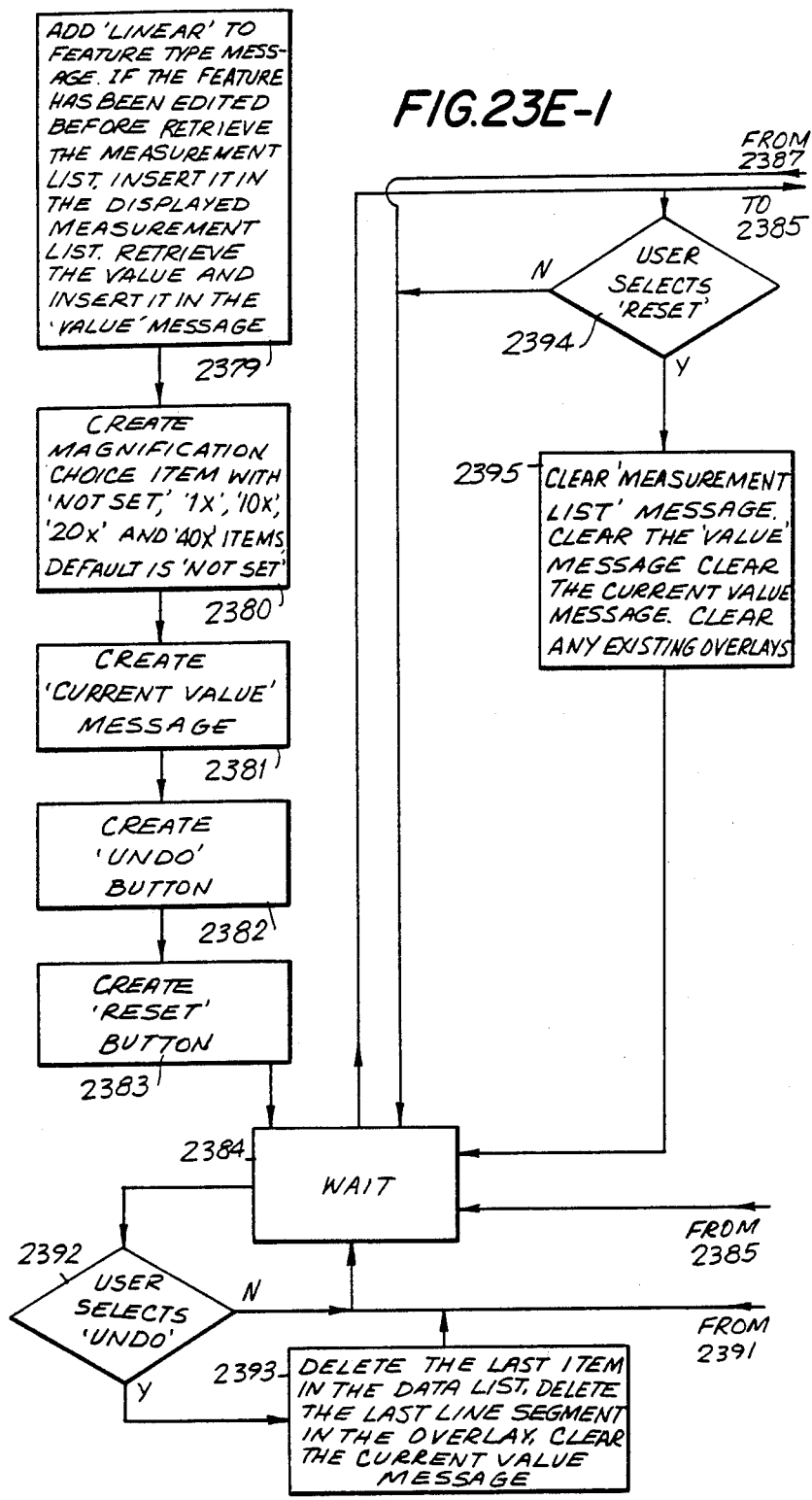
Figure 23F:
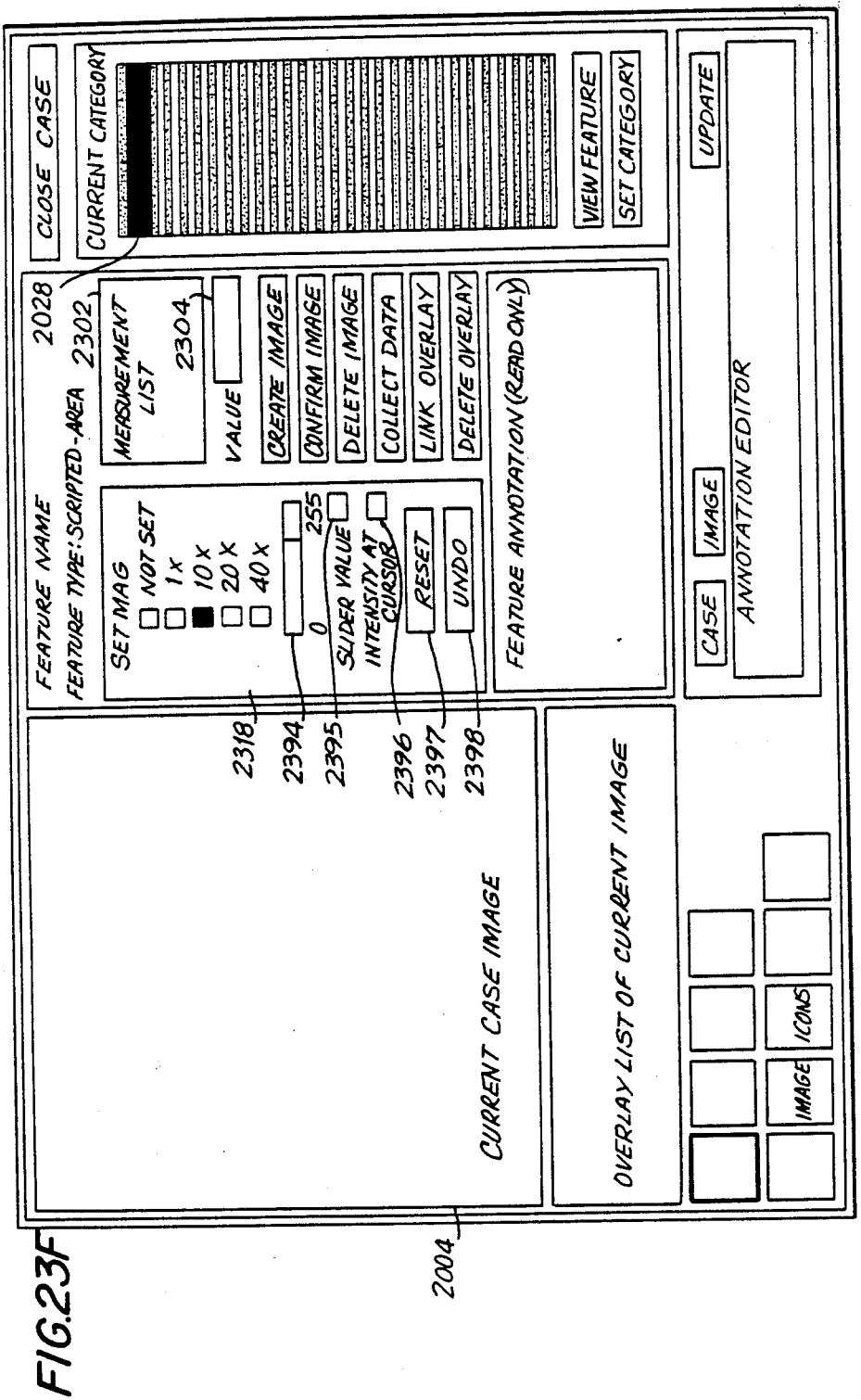
FIG. 23F is a display used in measuring displayed features having scripted values.
Figures 1, 23G:
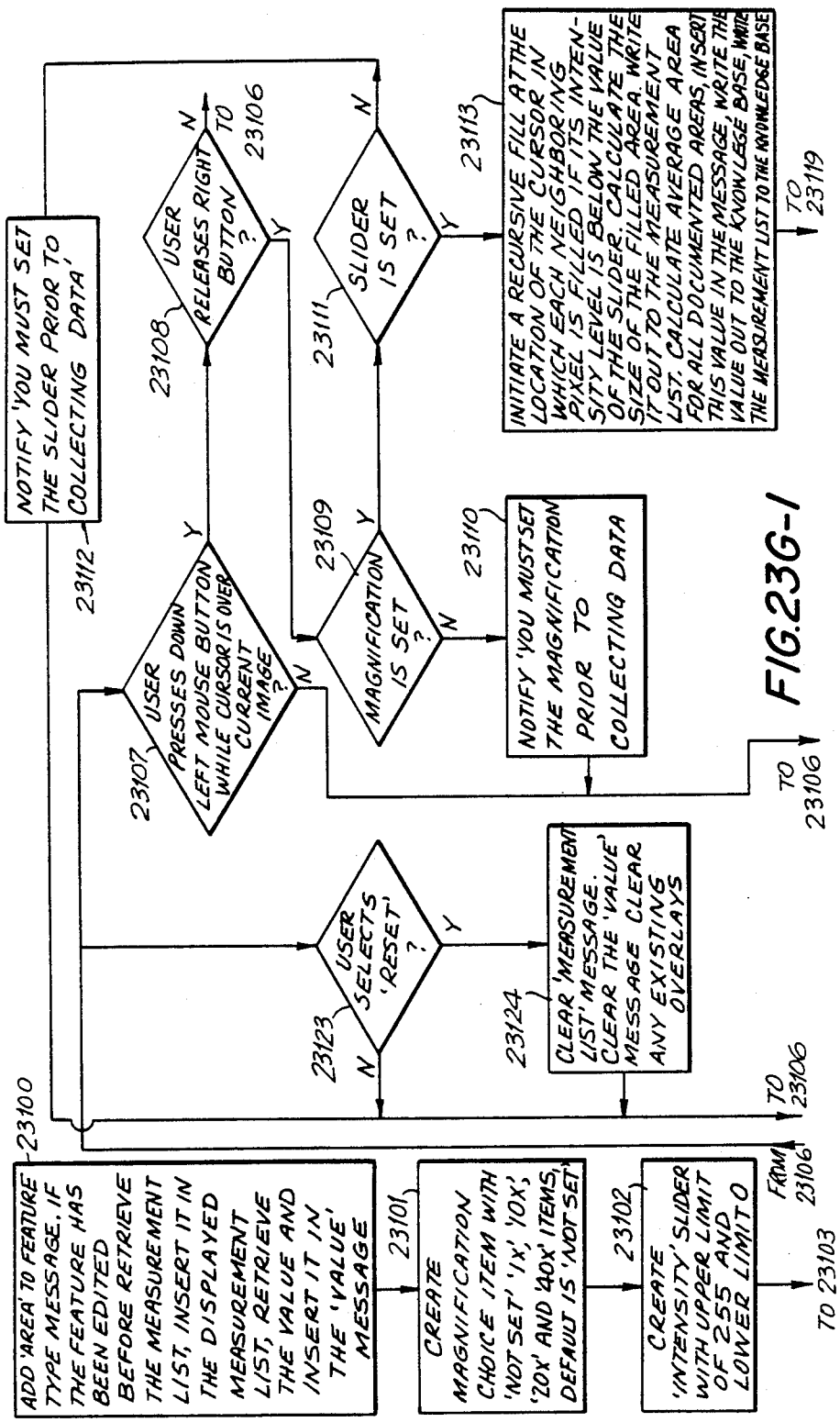
Figures 2, 23G:
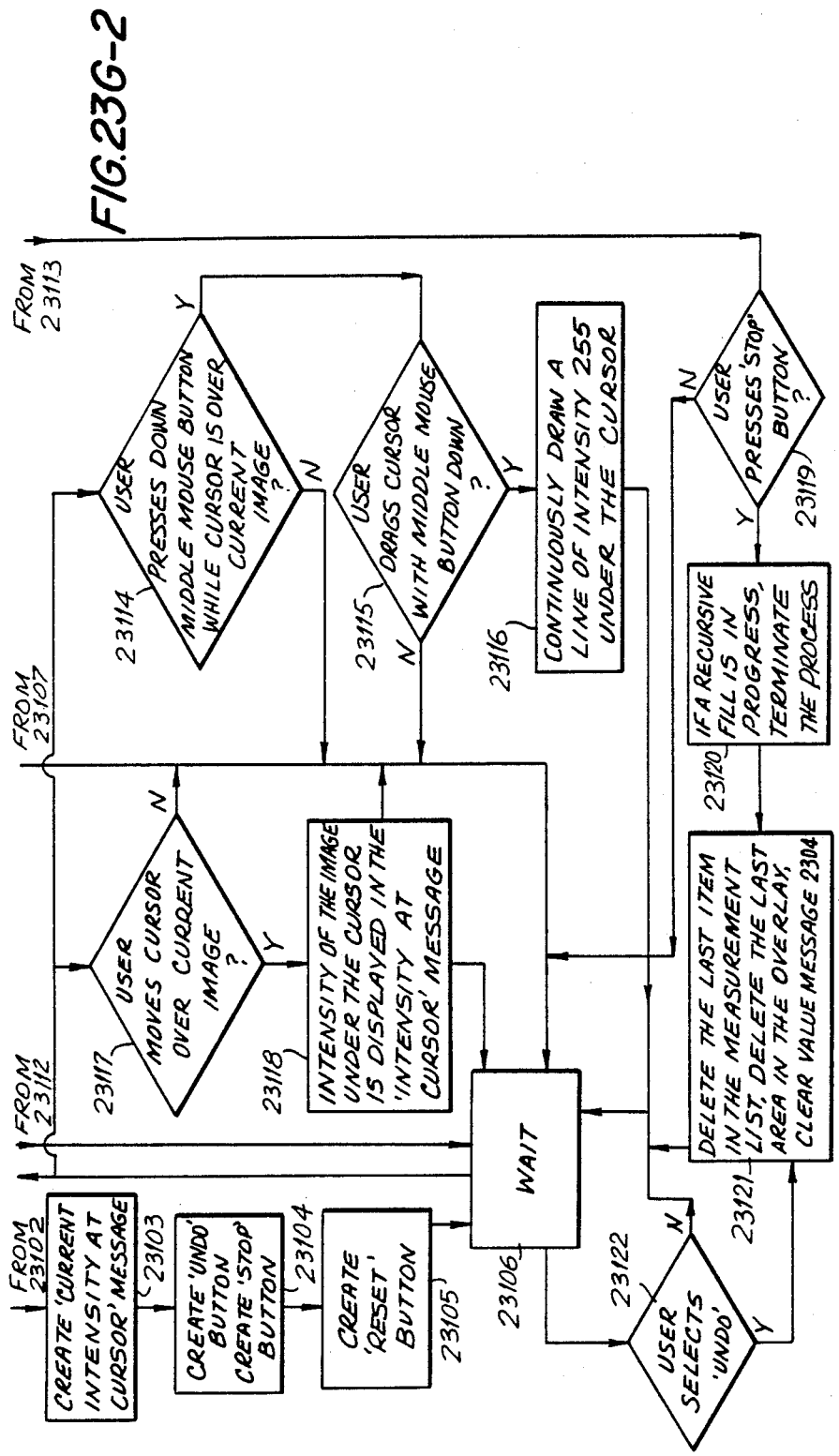

Actuating edit case button 212 establishes an edit case mode of operation, whereby the expert may create, alter, modify or add to the information contained in the case record. For example, if a new feature had been added to the dictionary, the value of this feature in the case record will appear as "not reported", and now may be assigned. This new feature may be illustrated in one or more pictorial images linked to this case and the expert may create and position overlays in those pictorial images. Thus, the edit case mode of operation, described more particularly in conjunction with FIGS. 21-23, permits refinement and the addition of further observations of features contained in that case and enables the expert to be consistent in his characterization of a feature from one case to another. Changes in the conditions of a patient and additional diagnoses of the patient's disease or diseases likewise may be documented in the edit case mode. Of course, if a new case record had just been created, as by the aforementioned actuation of new case button 210, the edit case function is used by the expert to value the features of that case; i.e. to document the case.

Figure 24:
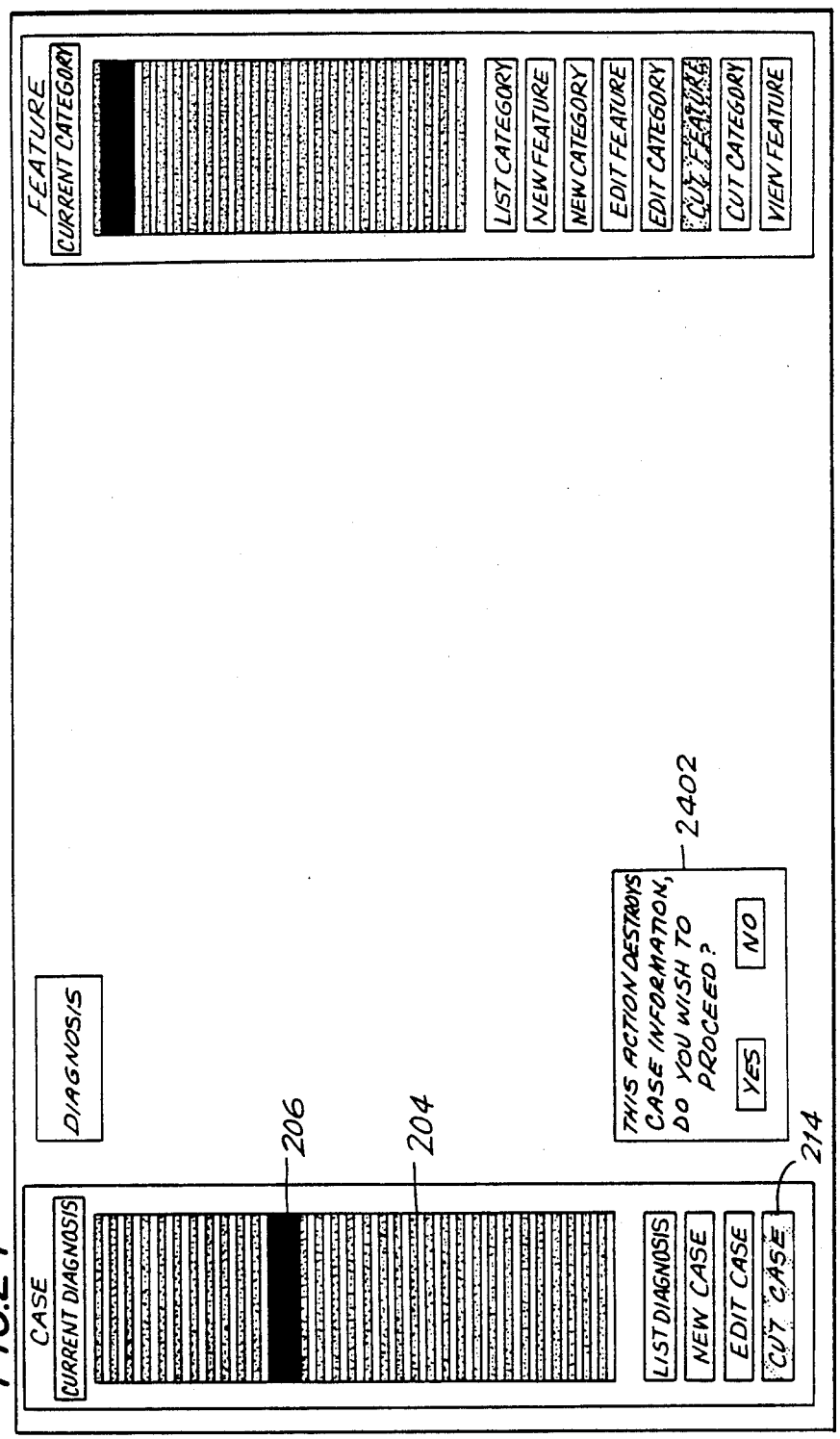
FIG. 24 is a display used to delete a case from the data base.

Actuation of the delete case button 214 simply deletes the record of the case which has been selected from the knowledge base. That is, the record of selected case 206 is effectively erased, as described in FIG. 24. The delete case mode may be useful if the expert discovers subsequent to the creation of the case record that his diagnosis was erroneous. Also, if the initial reasons relied upon by the expert to create that case no longer are valid, the delete case mode may be used to refine the overall knowledge base.

Home screen 200 also displays a feature window 220 which includes a selected category window 222 (also known as the current category message), a feature list (or choice) displayed 224 and various buttons 228-242. As mentioned above, for ease of classification and utilization of the various features included in the data base, unique sets of features are classified into respective categories. Examples of such categories include clinical features, Pap overview, cytoplasmic morphology, nuclear morphology, cell background, cell morphology, cell group features, immunoperoxidase and microscopic features. Preferably, an initial category, designated a default category, is displayed as the current category message 222, and the features included in the displayed category are listed in feature choice 224. The category indicated in current category message 222 may be changed, as by actuating the list categories button 228, described below, and those features included within the newly-selected category are displayed in feature choice 224.

Any one of the features identified in feature choice 224 may be selected for further processing, as will be described. The selected feature is highlighted, as represented by selected feature 226. In one embodiment, when a new feature list 224 is displayed, the first feature in that list is highlighted and is designated the selected feature. If desired, any other default feature may be designated the selected feature. Although the feature list may be displayed without a default feature, it is preferred, to avoid errors, to designate one of those displayed features as the selected feature even if the expert has not intentionally done so.

The buttons included in feature window 220 include a list categories button 228, a new feature button 230, a new category button 232, an edit feature button 234, an edit category button 236, a view feature button 238, a cut feature button 240 and a cut category button 242. These buttons may be actuated in the manner described above with reference to buttons 208-214 to establish operating modes or functions represented by those buttons. In one embodiment, the actuation of list categories button 228 superimposes a window, or frame, in which all of the categories included in the dictionary of the data base are listed. This is shown more particularly in FIG. 3. Selection of any one of the listed categories is indicated in current category message 222; and the features included in the selected category are displayed in feature choice 224.

The actuation of new feature button 230 results in the display of a create feature frame (discussed below with reference to FIGS. 6-9) with a text input item requesting the entry of a data field to identify the new feature which the expert wishes to create. Since this feature is created for the category indicated in message 222, the newly created feature is added to feature list 224, preferably immediately following selected feature 226, where ever that selected feature may be.

Figure 4A:
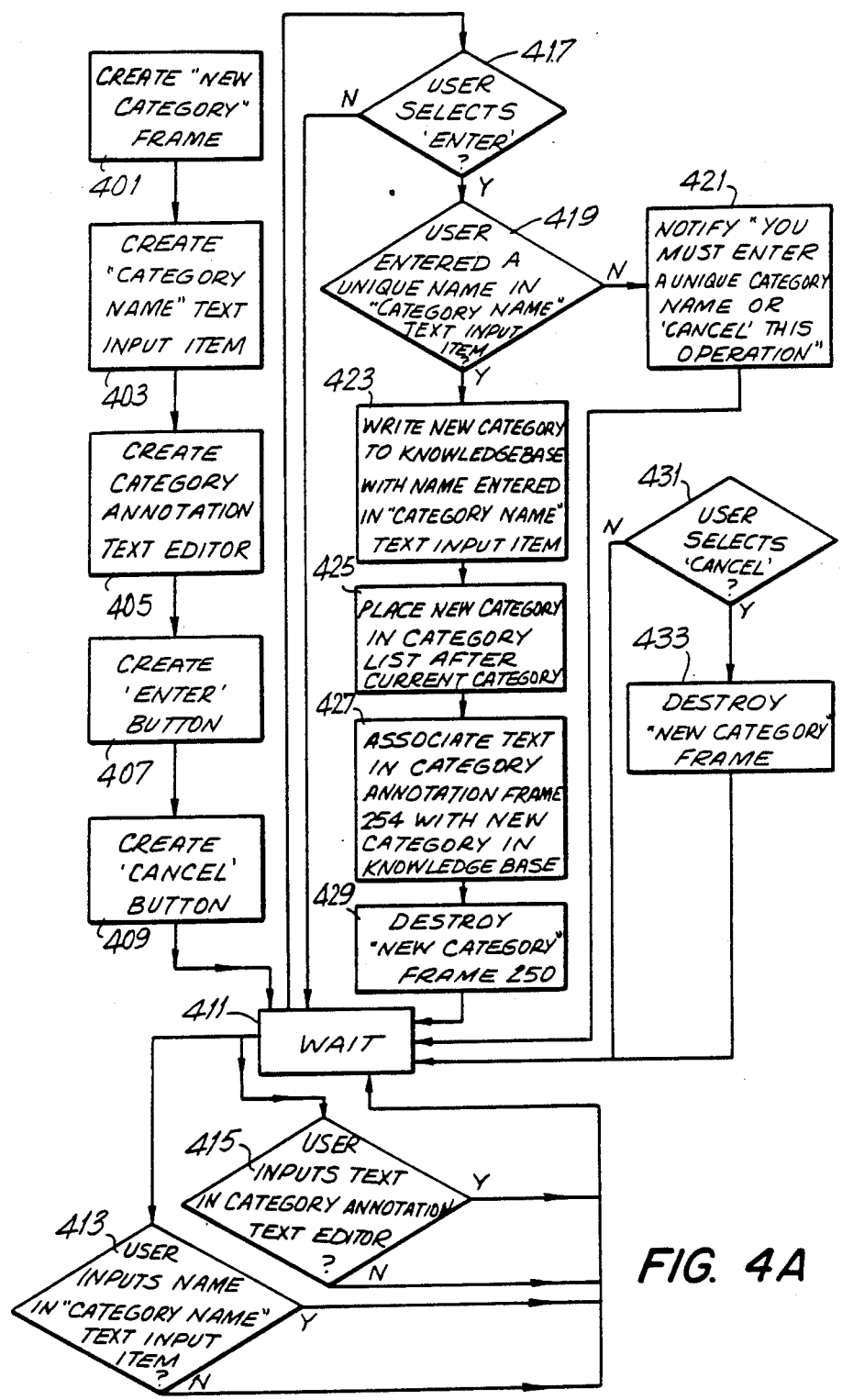
FIG. 4A is a flow chart representing the manner in which a new category is created.

The actuation of new category button 232 results in the display of a new category window (described below with reference to FIG. 4) having text input items which request the entry of data in particular data fields by which the new category may be identified and described.

It will be appreciated that newly created features and categories are added to the knowledge base dictionary and to the case records included in the knowledge base. Typically, the creation of a new category is accompanied by the creation of new features included in that category and is used by the expert to provide a basis for documenting a case and also to further refine the various case records included in the knowledge base.

Figure 10:
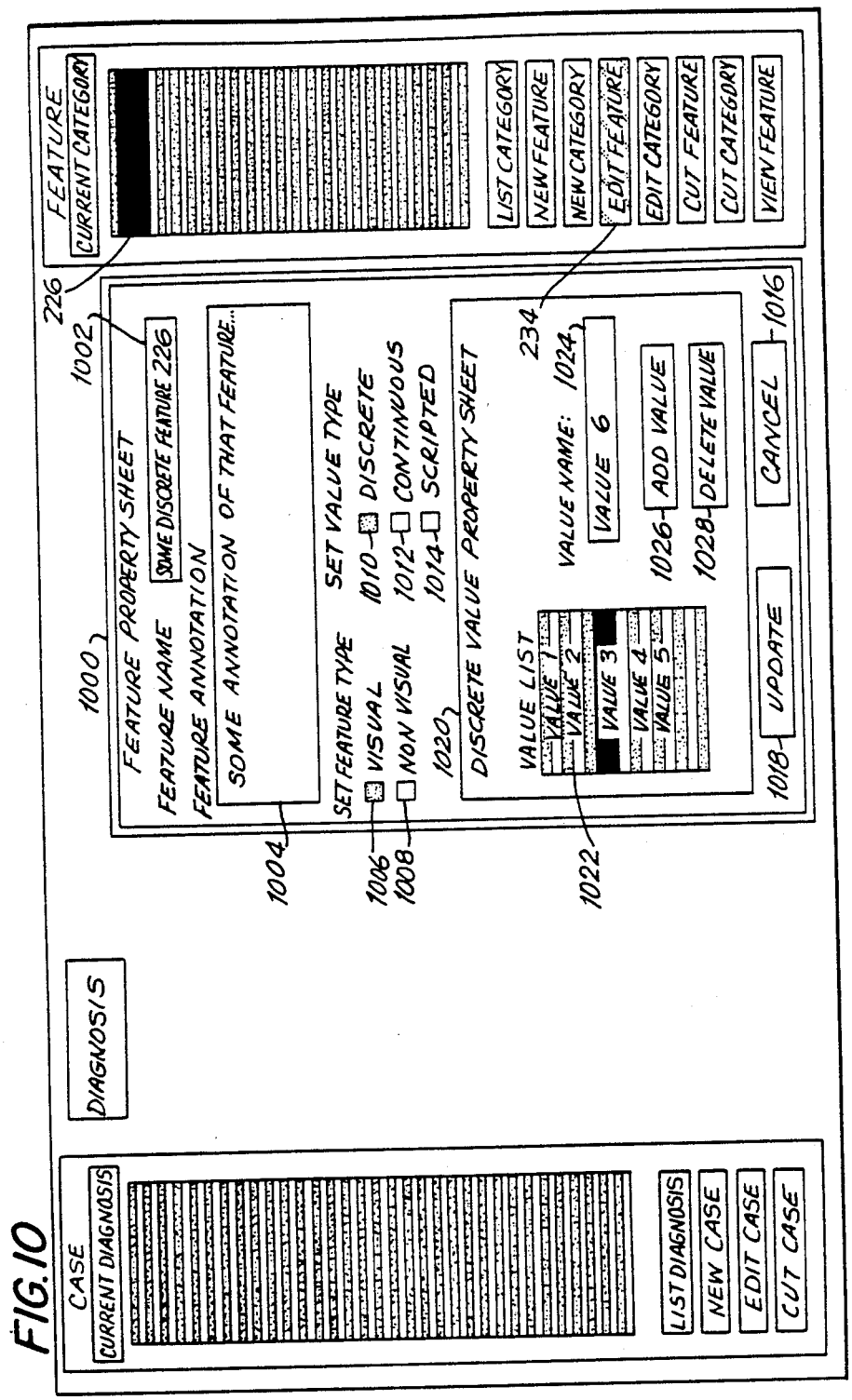
FIG. 10 is a display used when editing a feature having a discrete value.
Figure 11:
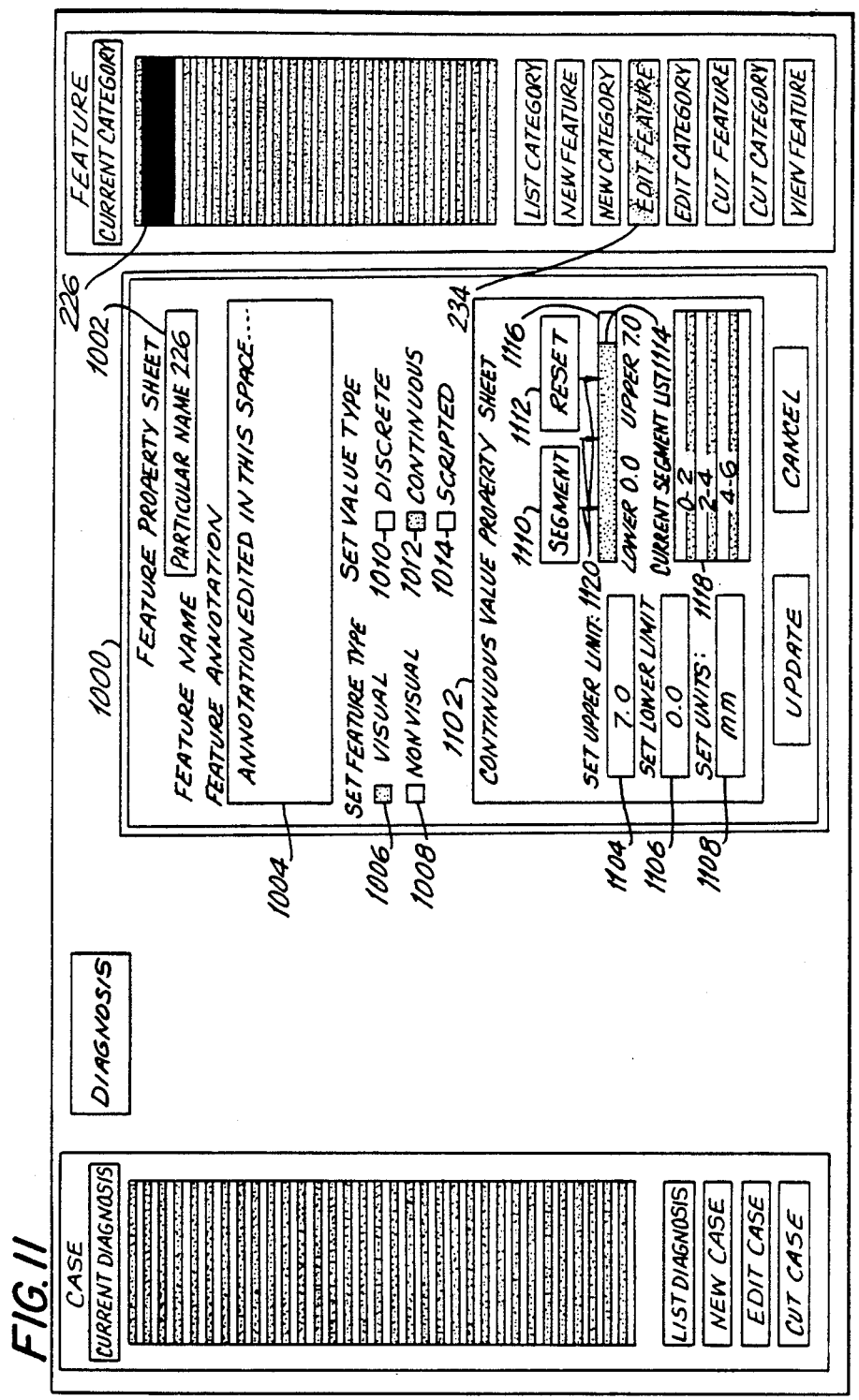
FIG. 11 illustrates a display used in editing a feature having a continuous value.
Figure 12:
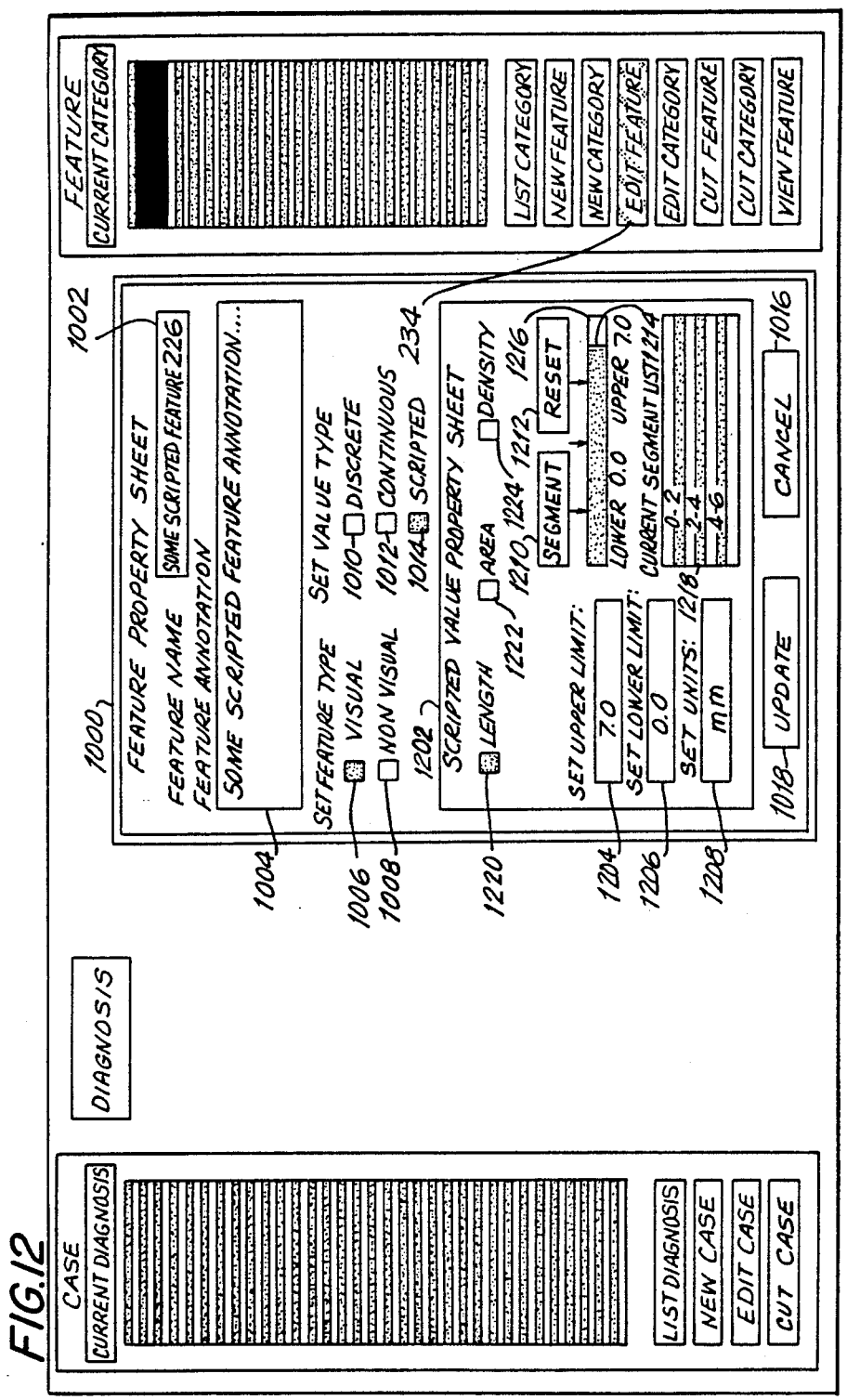
FIG. 12 is a display used in editing a feature having a scripted value.

The actuation of edit feature button 234 causes monitor 106 to display an edit feature frame (described more particularly with reference to FIGS. 10-12) which identifies the selected feature 226, identifies its type (i.e. whether it is a discrete, continuous or scripted feature) and identifies whether it is a visual feature. The list of possible values for this feature, which is retrieved from the knowledge base, may be modified by adding or deleting values, as will be described.

Figure 5:
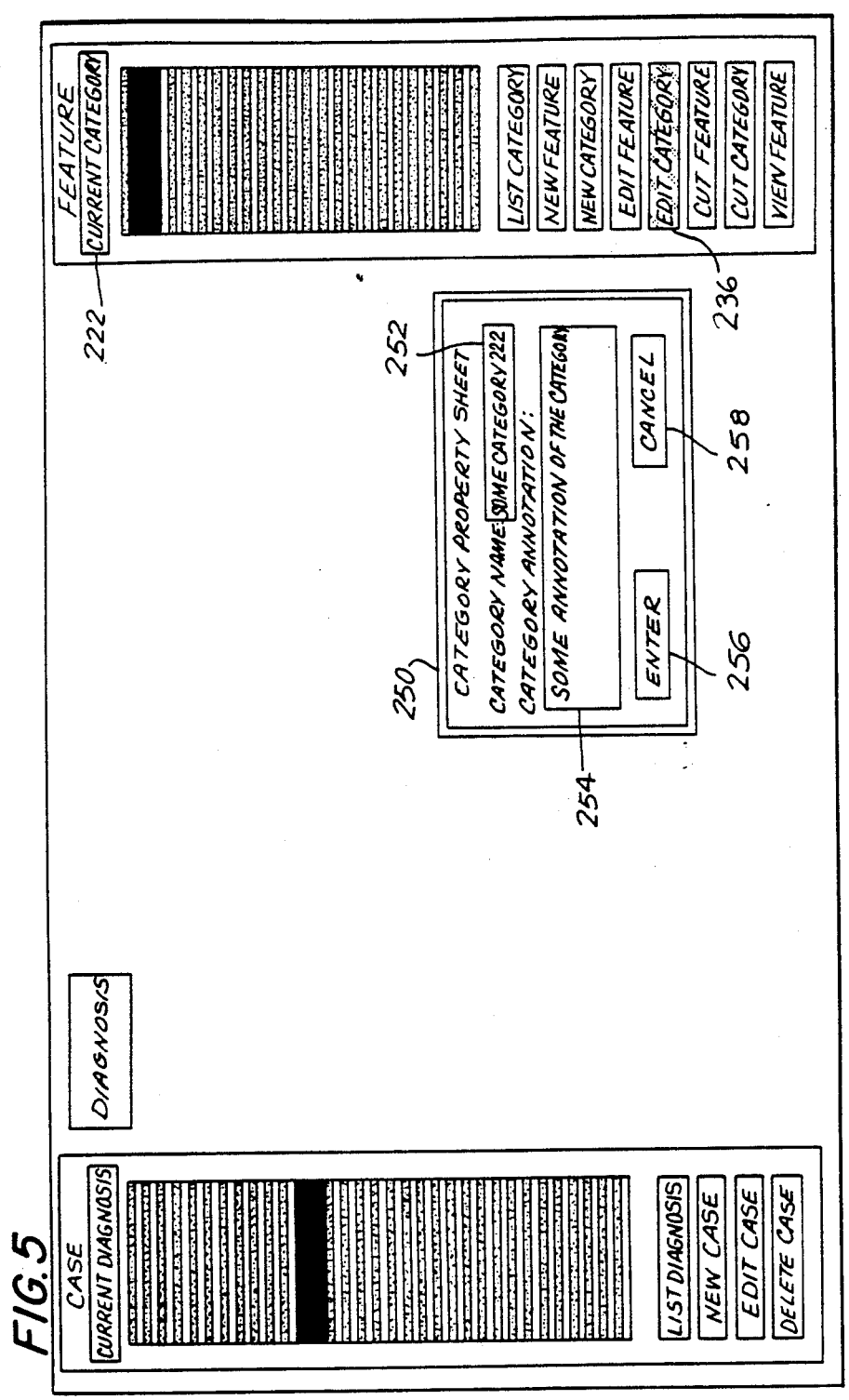
FIG. 5 is a display used in editing a previously created category.

The actuation of edit category button 236 causes monitor 106 to display an edit category frame which identifies the then current category indicated in message 222. The name of this category may be modified, for example, to provide a more accurate description of the features contained therein. Also, an annotation describing this category may be revised as desired. Any changes to the name or annotation of the category are stored in the knowledge base and, thus, are written into each case record. The edit category function is more fully described with reference to FIG. 5.

Figure 13:
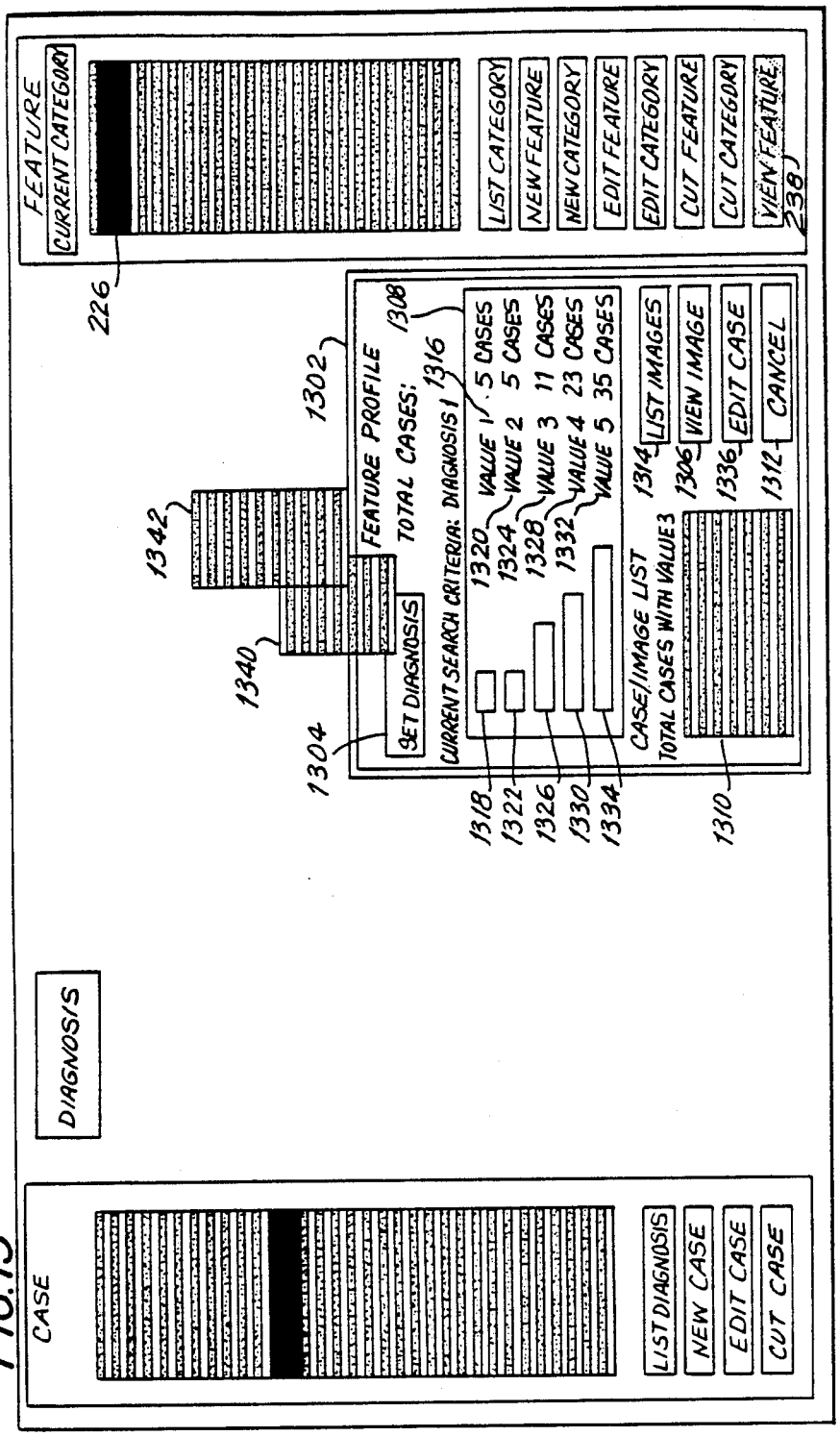
FIG. 13 is a display used in viewing the value of a feature.

The actuation of view feature button 238 causes monitor 106 to display a feature profile frame (described more particularly with reference to FIG. 13). The purpose of the feature profile frame and, thus, one of the functions of the view feature mode of operation is to permit the expert to search for cases included in the data base in which the feature being viewed (i.e. selected feature 226) is present. It is expected that a typical feature will have different values in different cases. The feature profile frame not only identifies those cases having the selected feature but also provides an indication of the distribution relative to each other of those cases having different values of this feature. For example, a histogram illustration may be displayed. The view feature mode of operation also enables the expert to establish search criteria, such as to search for those cases having not only the selected feature 226 but other features, thereby enabling the expert to determine the relative importance or influence of the selected feature in conjunction with other characteristics. The search criteria also may be based on a selected diagnosis, whereby the knowledge base is searched for case records having both the selected diagnosis and the selected feature. A list of those cases which have been found by this search is displayed, and the case record of any of the displayed cases may be retrieved and displayed on monitor 106.

As a preferred aspect of this invention, if the selected feature for which the feature profile has been produced is a visual feature, it may be displayed. As described with reference to FIG. 14, those pictorial images included in the retrieved cases may be read from optical disk 112 and displayed on monitor 106. The expert thus may observe the visual characteristics of the selected feature 226, pariticularly in the environment established by the search criteria which he has established.

Figure 15:
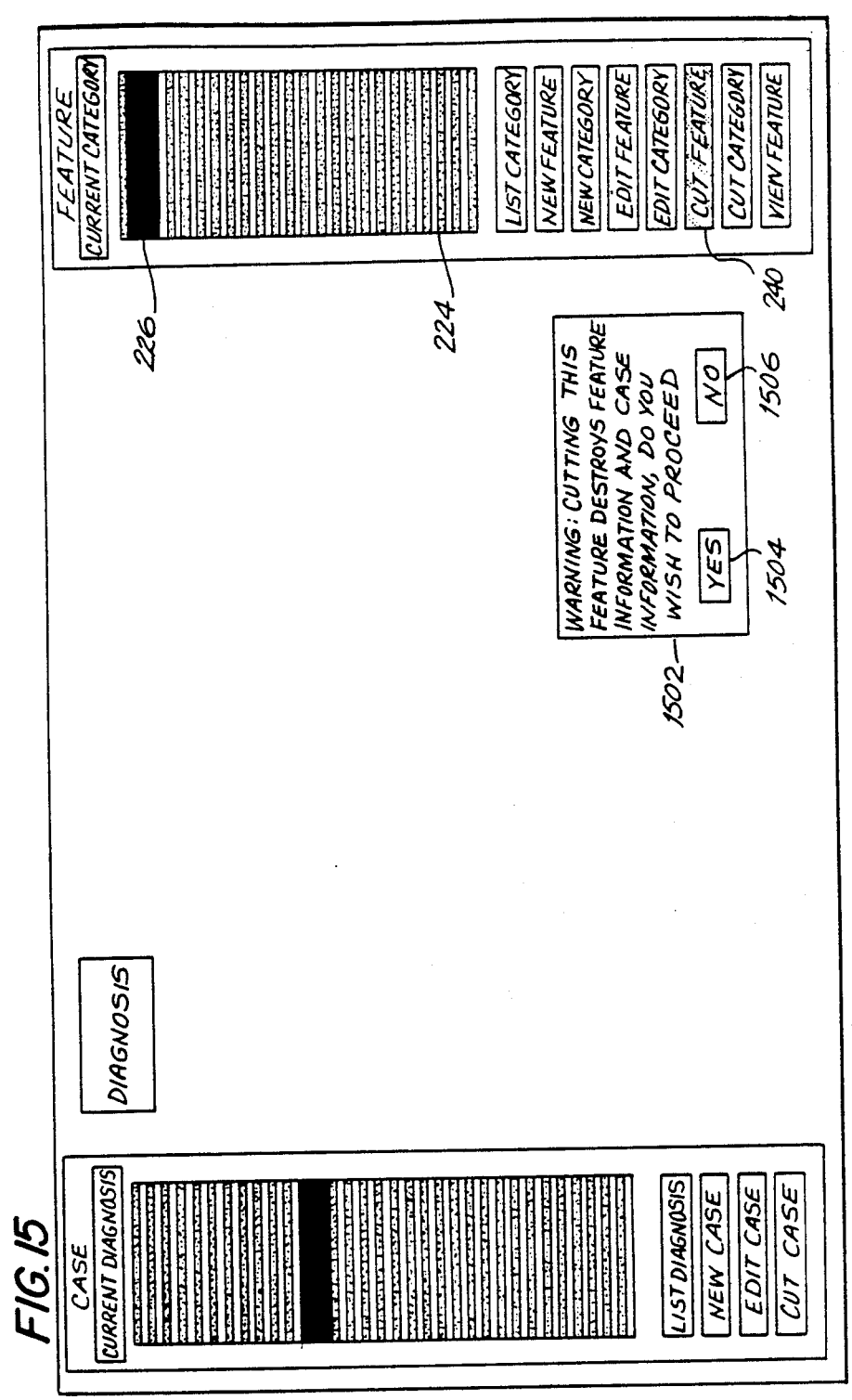
FIG. 15 is a display used in deleting a feature.

The actuation of cut feature button 240 effectively deletes the selected feature 226 from the knowledge base. Since each case record includes a value of this feature, even if that value is "not applicable", it is recognized that the deletion of selected feature 226 may result in the loss of significant information from the case records in the knowledge base. Consequently, as shown in FIG. 15, a warning message is provided on monitor 106 requiring the user either to confirm or withdraw this cut feature operation. Upon confirmation, this feature is deleted from the knowledge base dictionary and from all of the case records included therein. However, if the user withdraws this selection of the cut feature operation, monitor 106 merely returns to display home screen 200, thereby permitting the user to initiate any desired operation, as represented by the actuation of one of buttons 208-214, or one of buttons 228-242, or diagnosis button 244.

Figure 16:
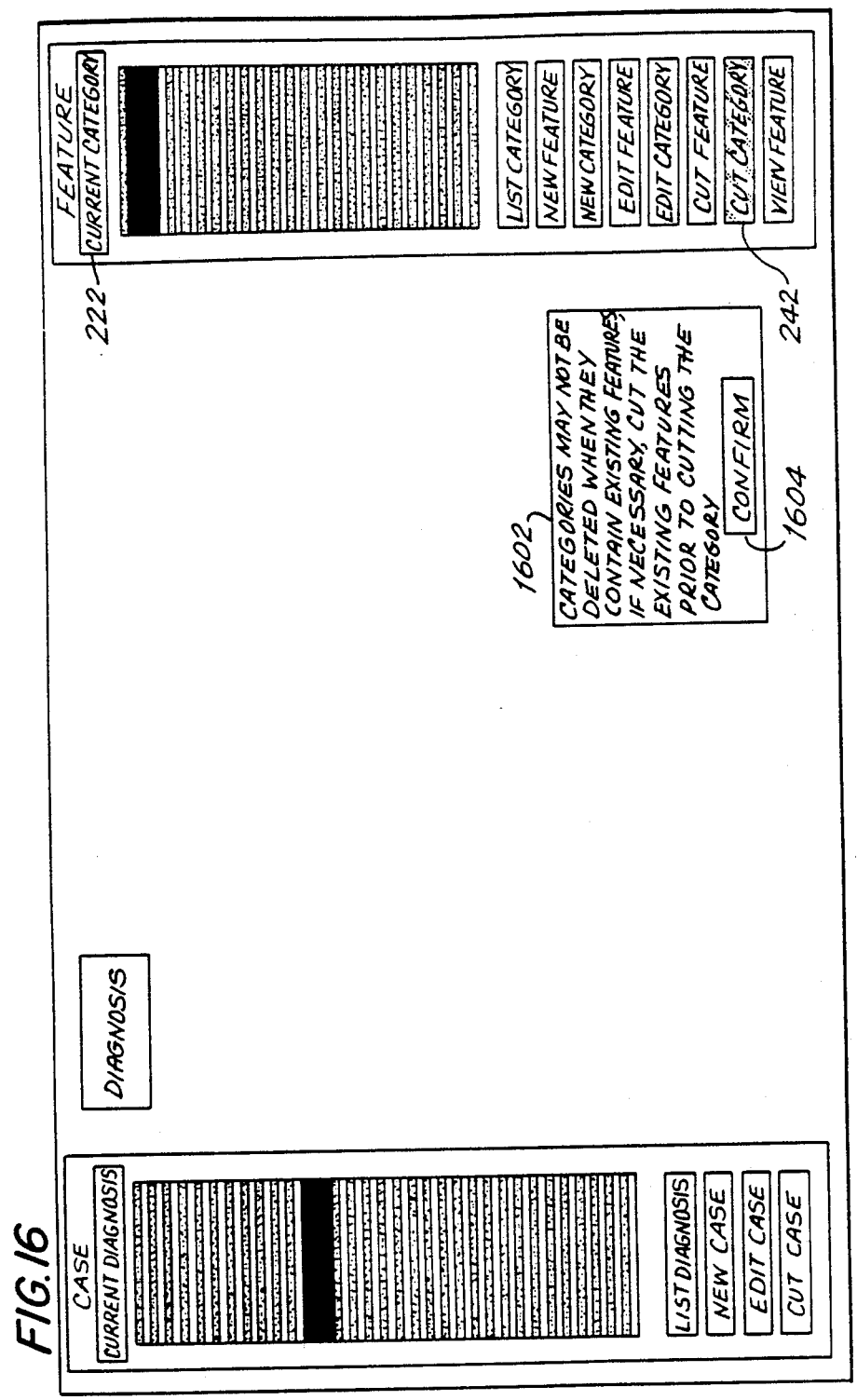
FIG. 16 is a display used in deleting a category.

If cut category button 242 is actuated, an operation similar to that described above with respect to the actuation of cut feature button 240 is carried out. In the cut category operation, a confirmatory message is displayed on monitor 106, as illustrated in FIG. 16. The purpose of the cut category operation is to delete from the knowledge base the current category indicated in message 222. However, this category may include one or more features whose values have already been assigned. Since the cut category operation would delete those features from the knowledge base, processor 102 is programmed to preclude the cut category operation from being carried out in the event that the current category selected for deletion contains one or more features which themselves have not yet been deleted from the dictionary. If the current category does not include such features, the user may confirm that the current category should be deleted; and upon such confirmation the knowledge base is updated by deleting the current category from the dictionary.

Home screen 200 is provided with a diagnosis button 244, the actuation of which causes monitor 106 to display a so-called diagnosis tree. This tree is created by the expert and is used to verify the accuracy by which diagnoses are made on the basis of observed features and diagnoses which are precedent. An example of an existing diagnosis tree in illustrated in FIG. 26, and FIGS. 27-29 illustrate the manner in which the diagnosis tree may be expanded or edited. Since each case record includes a diagnosis, the diagnosis tree is a valuable tool in recognizing how one diagnosis leads to another.

A brief and simple example of the utility of this dignosis tree is as follows: Let it be assumed that, in the population of patients in which the knowledge base is interested, all of those patients have been diagnosed as having tumors. However, the tumor may be benign or malignant. In the diagnosis tree, these two diagnoses may be thought of as nodes of the tree, and both are on the same level and may be thought of as "siblings". For those patients having benign tumors, the next lower level of diagnoses is based upon the observation that such diagnoses appear only in patients who have benign tumors. This next lower level of diagnoses may be thought of as "children" of the preceding upper level. Similarly, the diagnosis "malignant tumor" will have dependent therefrom one or more "children" whose diagnoses are found only in patients having malignant tumors. The ability to edit the diagnosis tree permits refinements based upon experience and a greater population of cases and, of course, the expert's observations of those cases.

The flow charts of the various operations and routines carried out by processor 102 are self-explanatory. A working understanding and familiarity with the operating system used in the Sun microcomputer, and particularly the ability of that operating system to utilize windows and frames, to add layers or levels of routines with previously executed routines continuing as "background" is assumed. Likewise, the ability of the Sun microcomputer to function with its operating system in conjunction with mouse 110, and the capabilities and functions of that mouse, also is assumed. Consequently, a detailed description of each and every one of these flow charts need not be provided for a complete understanding of the present invention. Nevertheless, to familiarize the reader with these flow charts, the following describes the flow chart shown in FIG. 2A.

The flow chart shown in FIG. 2A is adapted to create the information illustrated in feature window 220 and to branch to an appropriate routine or function depending upon which of the illustrated buttons is actuated. To create the information in feature window 220, the processor first retrieves from the knowledge base a list of all of the categories therein, as indicated at 201 in FIG. 2A, and as shown at 203, the processor creates the current category message illustrated as message 222 in FIG. 2. The processor then advances to instruction 205 which selects the "default" category in the category list and displays this default category as the current category in message 222. Typically, the default category simply is the first category in the category list of the knowledge base.

The processor then advances to instruction 207 and retrieves from the knowledge base the list of features included in the category depicted as the current category. These features are listed as feature list 224, any one of which may be selected, as mentioned above. After listing these features, as at 209, the processor advances to instruction 211 and selects the first feature in this list as selected feature 226. It is appreciated that, if desired, any other feature in list 224 may be selected.

The processor then creates buttons 228-242, as represented by sequential instructions 213-227. The sequence in which these buttons are created and the order in which they are displayed in feature window 220 may be varied as desired. Once feature window 220 is created and displayed, the processor simply "waits", as represented by instruction 229, until action is taken by the user.

Figure 3A:
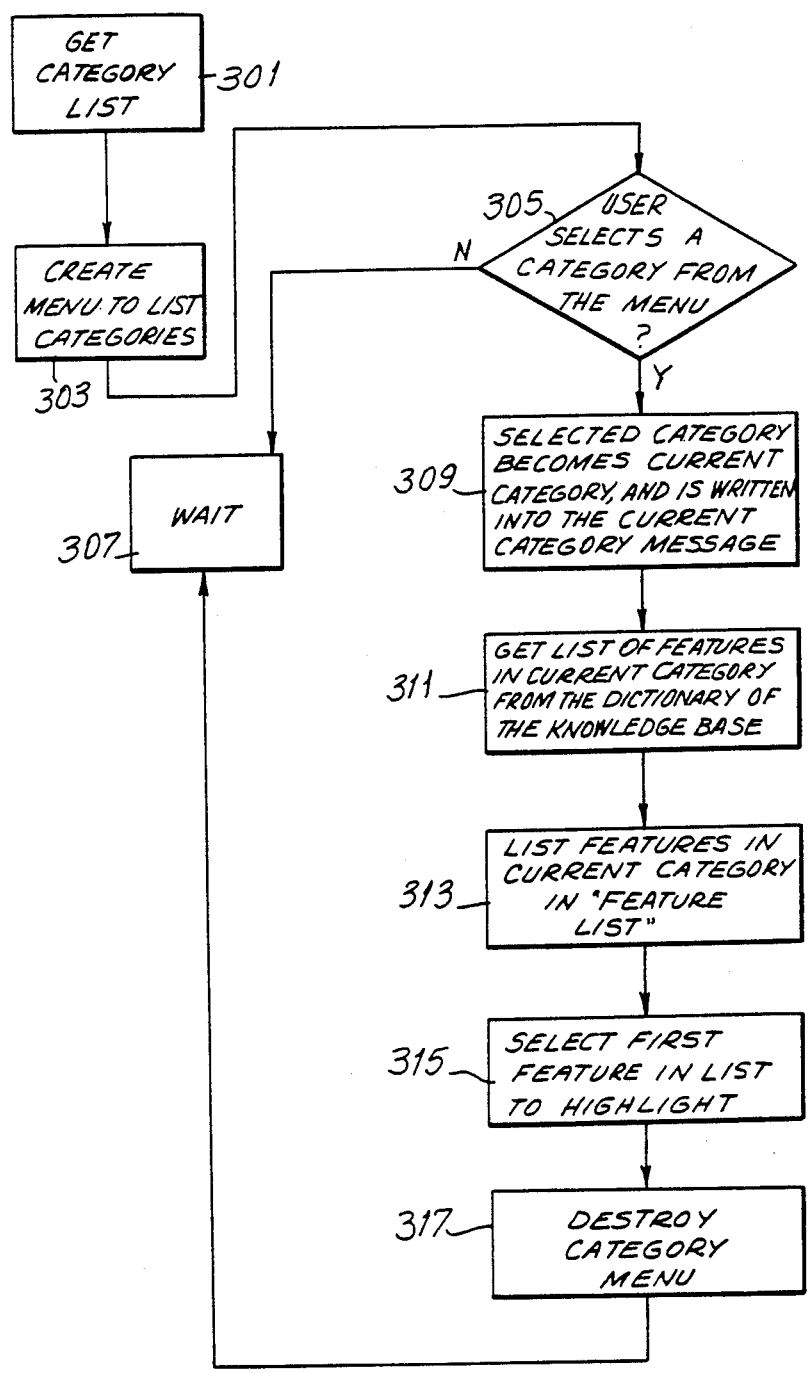
FIG. 3A is a flow chart representing the manner in which the list of categories is obtained.
Figure 5A:
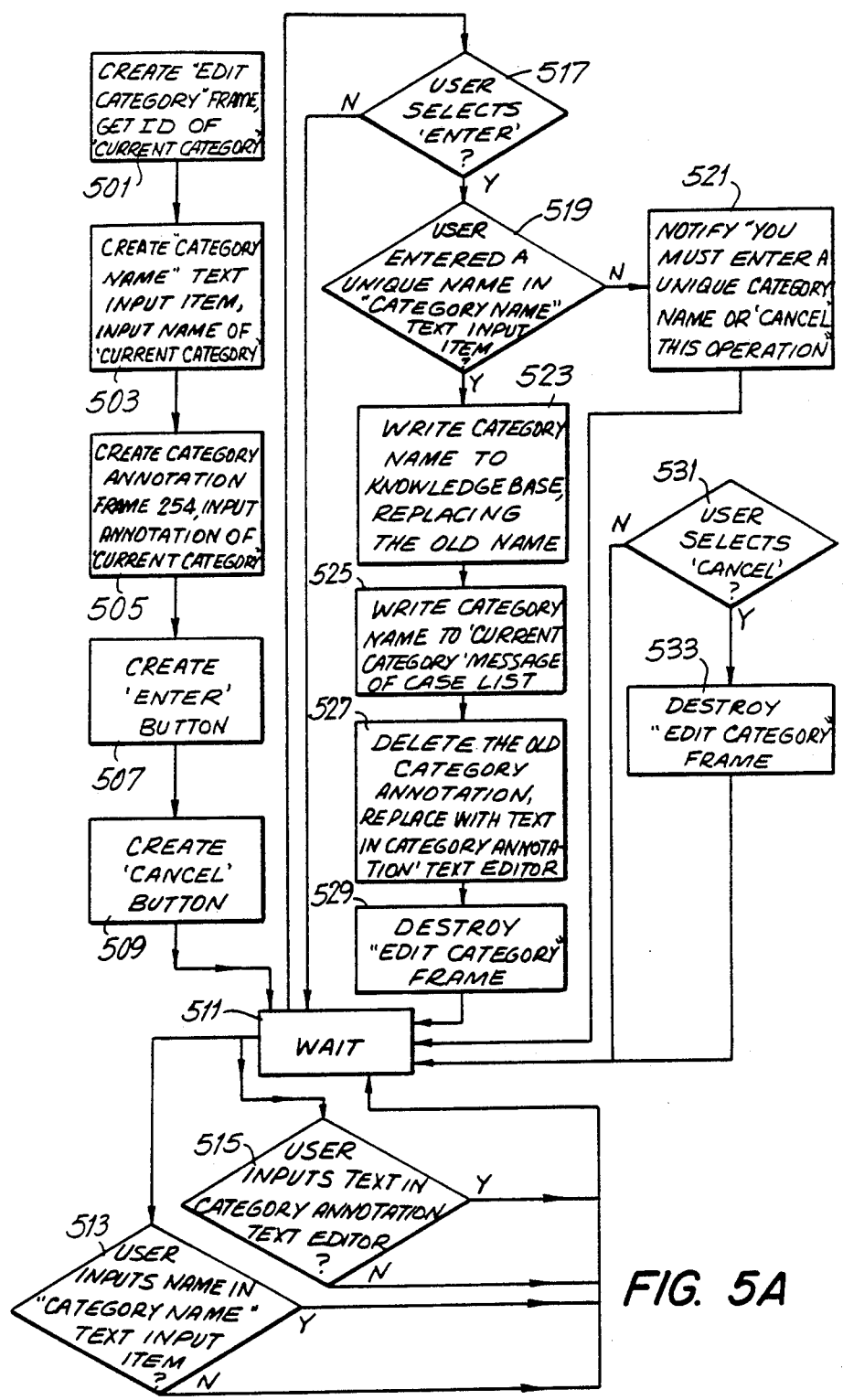
FIG. 5A is a flow chart representing the manner in which a category is edited.

The state of waiting for the user to actuate a button is represented by the various inquiries depicted in FIG. 2A. Depending upon which button is actuated by mouse 110, the corresponding function, or routine, represented by that button is carried out. Thus, if list categories button 228 is actuated, as indicated by an affirmative answer to inquiry 231, the processor branches to a set category routine illustrated by the flow chart of FIG. 3A. If create category button 232 is actuated, as represented by an affirmative answer to inquiry 239, the processor advances to the new category routine represented by the flow chart of FIG. 4A. If edit category button 236 is actuated, as represented by an affirmative answer to inquiry 247, the processor advances to the edit category routine illustrated in FIG. 5A. If create feature button 230 is actuated, as represented by an affirmative answer to inquiry 235, the processor advances to the new feature routine illustrated by the flow chart of FIG. 6A.

Figure 6:
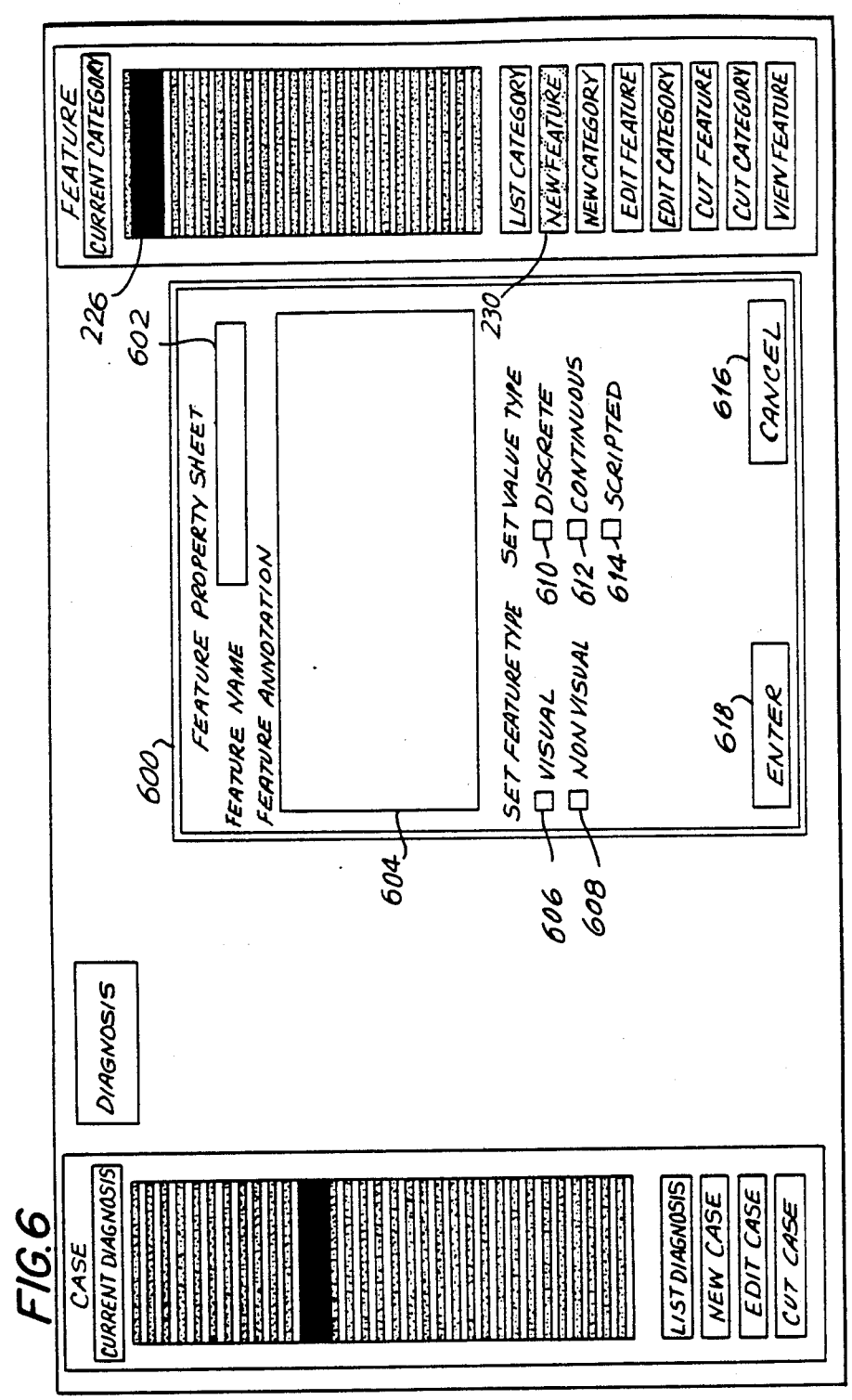
FIG. 6 is a display used in creating a new feature.
Figure 6A:
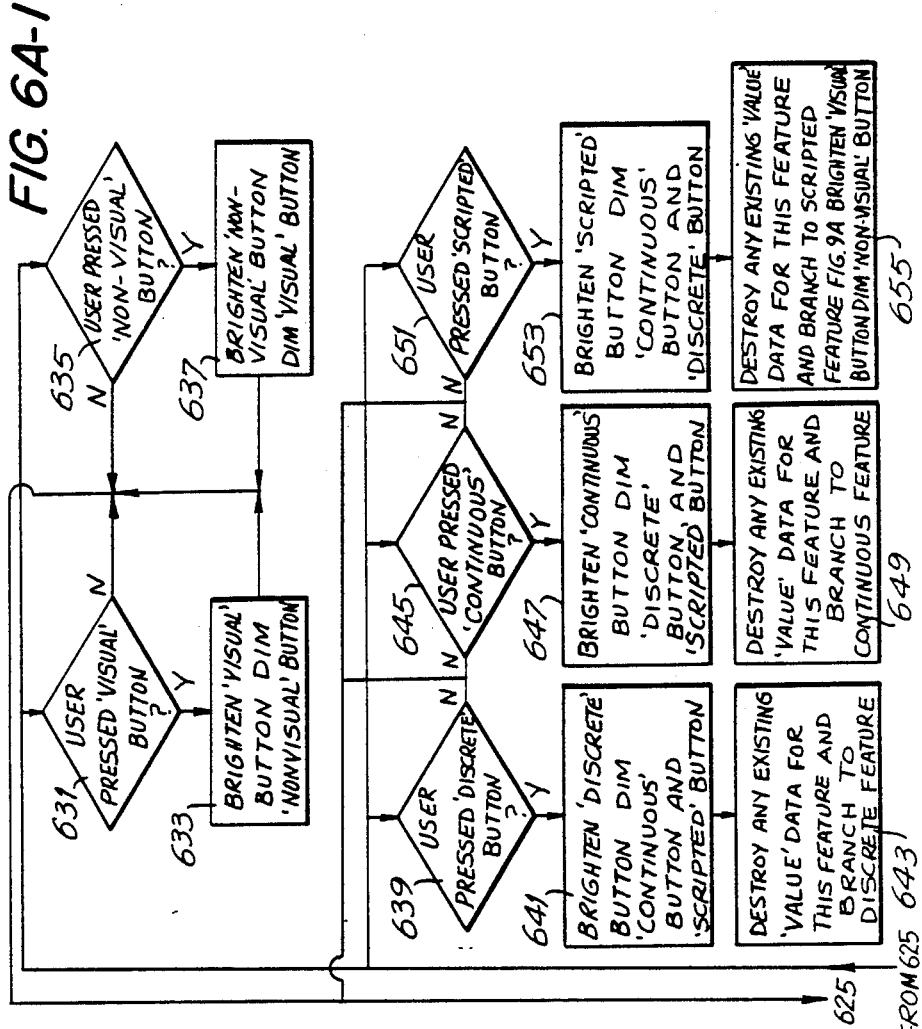
Figure 1:
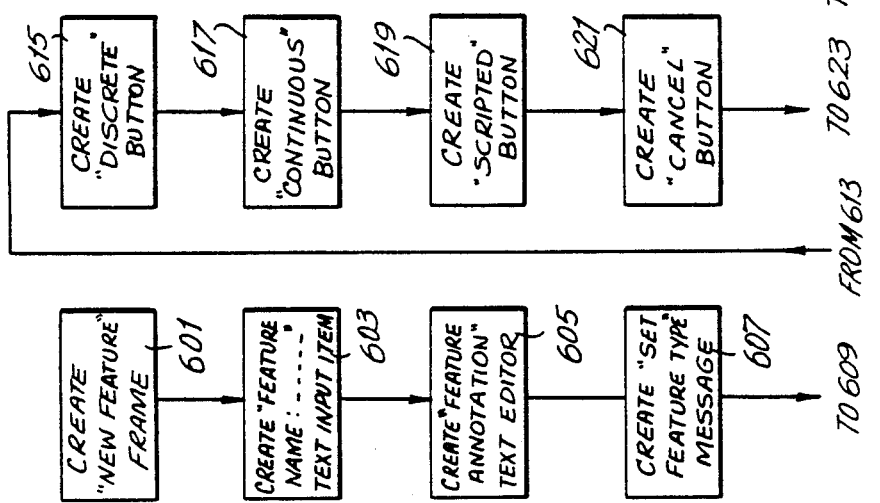
FIG. 1 is a block diagram of one embodiment of the system of the present invention.
Figure 7:
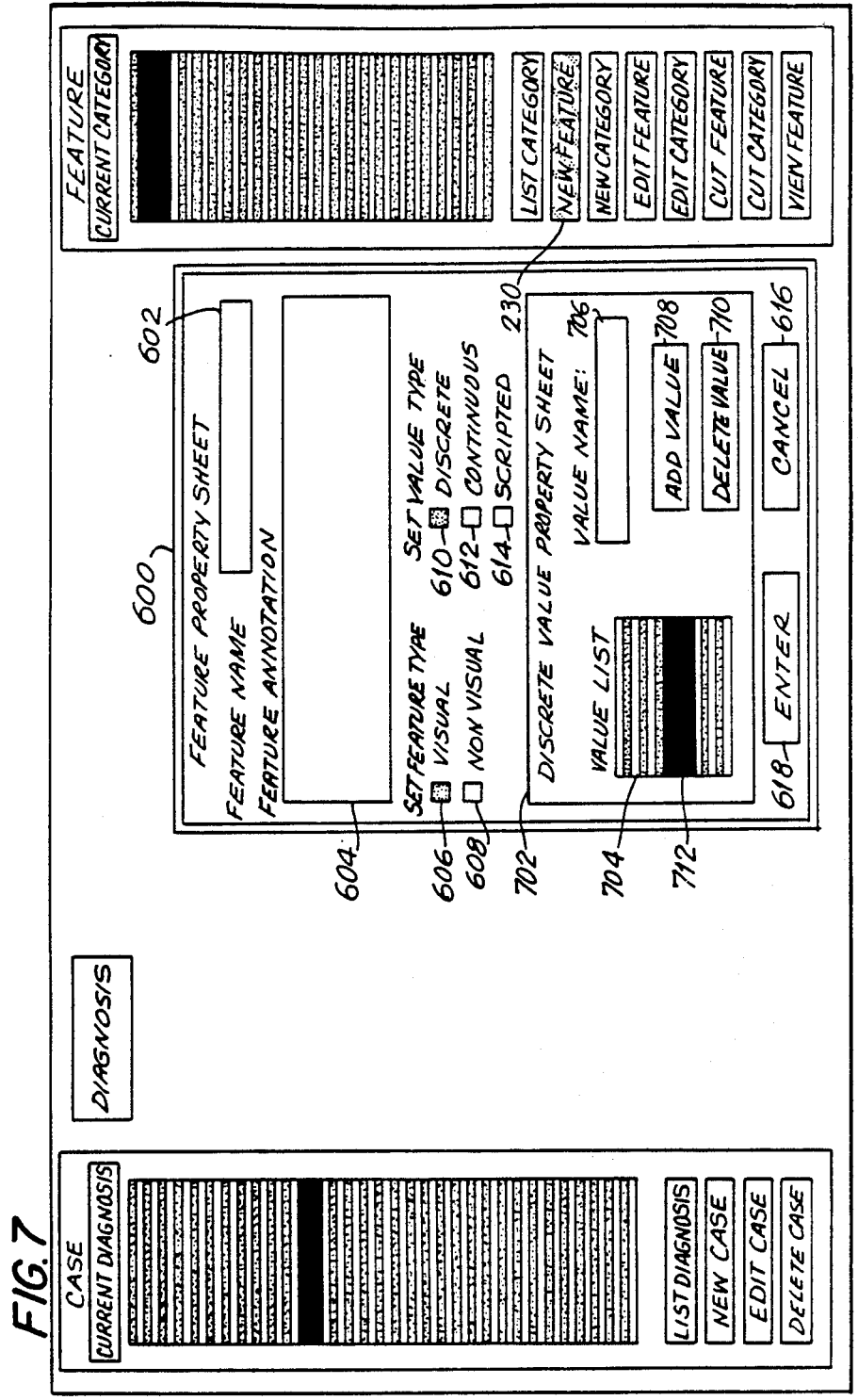
FIG. 7 is a display used in creating a feature having a discrete value.
Figure 7A:
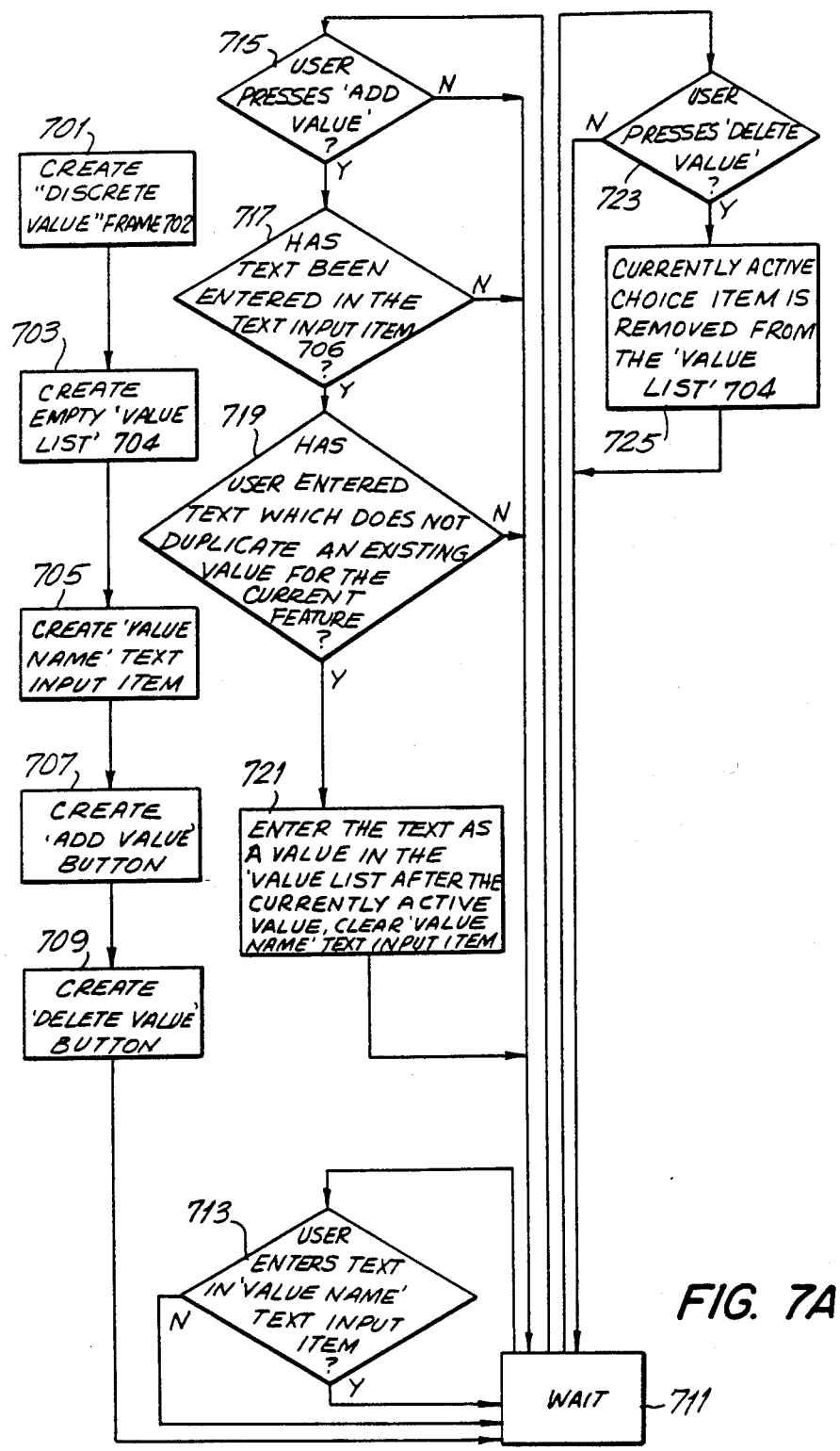
FIG. 7A is a flow chart representing the manner in which the discrete value feature is created.
Figure 8:
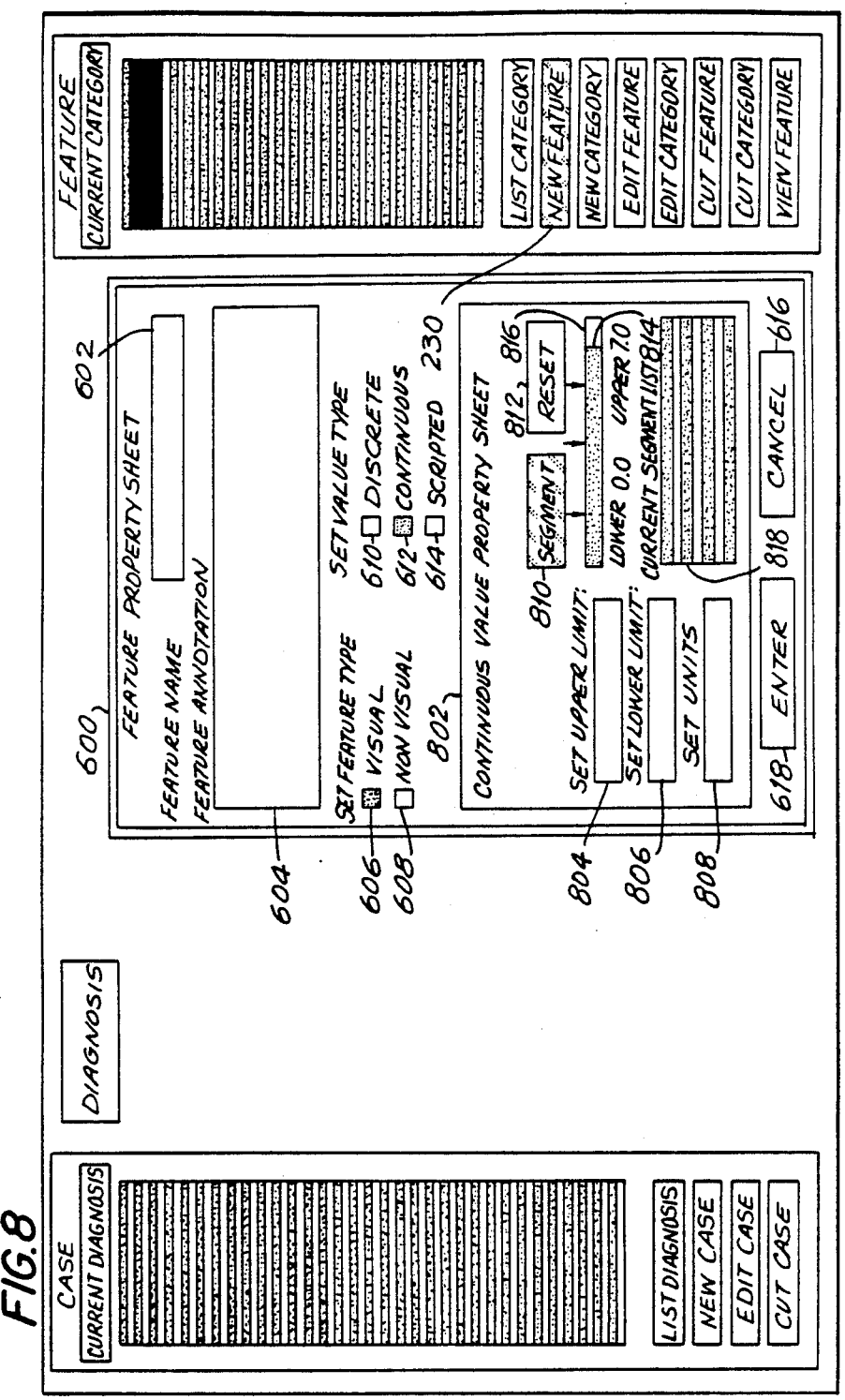
FIG. 8 is a display used in creating a feature having a continuous value.
Figures 1, 8A:
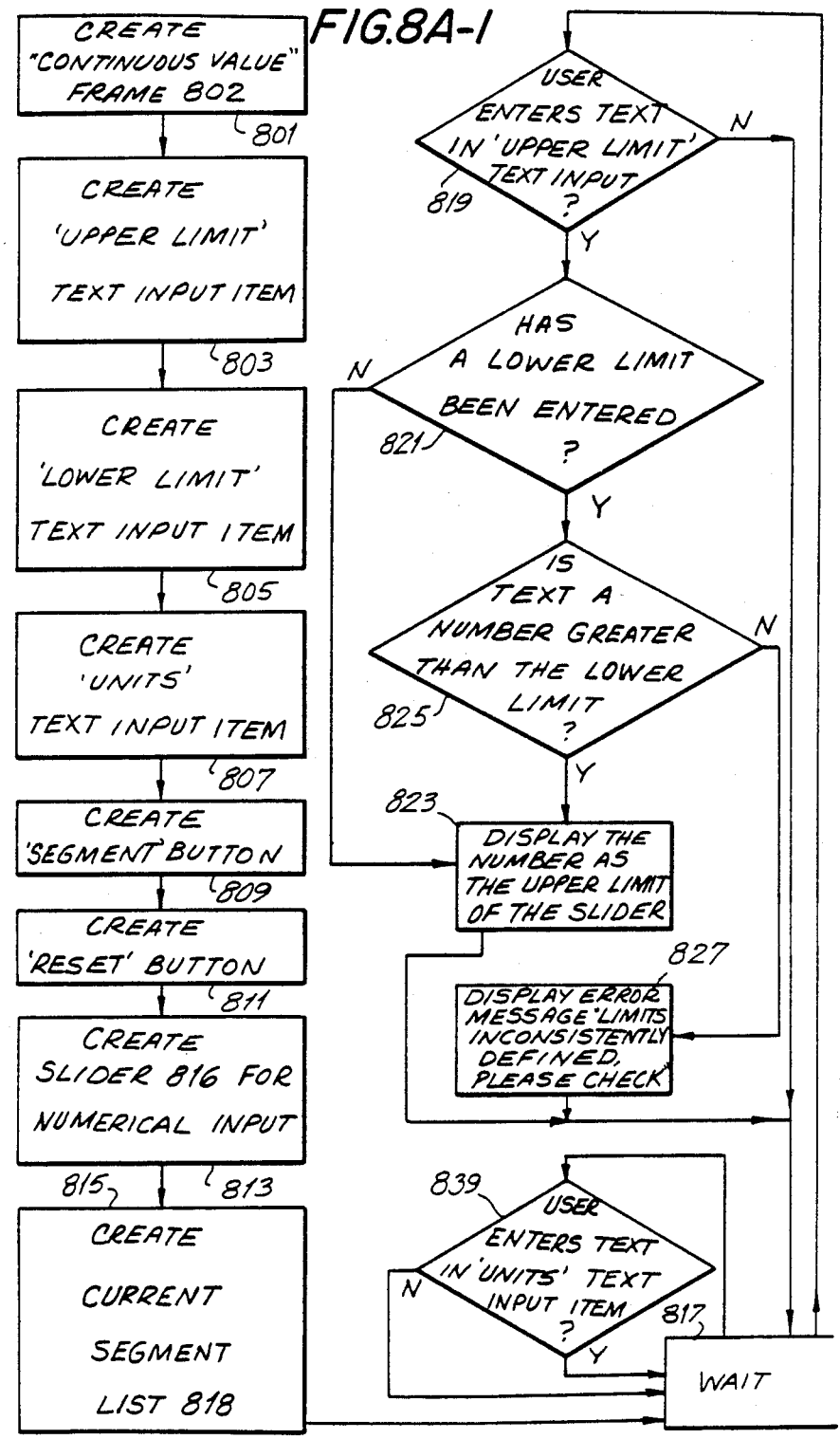
Figures 2, 8A:
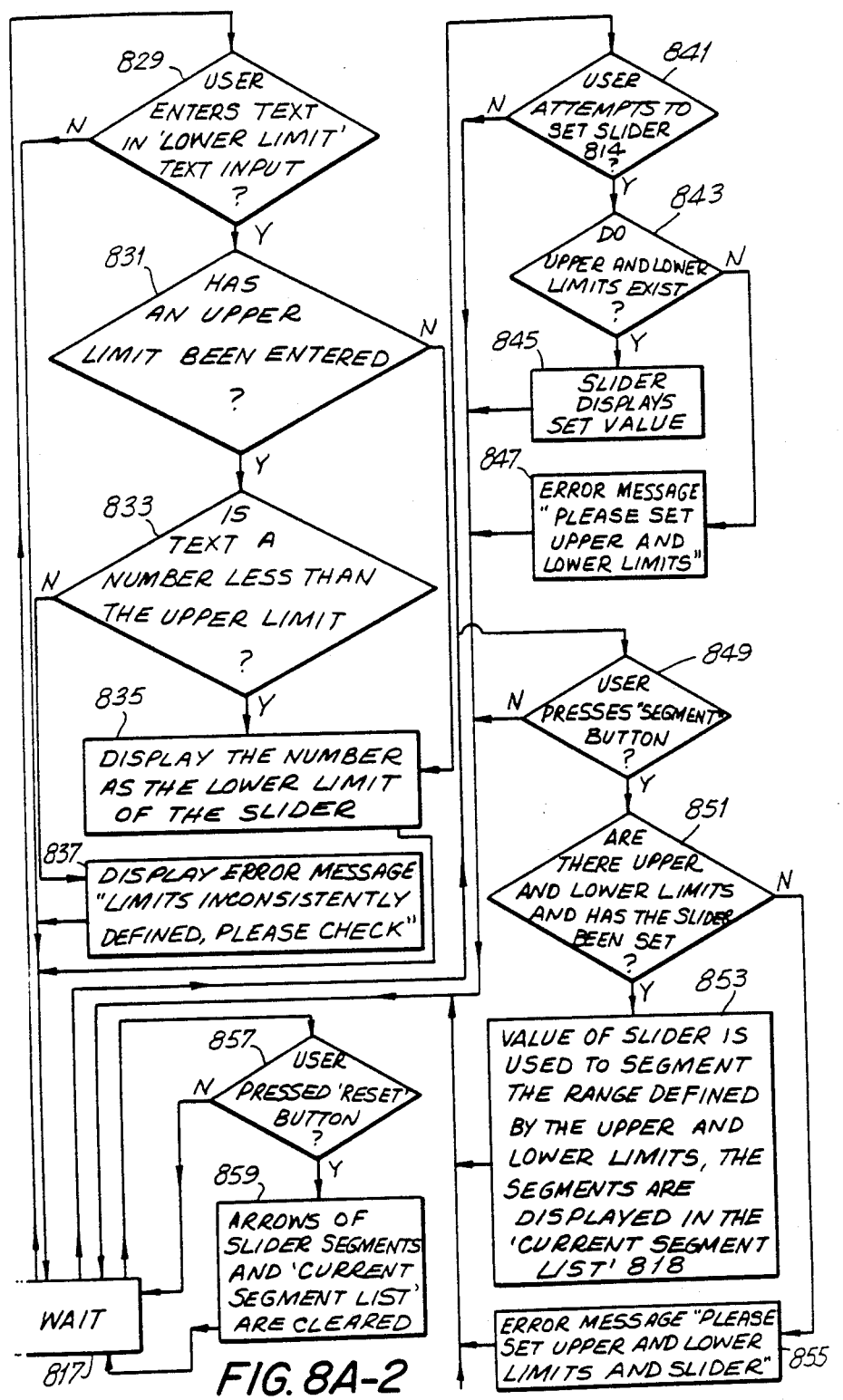
Figure 9:
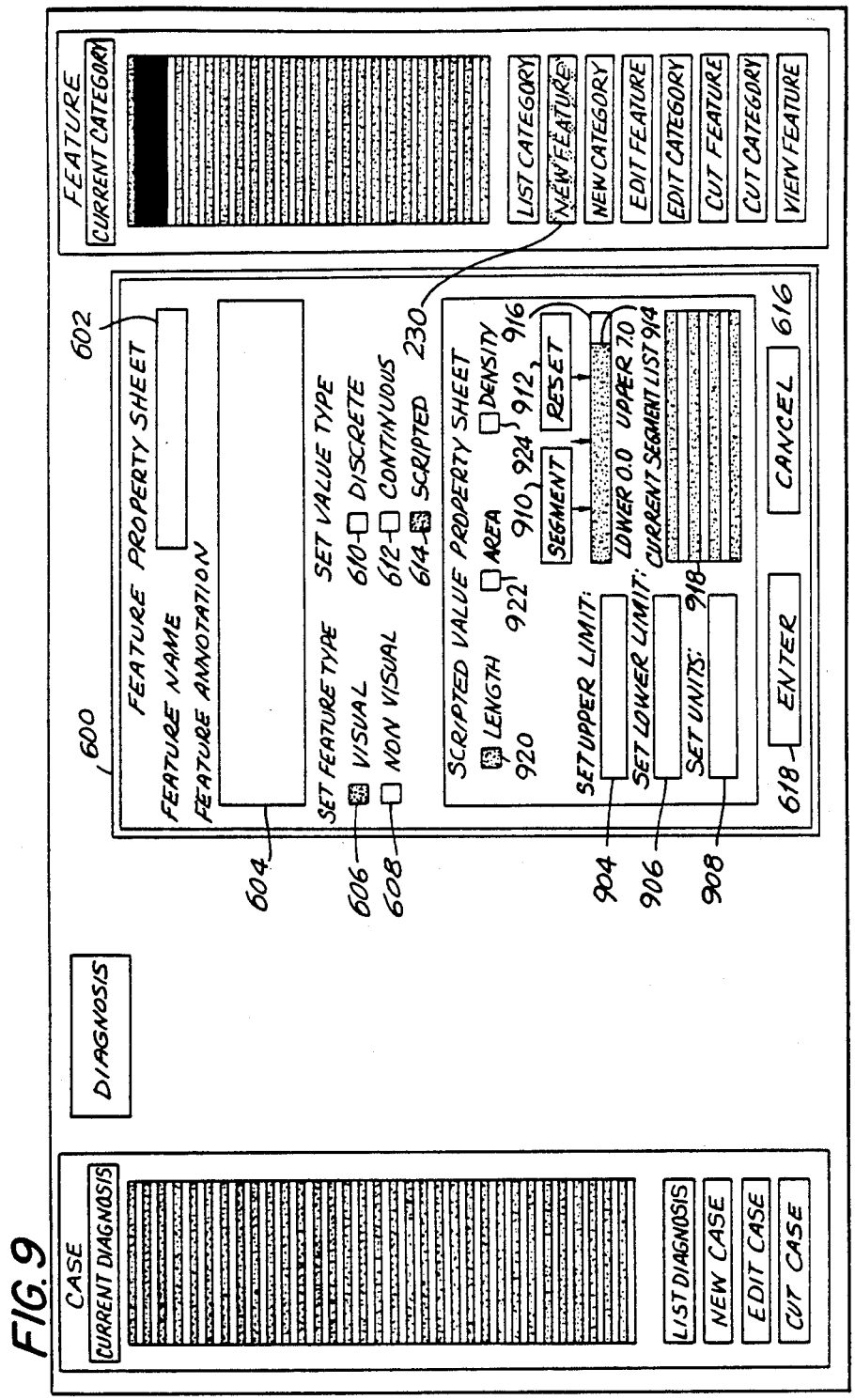
FIG. 9 is a display used in creating a feature having a scripted value.
Figures 1, 9A:
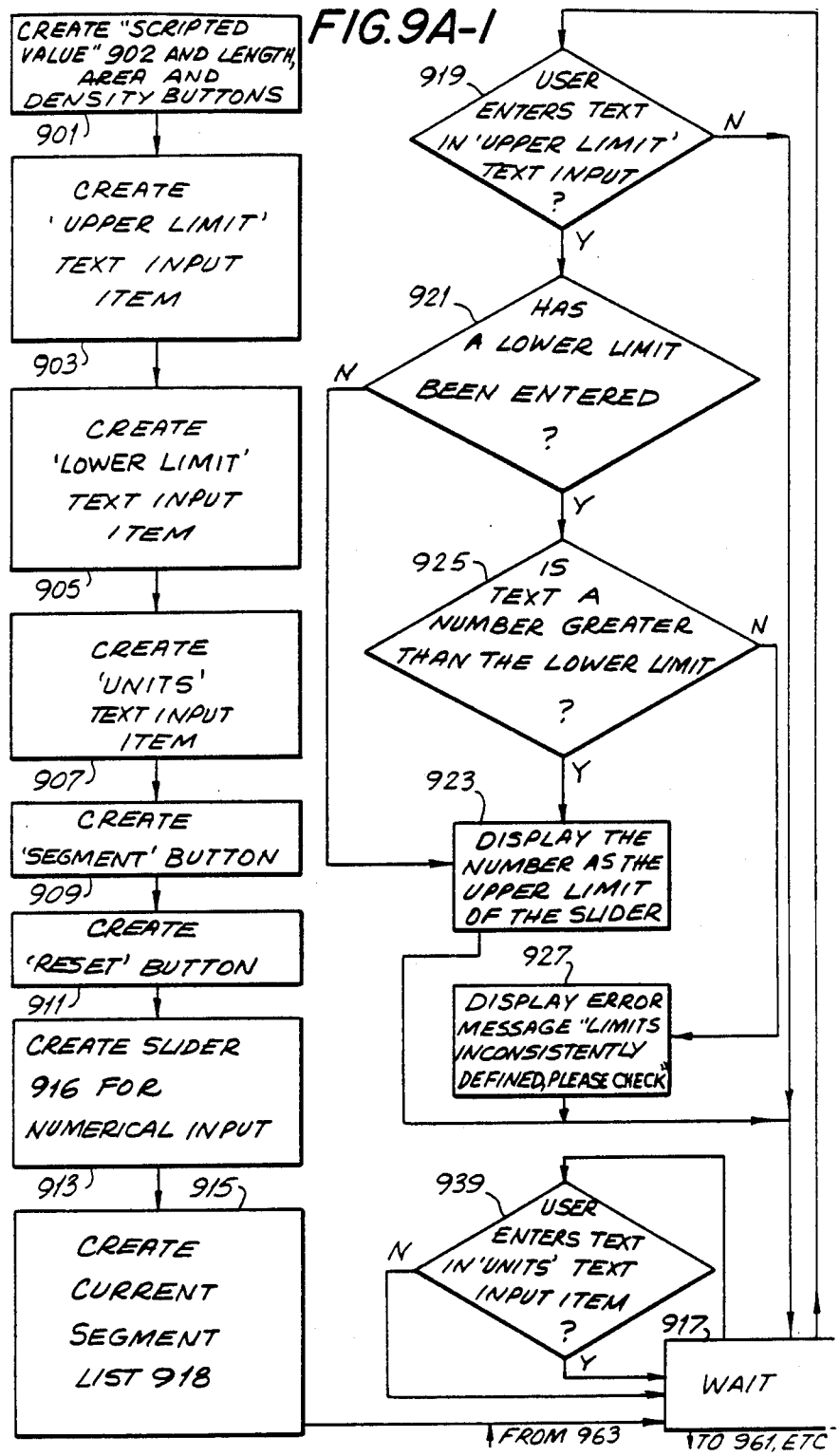
Figures 2, 9A:
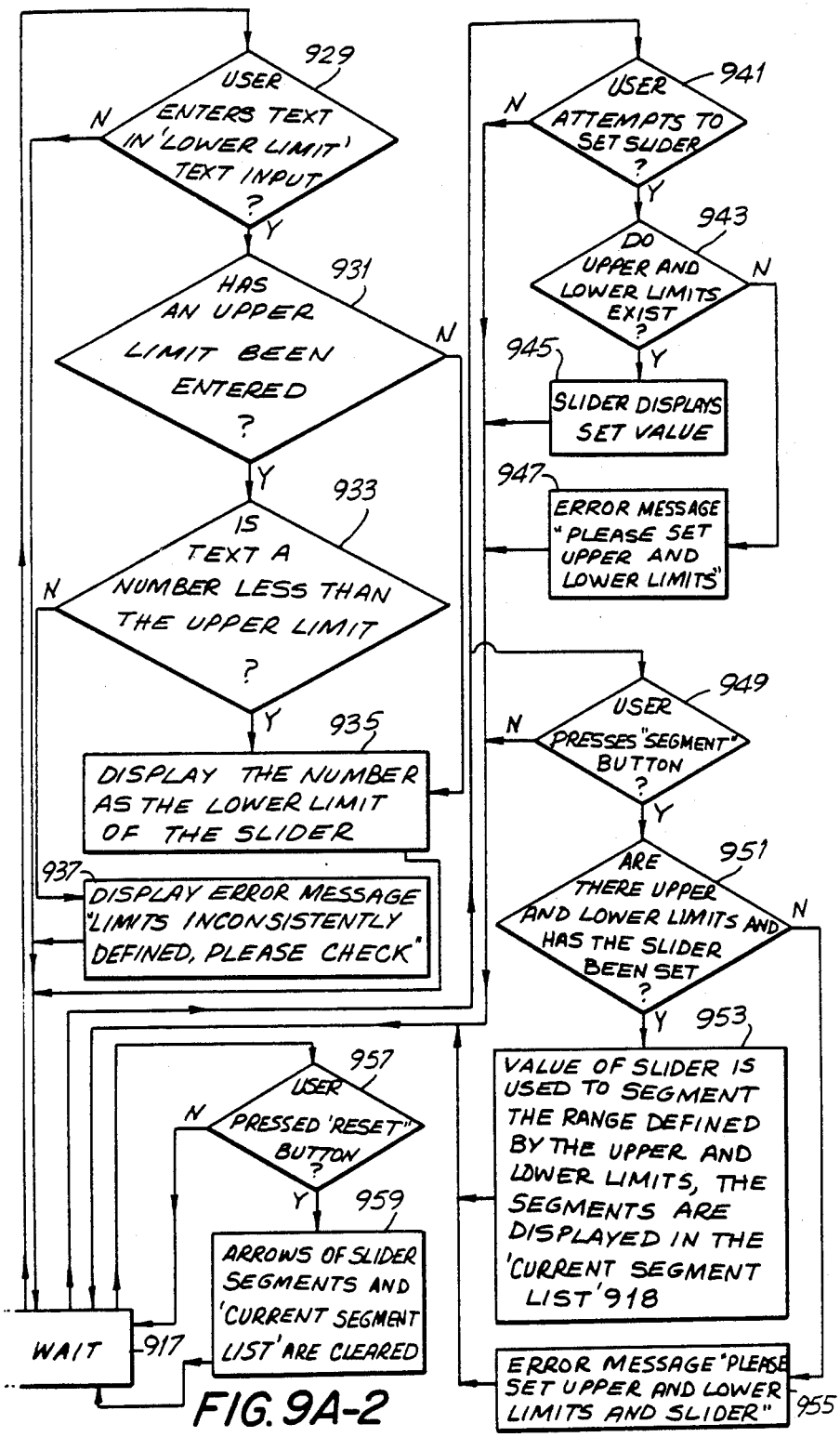
Figures 3, 9A:
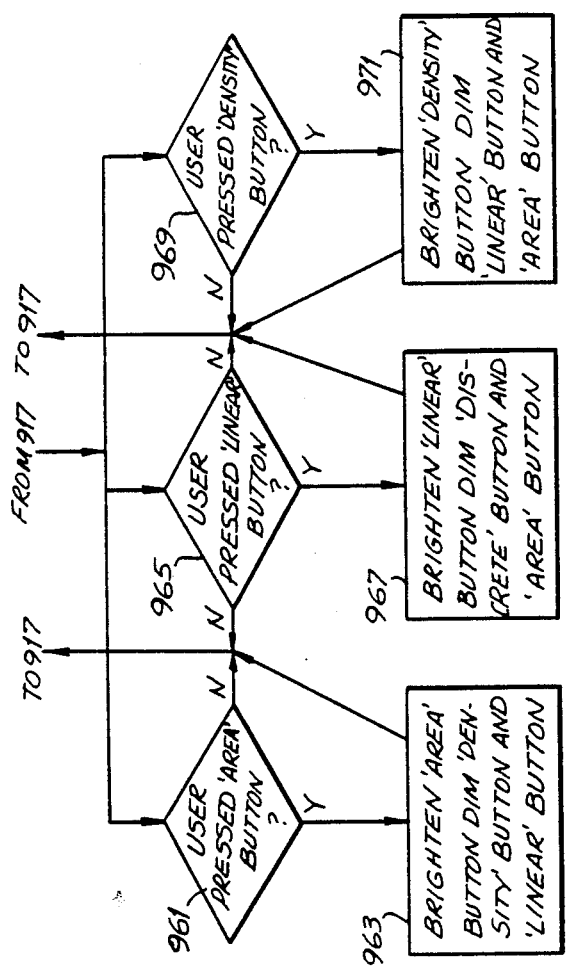

Digressing for a moment to the flow chart of FIG. 6A, the new feature operation comprises the function by which the expert may establish the appropriate values for the feature which he is creating. As mentioned above, a feature may be visual or non-visual, and may be characterized as a discrete feature whose value is represented by text (in many instances, simply a single word), a continuous feature whose value is represented by a numeral within a user-defined range of numbers or a "scripted" feature whose value (such as length, area or density) is measured directly from the displayed feature. FIG. 6 illustrates the "new feature" screen displayed on monitor 106, and it is seen that buttons are provided to enable the expert to select the feature type (visual or non-visual) and value type (discrete, continuous or scripted). Depending upon which of the value type buttons is actuated, the processor advances, as illustrated in the flow chart of FIG. 6A, to a discrete valued feature creating routine (whose display screen is illustrated in FIG. 7), to a continuous valued feature creating routine (whose display screen is illustrated in FIG. 8) or to a scripted valued feature creating routine (whose display screen is illustrated in FIG. 9).

Figures 1, 10A:
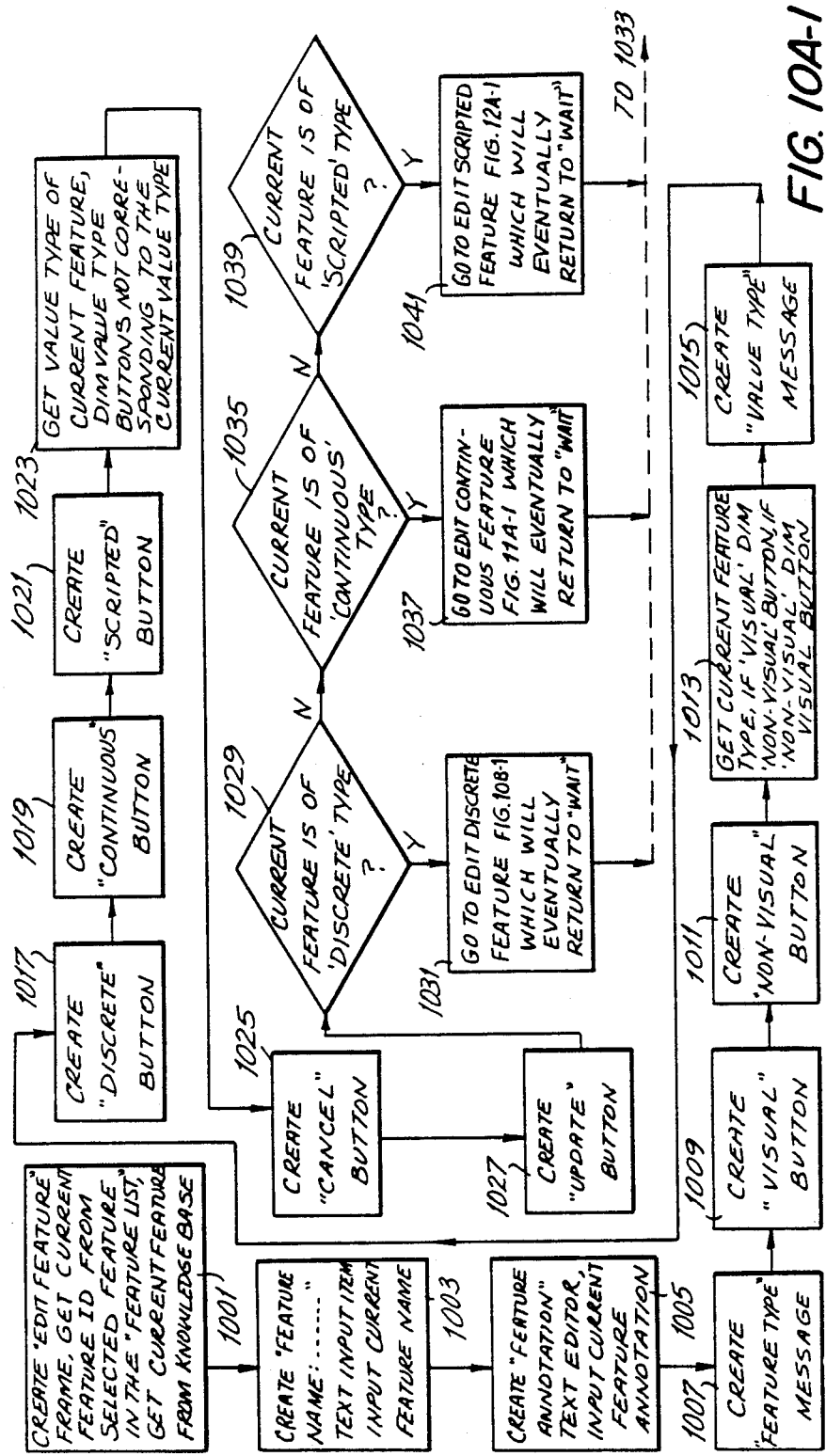
Figures 2, 10A:
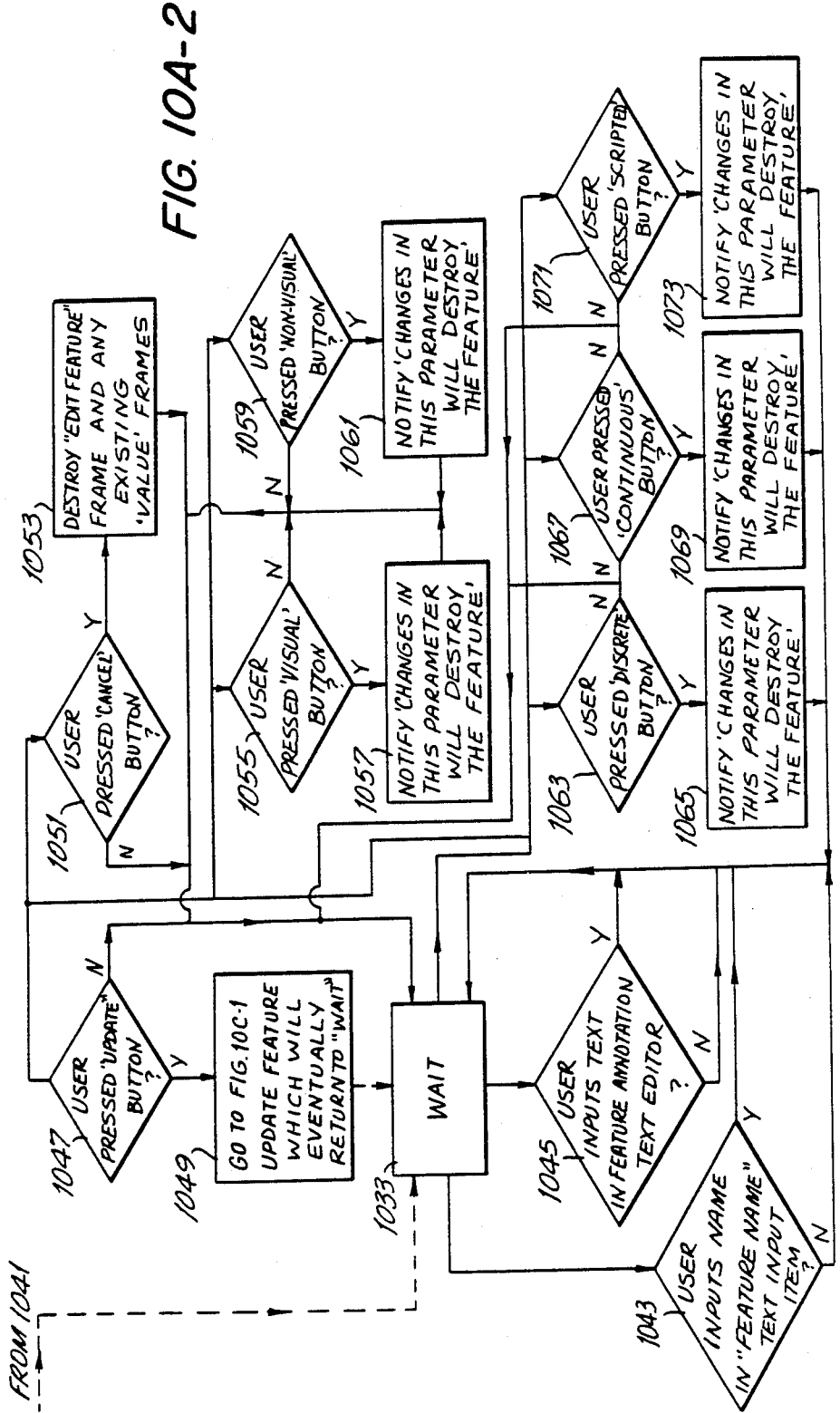
Figures 1, 10B:
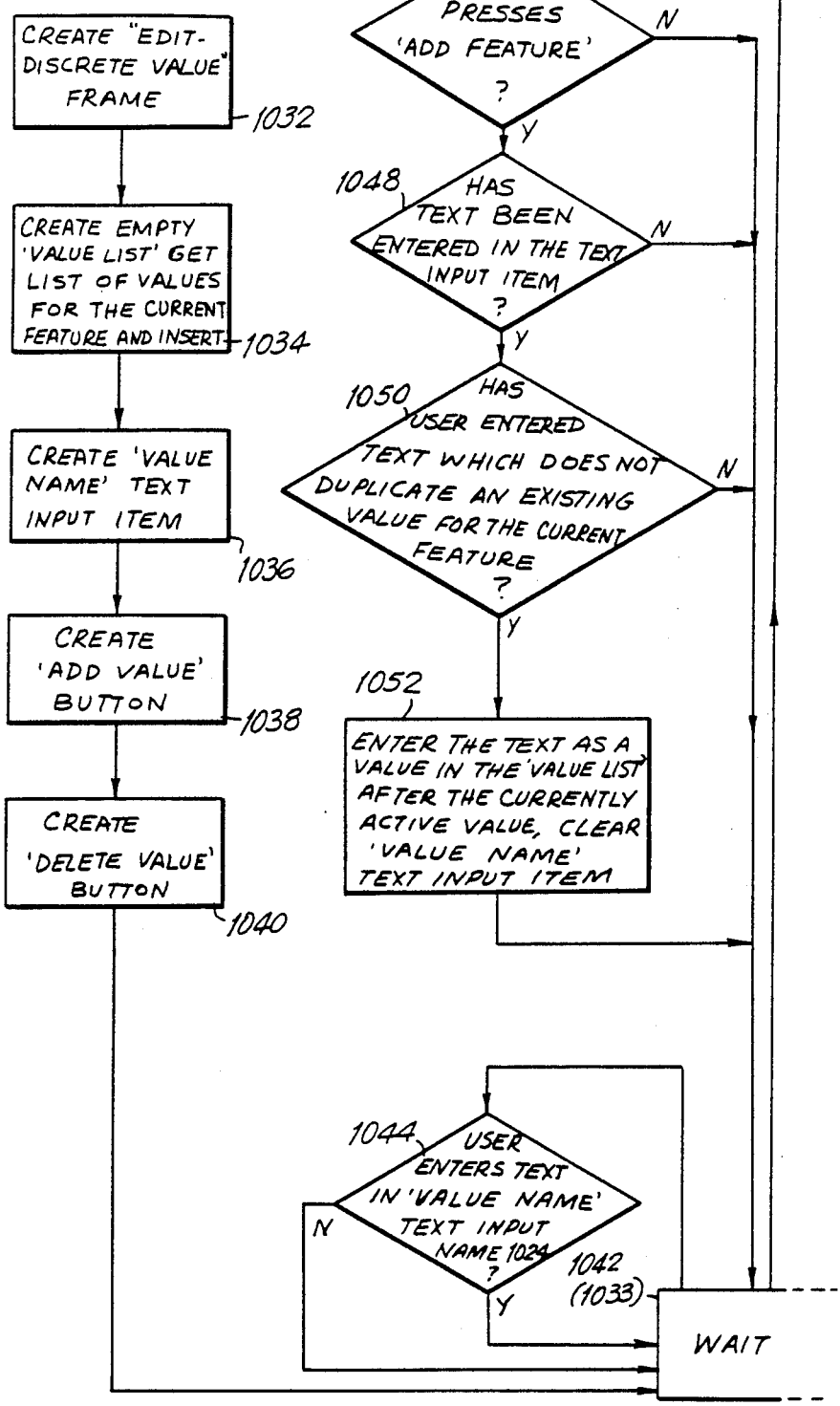
Figures 2, 10B:
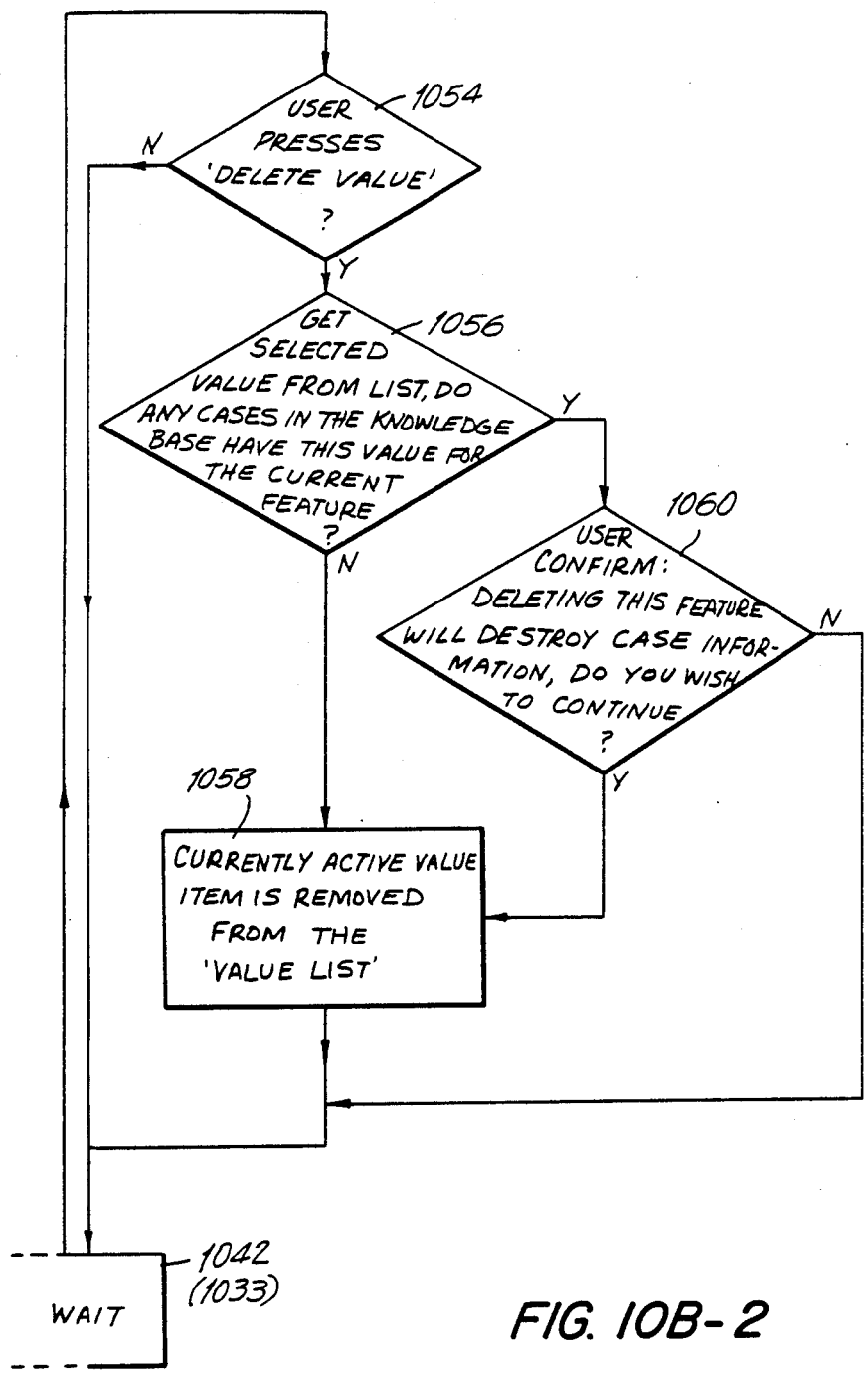
FIG. 2 illustrates the "home" screen.
Figures 2, 11A:
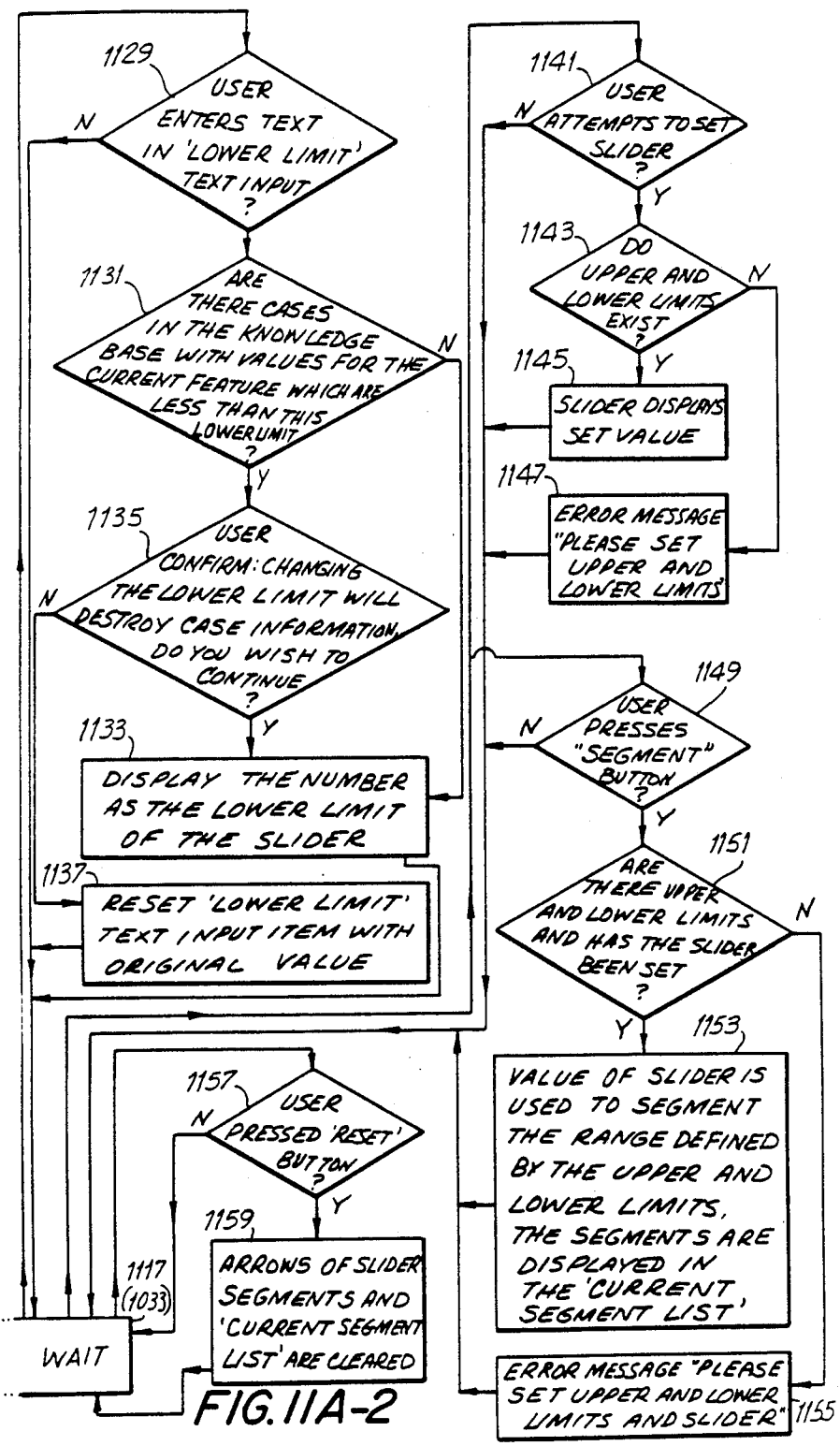
Figures 1, 12A:
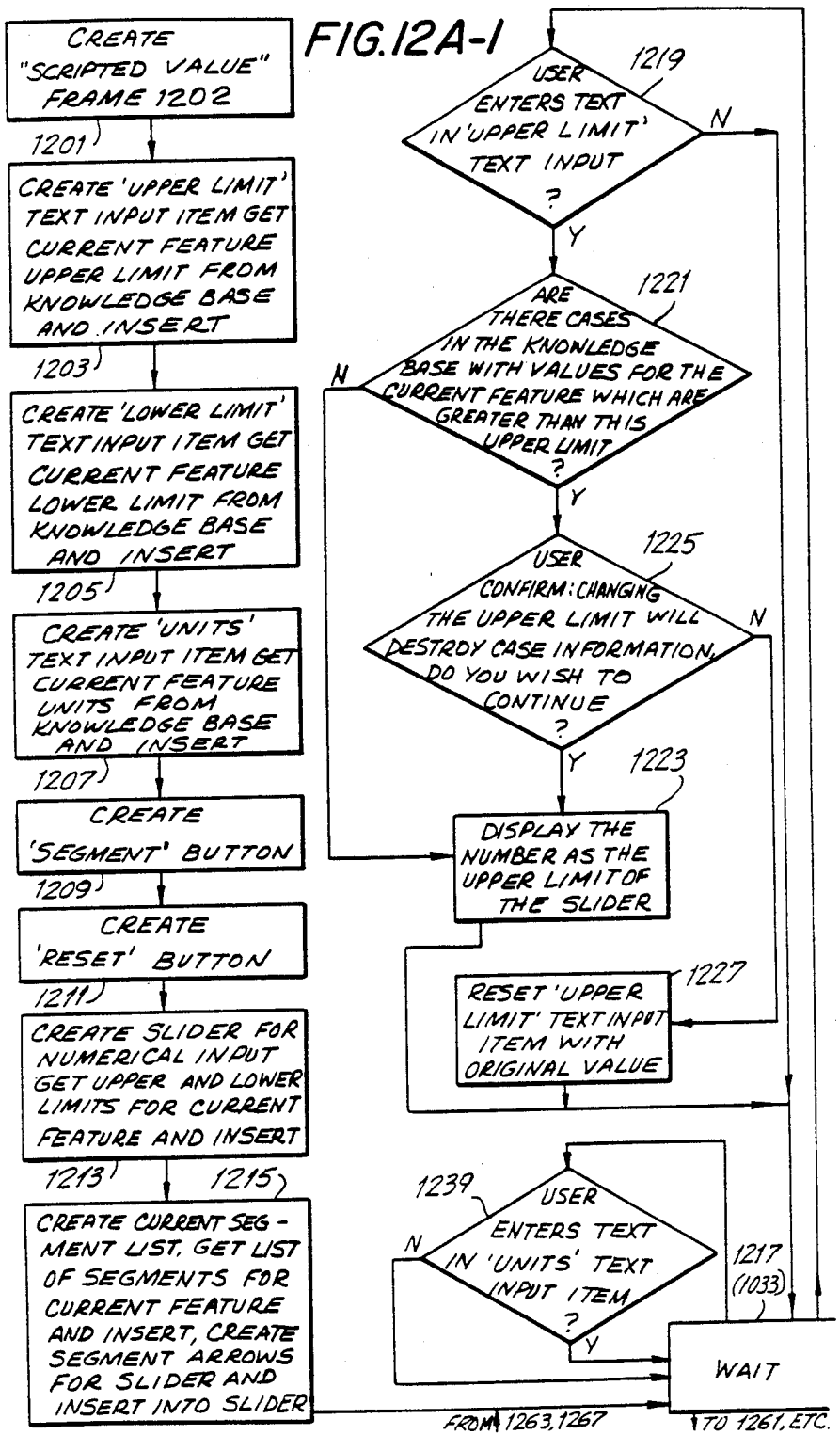
Figures 3, 12A:
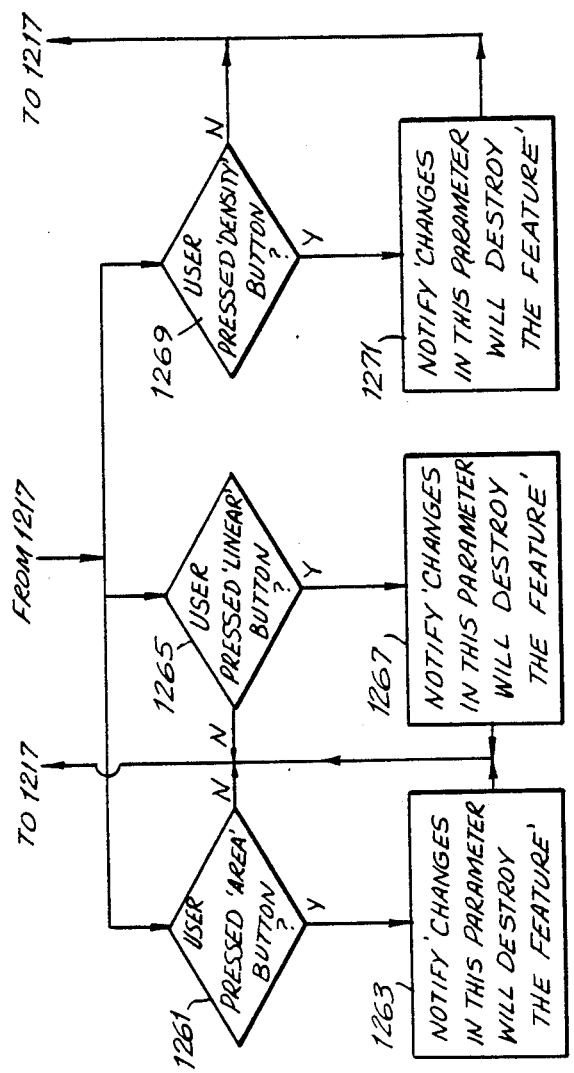

Returning to the flow chart of FIG. 2A, if edit feature button 234 is actuated, as represented by an affirmative answer to inquiry 243, the processor advances to the edit feature routine shown in the flow chart of FIG. 10A. Digressing again, and with reference to the flow chart of FIG. 10A, since a feature may be a discrete valued feature, a continuous valued feature or a scripted valued feature, different routines are provided to edit each of these value types. Advantageously, once the expert has selected a particular value type when creating a new feature, he is not permitted to change that type during an editing operation. As can be seen from the flow chart of FIG. 10A, if a feature selected by the expert for editing is a discrete value type, the processor advances to the edit discrete feature routine depicted by the flow chart of FIG. 10B. Similarly, if the feature selected for editing is a continuous value type, the flow chart of FIG. 10A advances to the edit continuous value routine depicted in FIG. 11A. Finally, if the feature selected for editing is a scripted value type, the processor advances from the flow chart of FIG. 10A to that depicted in FIG. 12A.

Figures 2, 10C:
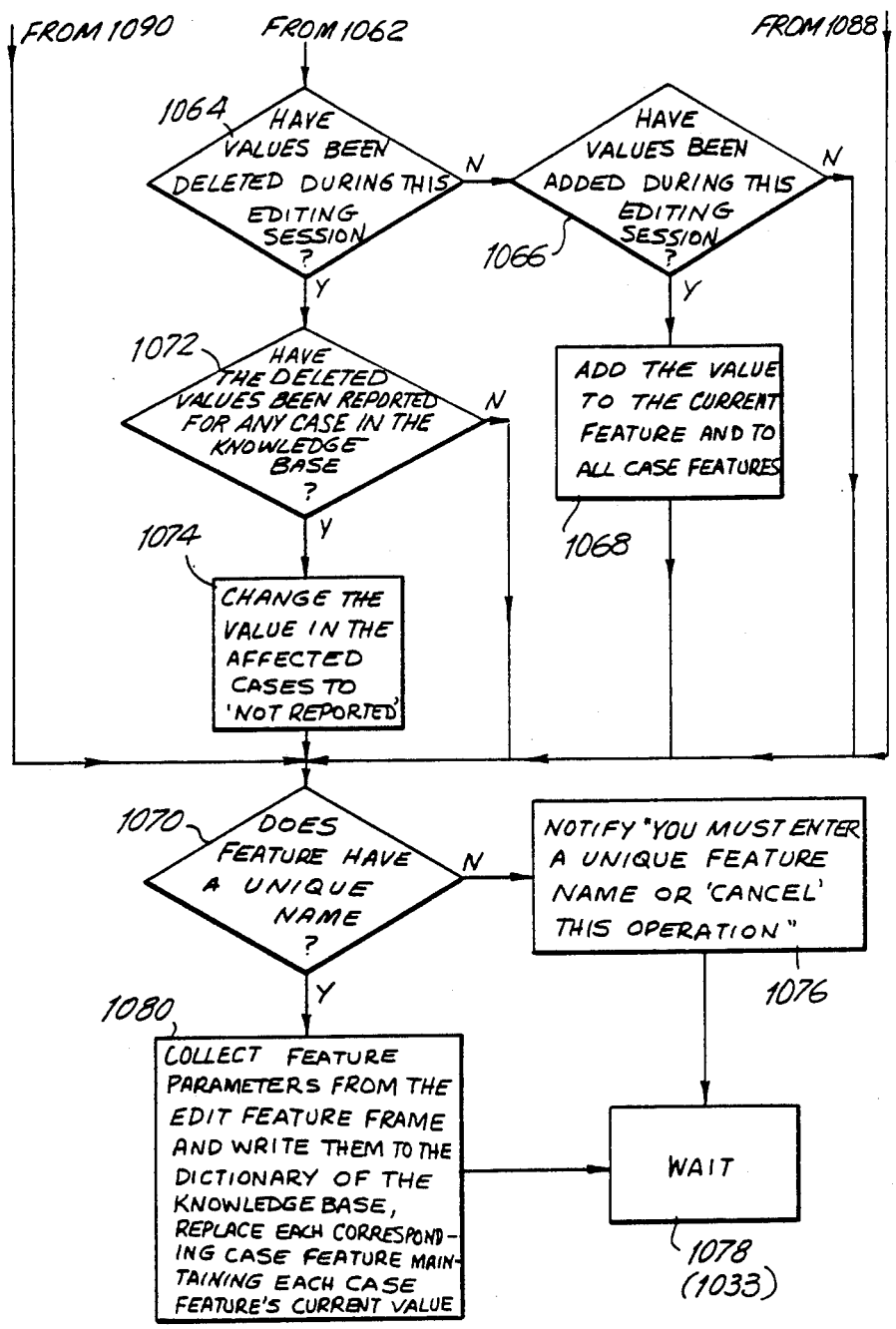

Since the editing of a feature results in a modification in the feature values present in the knowledge base, it is possible that some cases which include the feature being edited will be significantly affected. For example, if a discrete value of a feature is changed, a case having the originally valued feature (i.e. a feature having the value which now is being changed) will be affected. Processor 102 takes this into account, as represented by the flow chart of FIG. 10C, such that the case record stored in the knowledge base is modified to indicate that this now-edited feature has not yet been reported. That is, since the assigned value of this feature in the case record has been changed, the expert is given the opportunity, when reviewing this case, to select another value for this now-edited feature.

Figures 1, 13A:
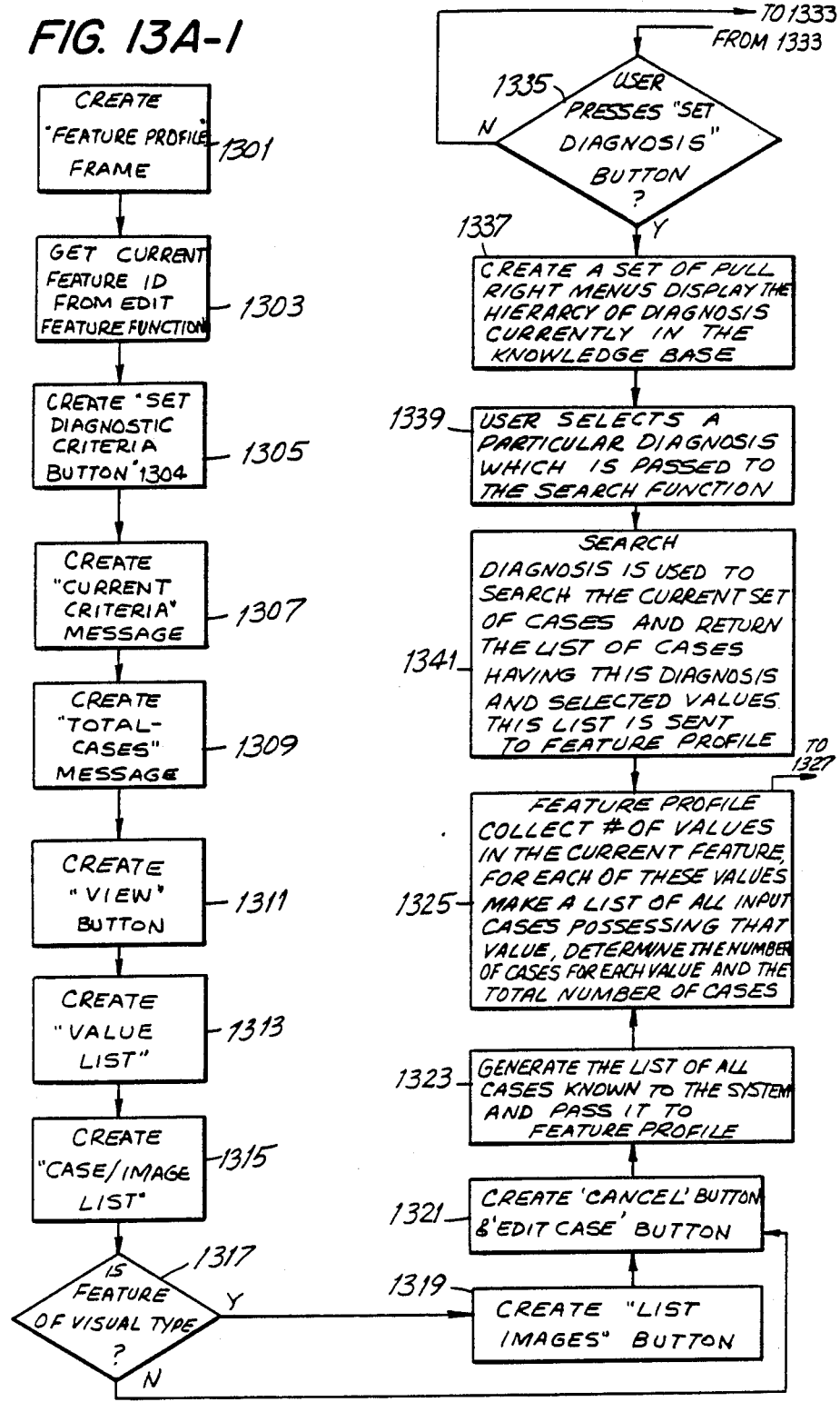
Figures 2, 13A:
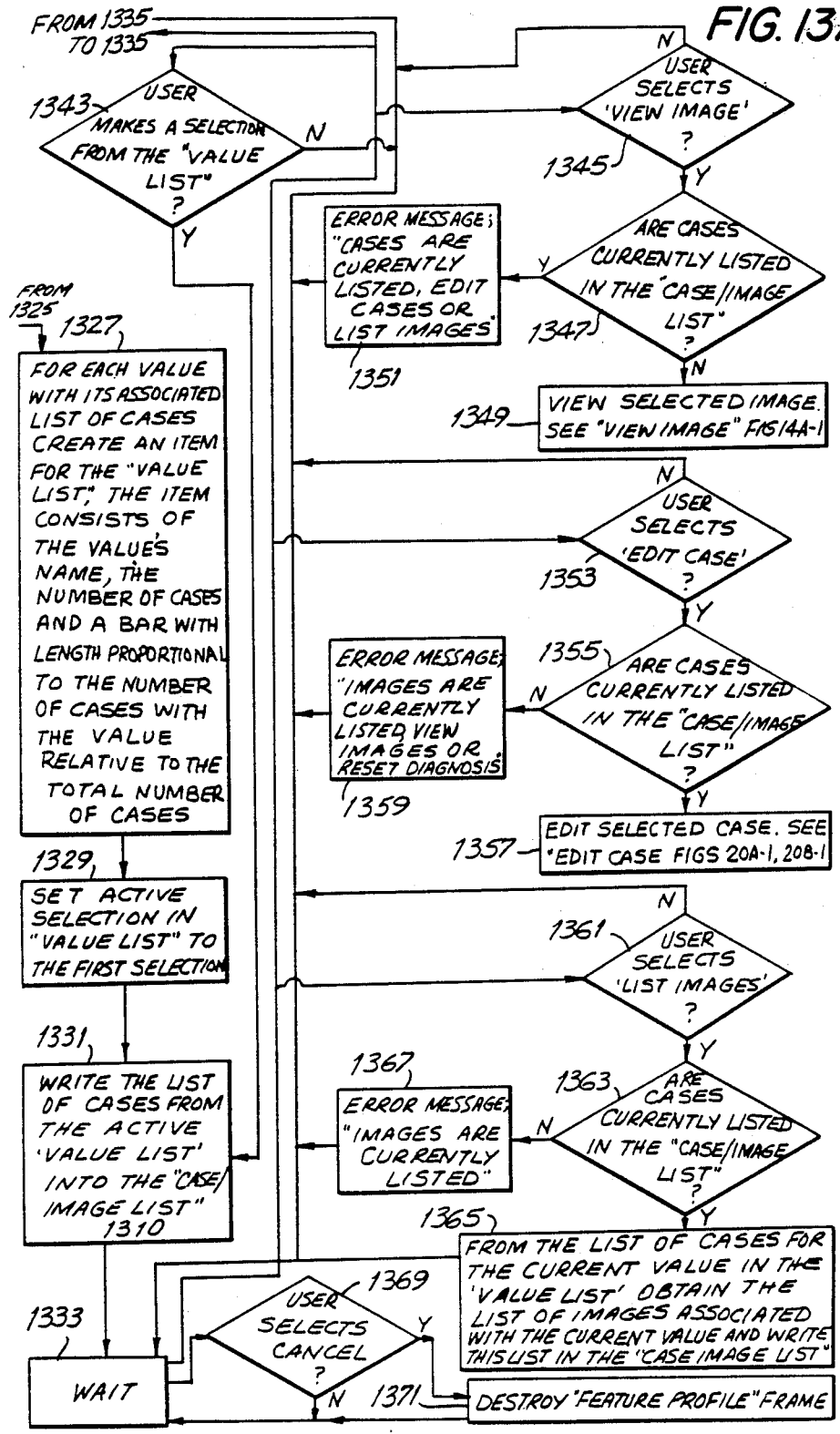
Figure 14:
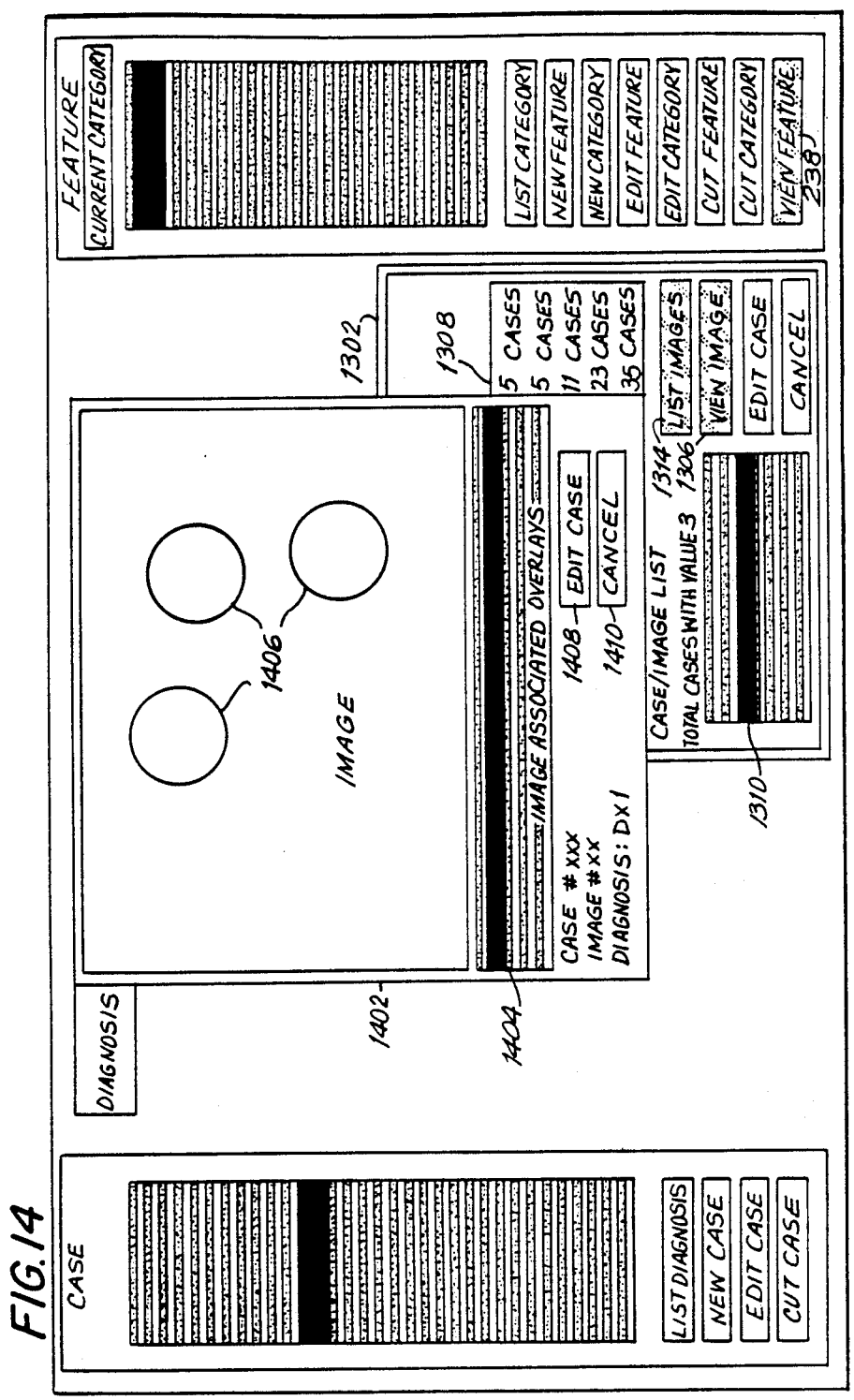
FIG. 14 is a display of images having selected values of a particular feature.
Figure 14A:
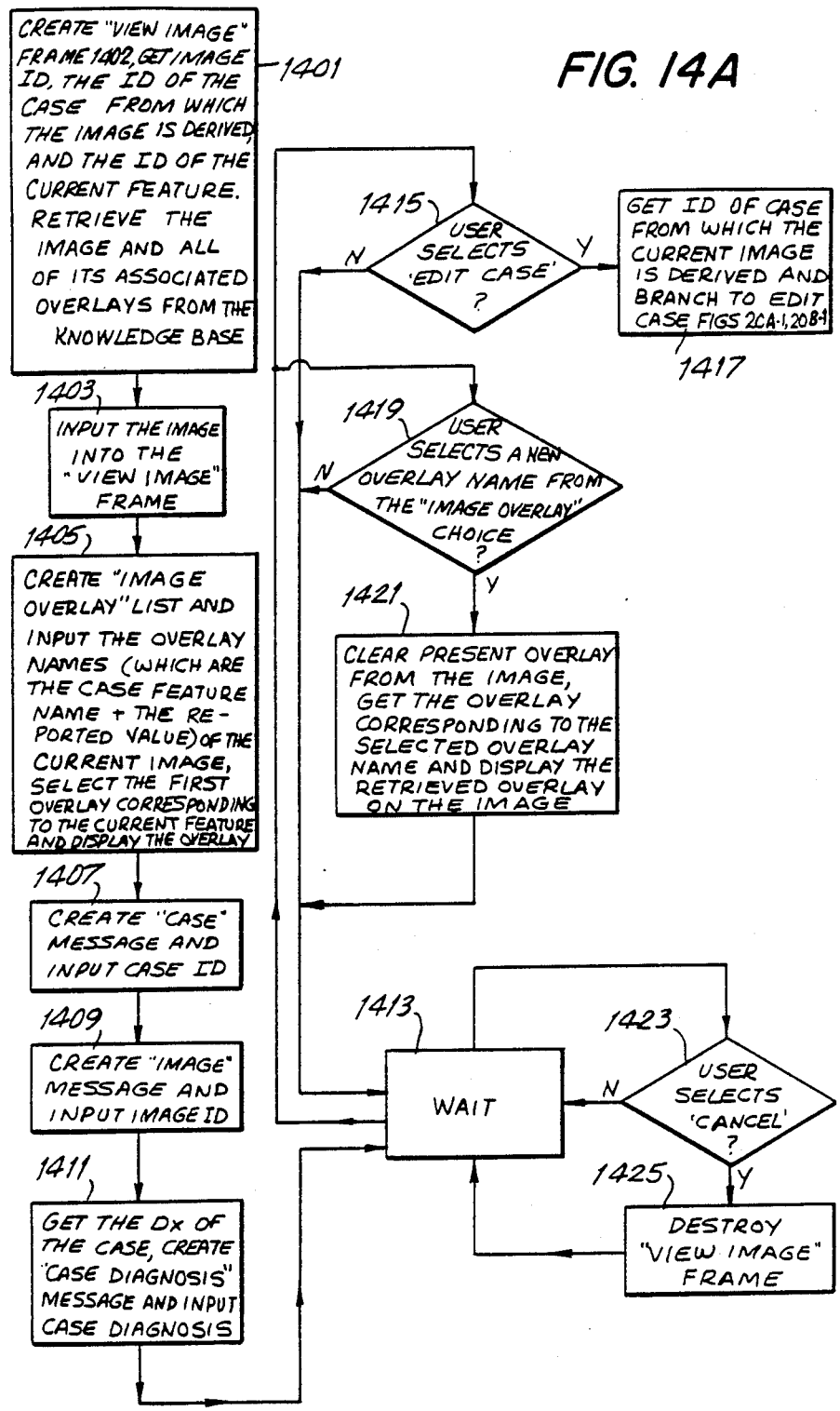
FIG. 14A is a flow chart representing the manner in which the aforementioned image is displayed.

Returning to FIG. 2A, if view feature button 238 is actuated, as represented by an affirmative answer to inquiry 259, the processor advances to the view feature routine illustrated in FIG. 13A. This function enables the expert to observe how this particular feature behaves in, or influences, different diagnoses. Not only is the expert provided with statistical information regarding behavior, as shown by the display screen of FIG. 13, but this view feature function permits the expert to observe that particular feature in different cases. For example, for the feature Pap nuclear border shape, the display screen shown in FIG. 13 indicates to the expert the number of cases in which the nuclear border shape is smooth, the number of cases in which this shape is irregular, the number of cases in which this shape is variable and the number of cases in which this shape has been designated as "other". As will be apparent from the flow chart of FIG. 13A, the expert may observe the pictorial image of a smooth nuclear border in those cases having same. Likewise, the expert may observe the pictorial image of an irregular nuclear border as it appears in different cases, or he may observe the pictorial image of a variable nuclear border in other cases. The flow chart of FIG. 14A, which is reached from the flow chart of FIG. 13A, depicts how this viewing of an image is carried out, and FIG. 14 illustrates a display screen of what is viewed by the expert.

Figure 16A:
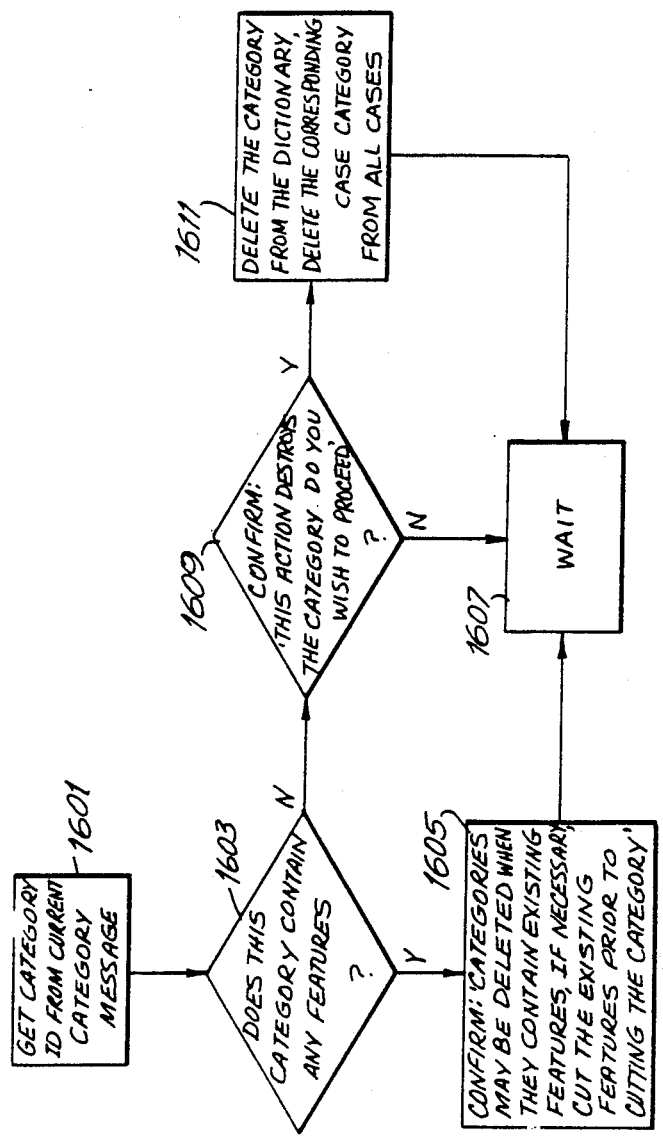
FIG. 16A is a flow chart representing the manner in which a selected category is deleted.

Returning again to FIG. 2A, if cut feature button 240 is actuated, as represented by an affirmative answer to inquiry 251, the processor advances to the cut feature routine illustrated in FIG. 15A. Finally, if cut category button 242 is actuated, as represented by an affirmative answer to inquiry 255, the processor advances to the flow chart of FIG. 16A.

It is appreciated that, depending upon the particular function to which the processor has advanced, as selected by the expert, the specific operations that may be carried out for that function, as illustrated in the aforementioned flow charts, may be executed.

Figures 1, 17:
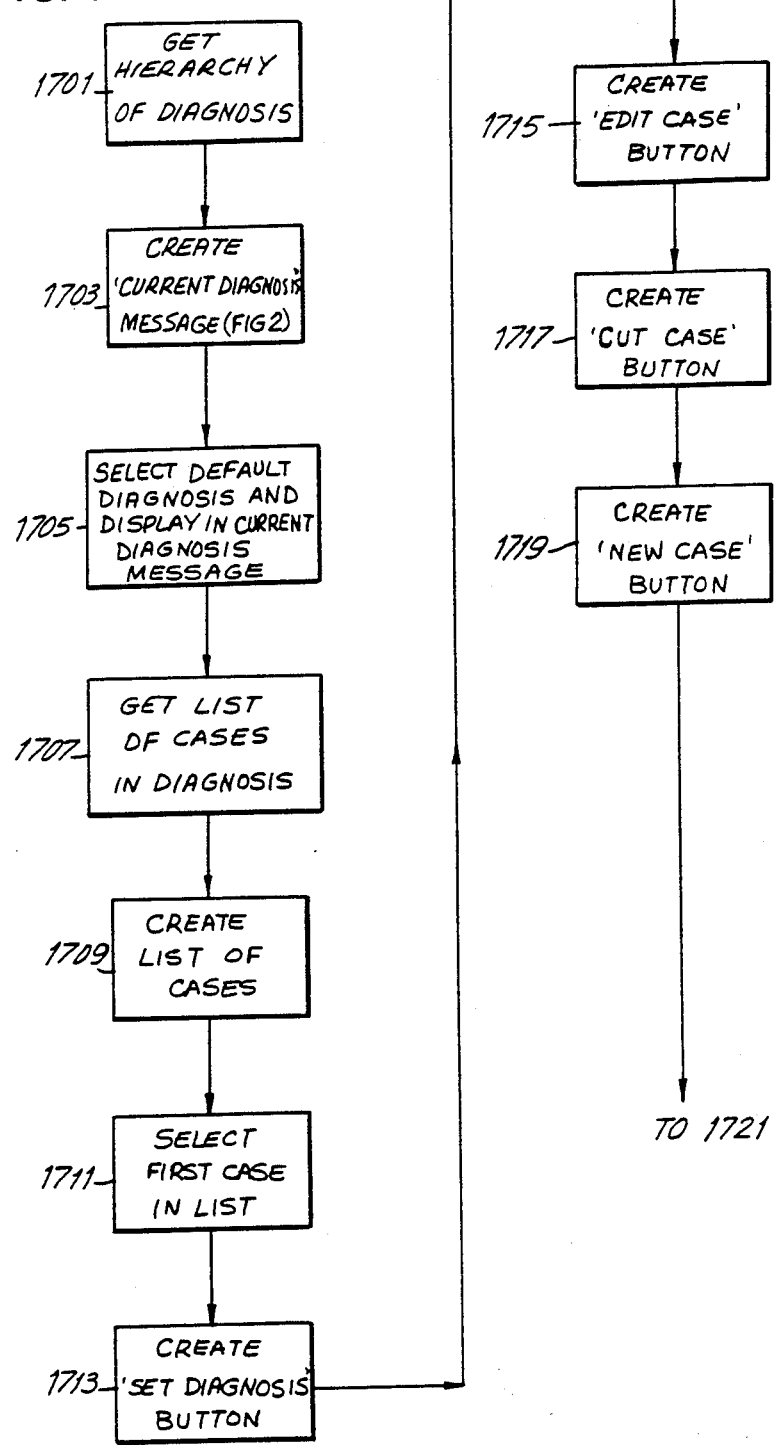
Figures 2, 17:
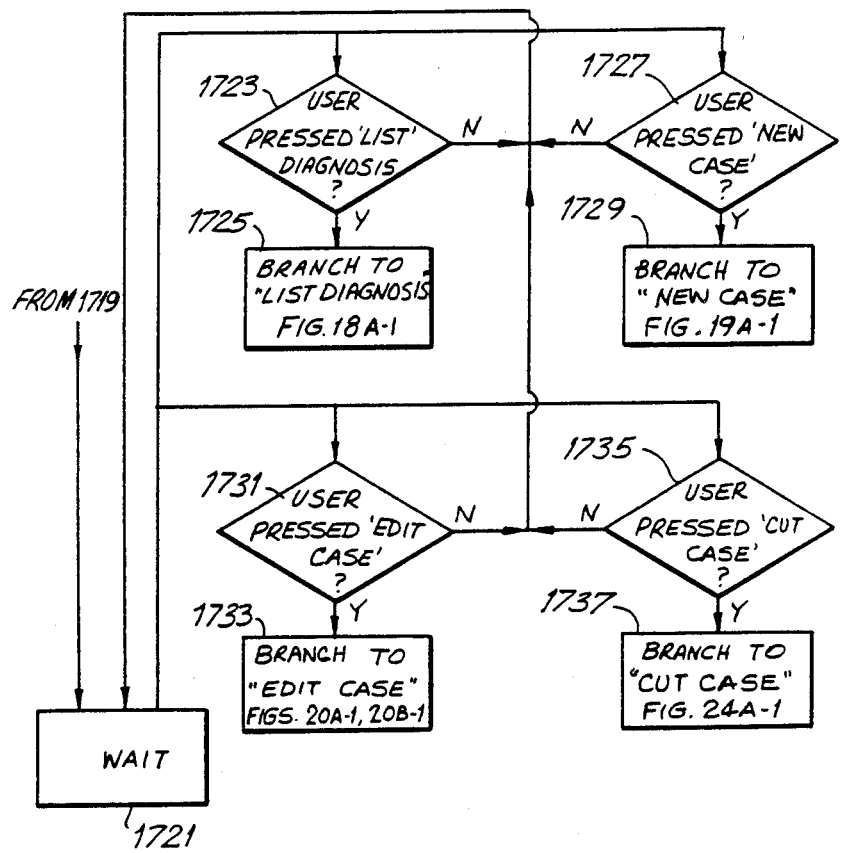

While FIG. 2A illustrates the flow chart by which feature window 220 is created, a similar flow chart is illustrated in FIG. 17 to depict the manner in which case window 202 is created and utilized by the expert. Turning briefly to FIG. 17, the case window 202 illustrated in the home screen of FIG. 2 is created as follows: the processor advances to instruction 1701, whereby the hierarchy of diagnoses stored in the knowledge base is retrieved, and as represented by instructions 1703 and 1705, a default diagnosis, such as a predetermined one of the diagnoses in the highest level of the hierarchy, is selected and displayed as current diagnosis message 260 (FIG. 2). The hierarchy of diagnoses has been described above and is best illustrated in the diagnoses tree shown in FIG. 26.

The processor retrieves from the knowledge base all of the case records in which a current diagnosis (i.e. current diagnosis 260) is present, as represented by instruction 1707. The processor then advances to instruction 1709 which lists these cases in case list 204. Thereafter, the processor selects a default case in this list, as represented by instruction 1711, this selected case being depicted in FIG. 2 as selected case 206. Then, the processor advances to instructions 1713, 1715, 1717 and 1719 by which list diagnosis button 208, new case button 210, edit case button 212 and delete case button 214 are created. The processor now awaits the actuation of one of these buttons.

Figure 18A:
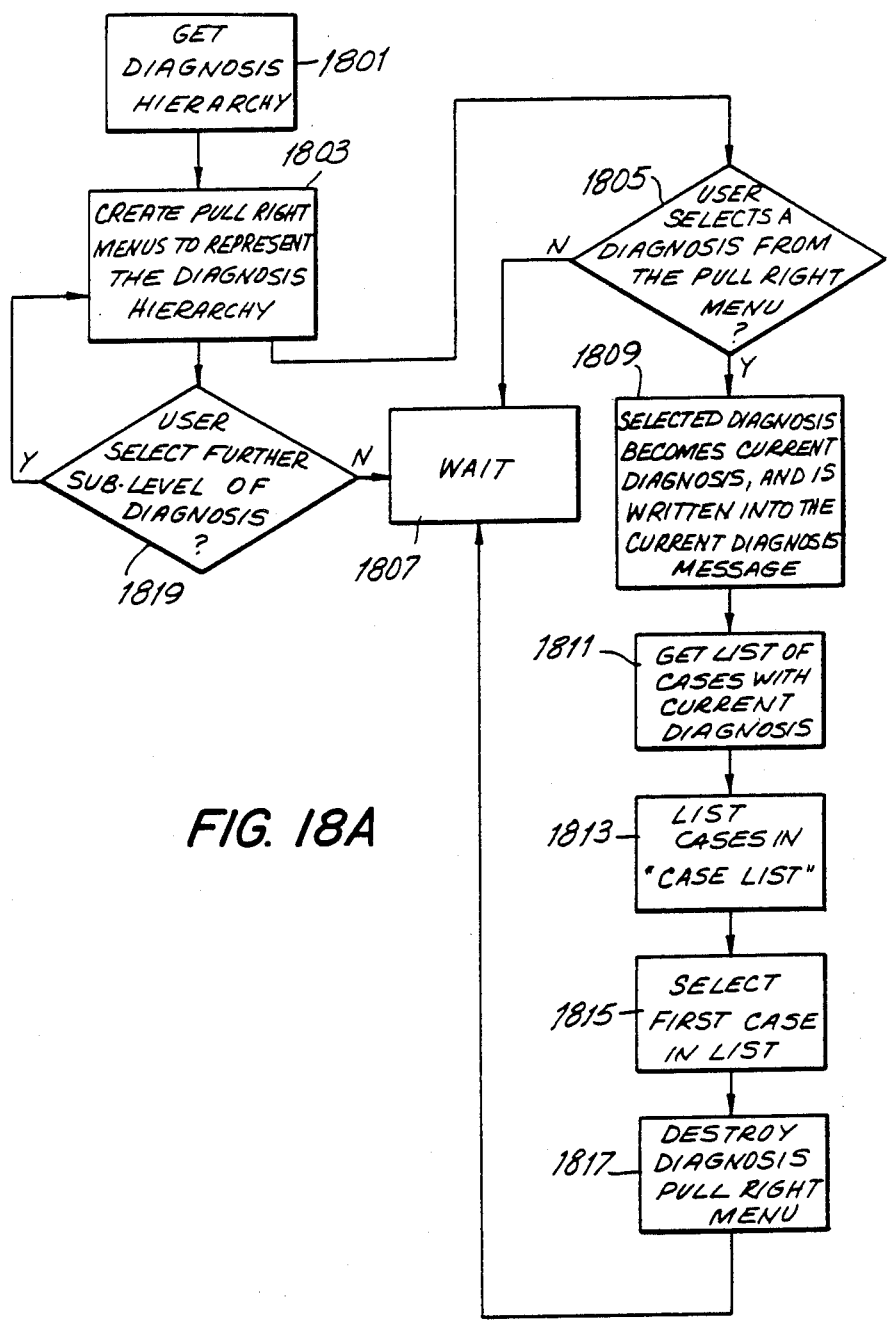
FIG. 18A is a flow chart representing the manner in which the display of FIG. 18 is created.

If button 208 is actuated, as represented by an affirmative answer to inquiry 1723, the processor advances to the list diagnosis function represented by the flow chart shown in FIG. 18A. This function effectively enables the expert to select a desired diagnosis within the diagnoses tree. The selected diagnosis is identified as current diagnosis 260.

Figures 2, 19A:
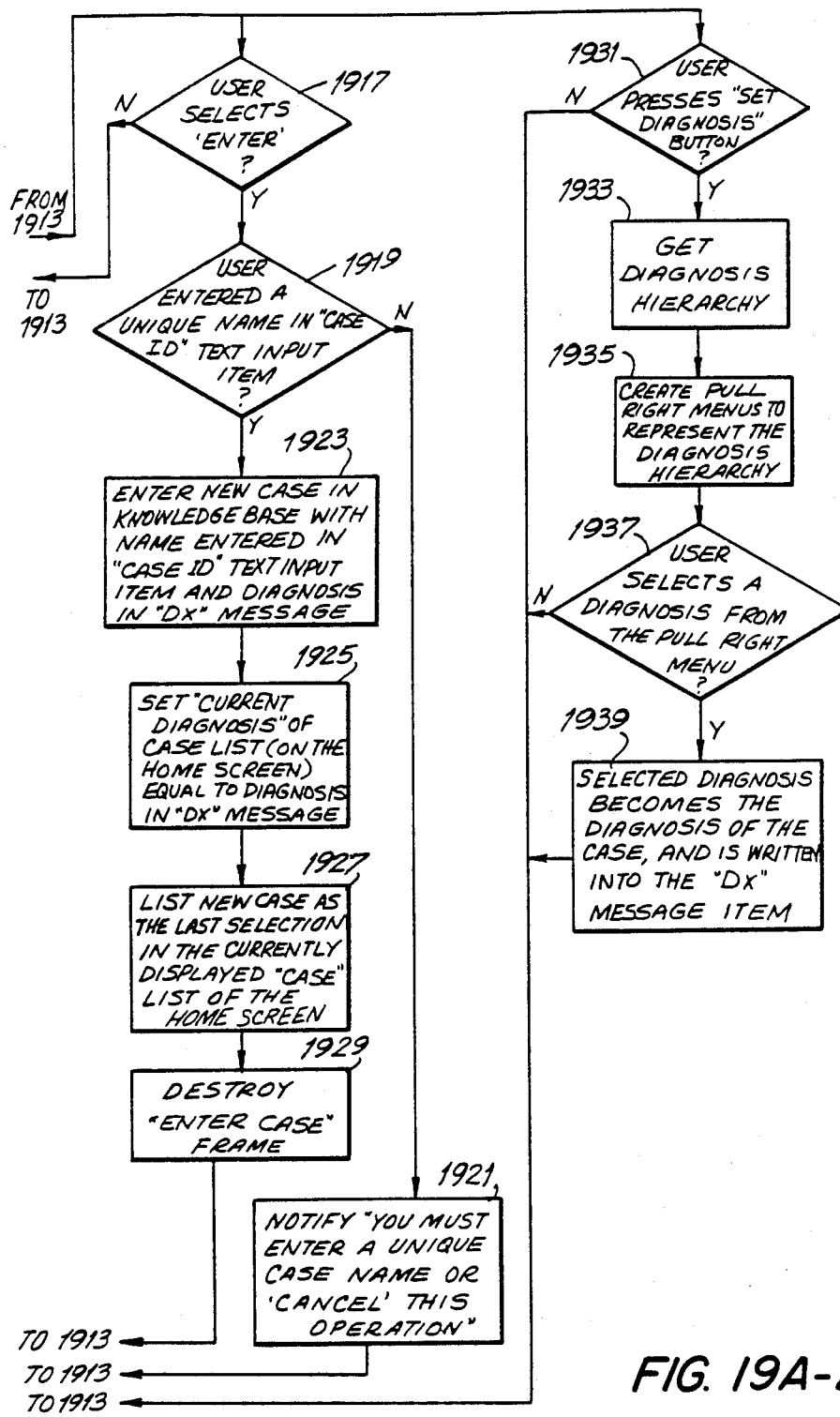

If new case button 210 is actuated, as represented by an affirmative answer to inquiry 1727, the processor advances to the new case function illustrated by the flow chart of FIG. 19A. As is apparent therein, this function is used to create a case record having a particular diagnosis which the expert finds is exemplified by this case.

Figures 1, 20A:
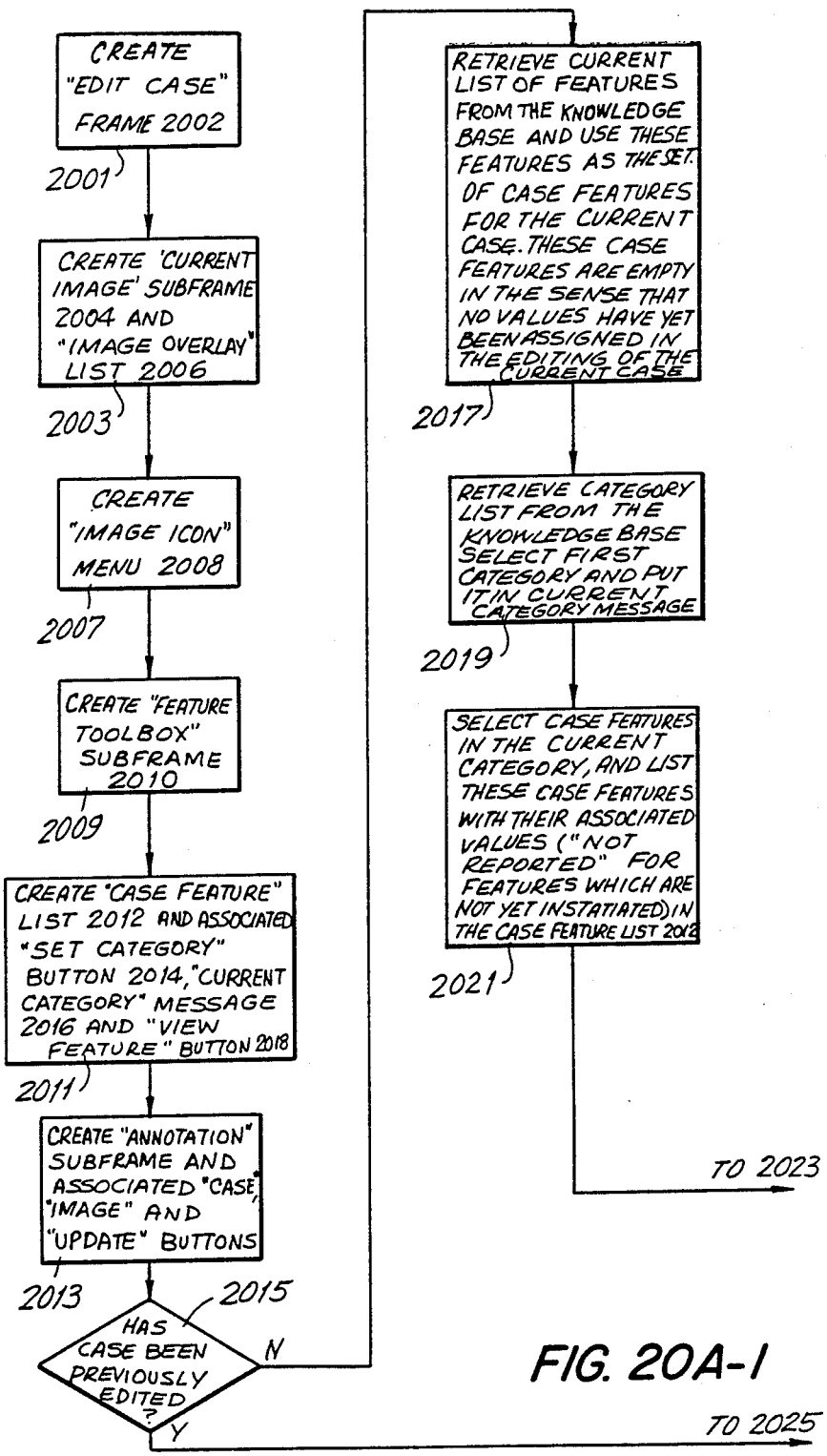
Figures 2, 20A:
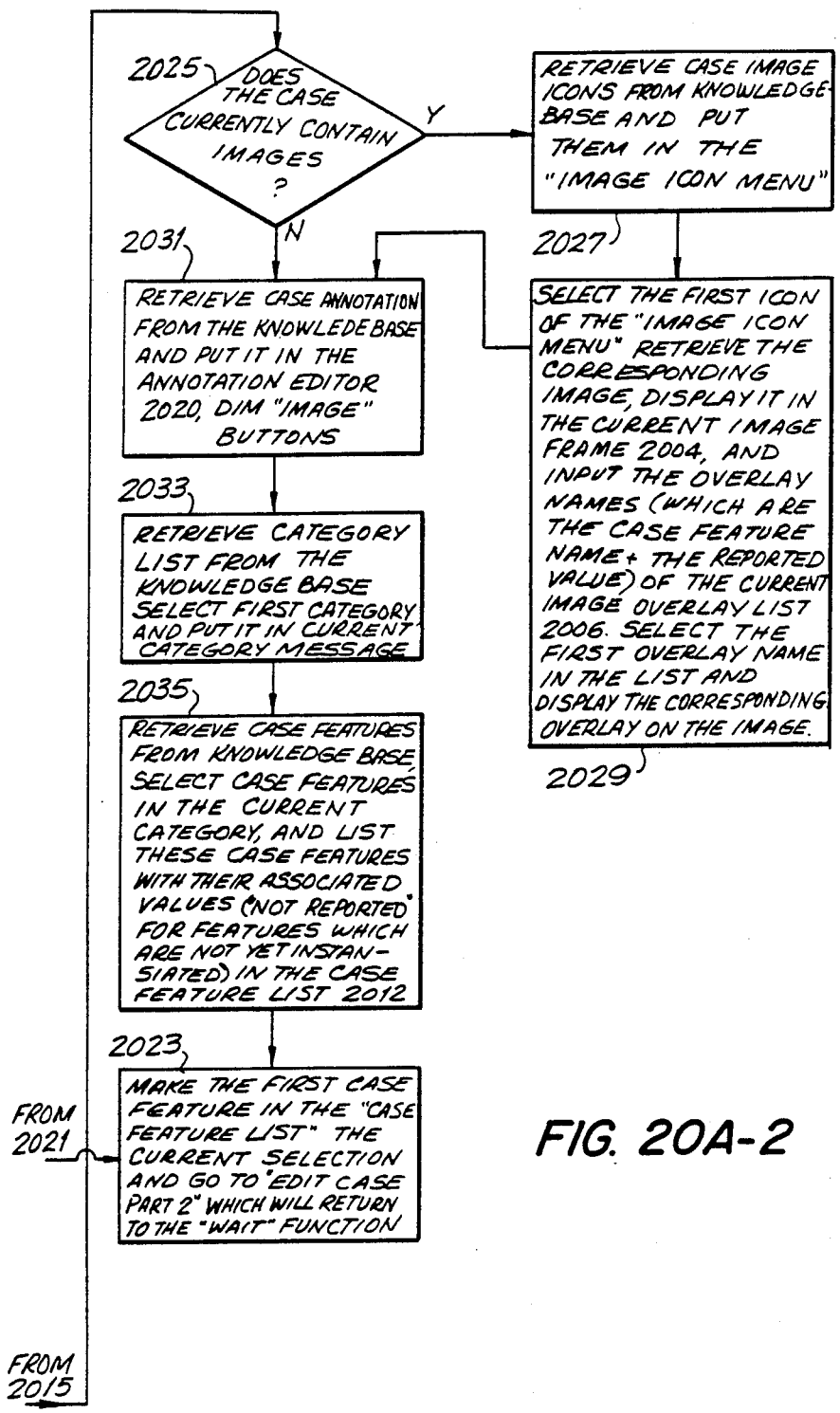
Figures 1, 20B:
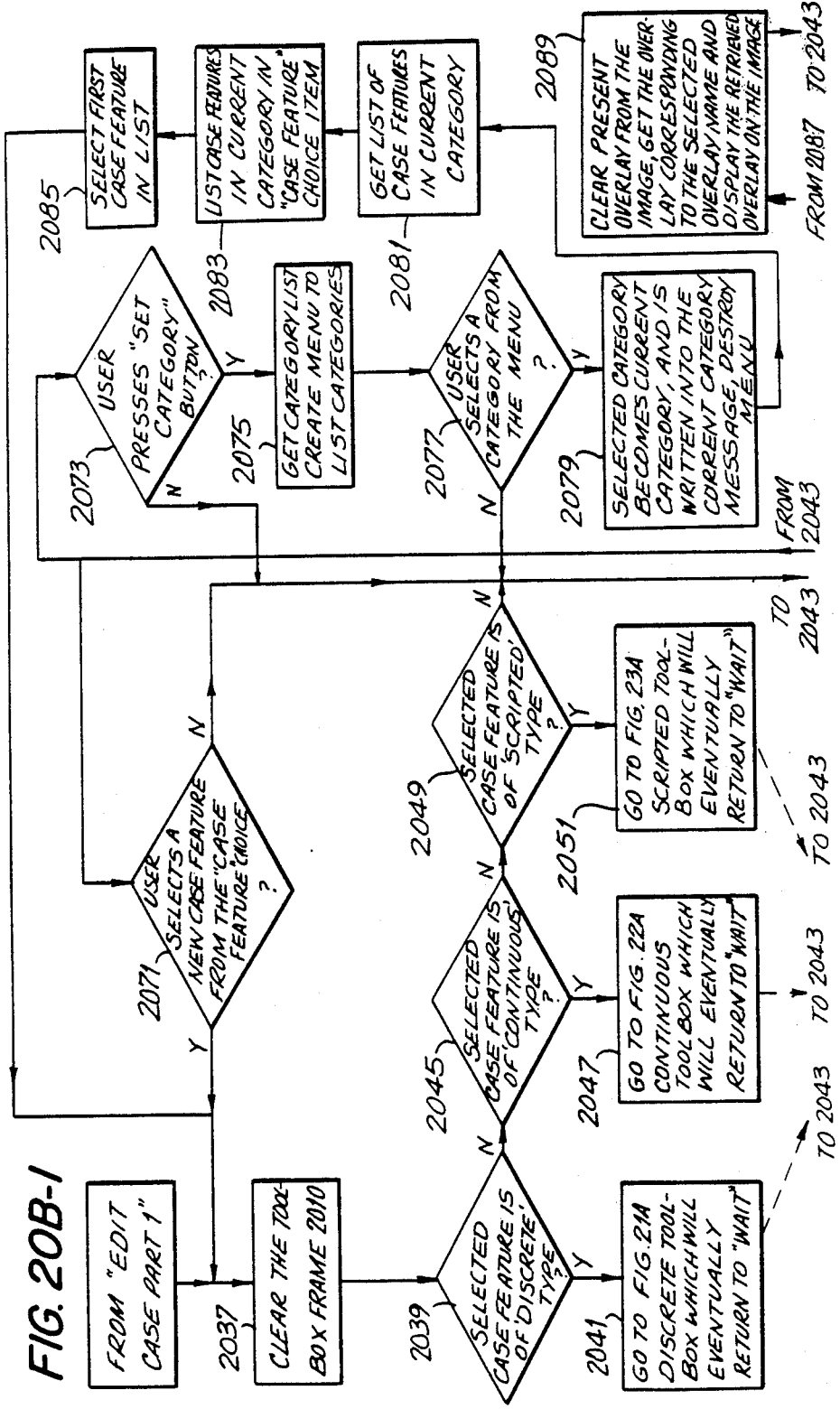
Figures 2, 20B:
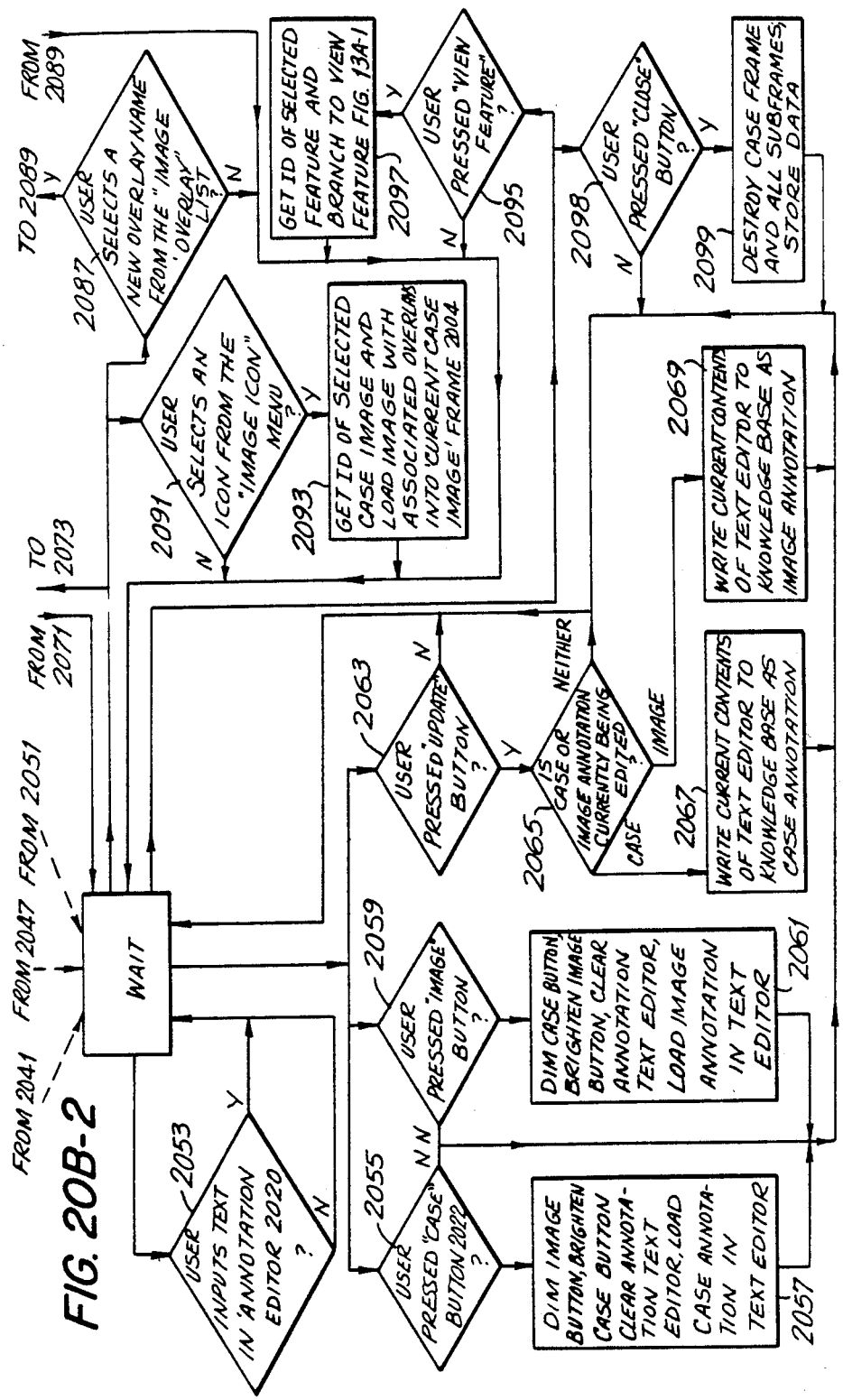

If edit case button 212 is actuated, as represented by an affirmative answer to inquiry 1731, the processor advances to the edit case function illustrated by the flow charts of FIGS. 20A and 20B. This function is used by the expert in assigning values to the features observed in this case. The observation generally is one of pictorial images; and it is the edit case function which provides the facility to link overlays to clearly illustrate particular features in the case. One or more (usually several) pictorial images are selected and linked to the case; and those images which best depict a particular feature are linked with overlays. The expert may link more than one overlay to a particular pictorial image; and overlays illustrating different features may be linked to the same image.

The edit case function is used by the expert not only to create a new case record but to modify an existing case record. This tool is used advantageously by the expert to assure consistency in his observations, characterizations of features and conclusions. Hence, differences in the value of a feature that might arise because of subjective observations are effectively obviated. What had been observed by the expert some time ago as "few" atypical cells and is now characterized as "moderate" atypical cells may be modified such that the expert's observations remain consistent. What is "few" today might not have been "few" previously.

Figures 1, 21A:
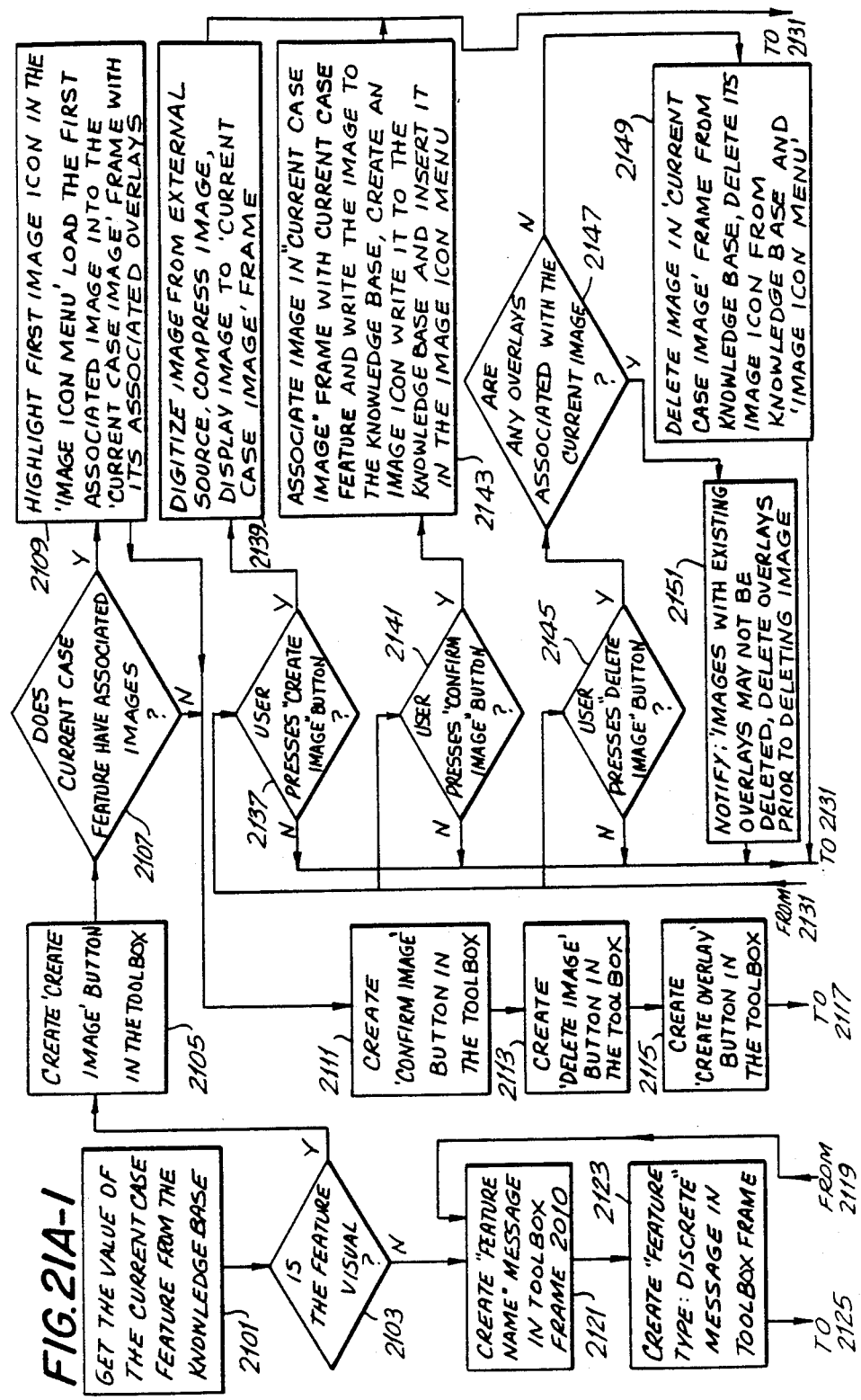
Figures 1, 21B:
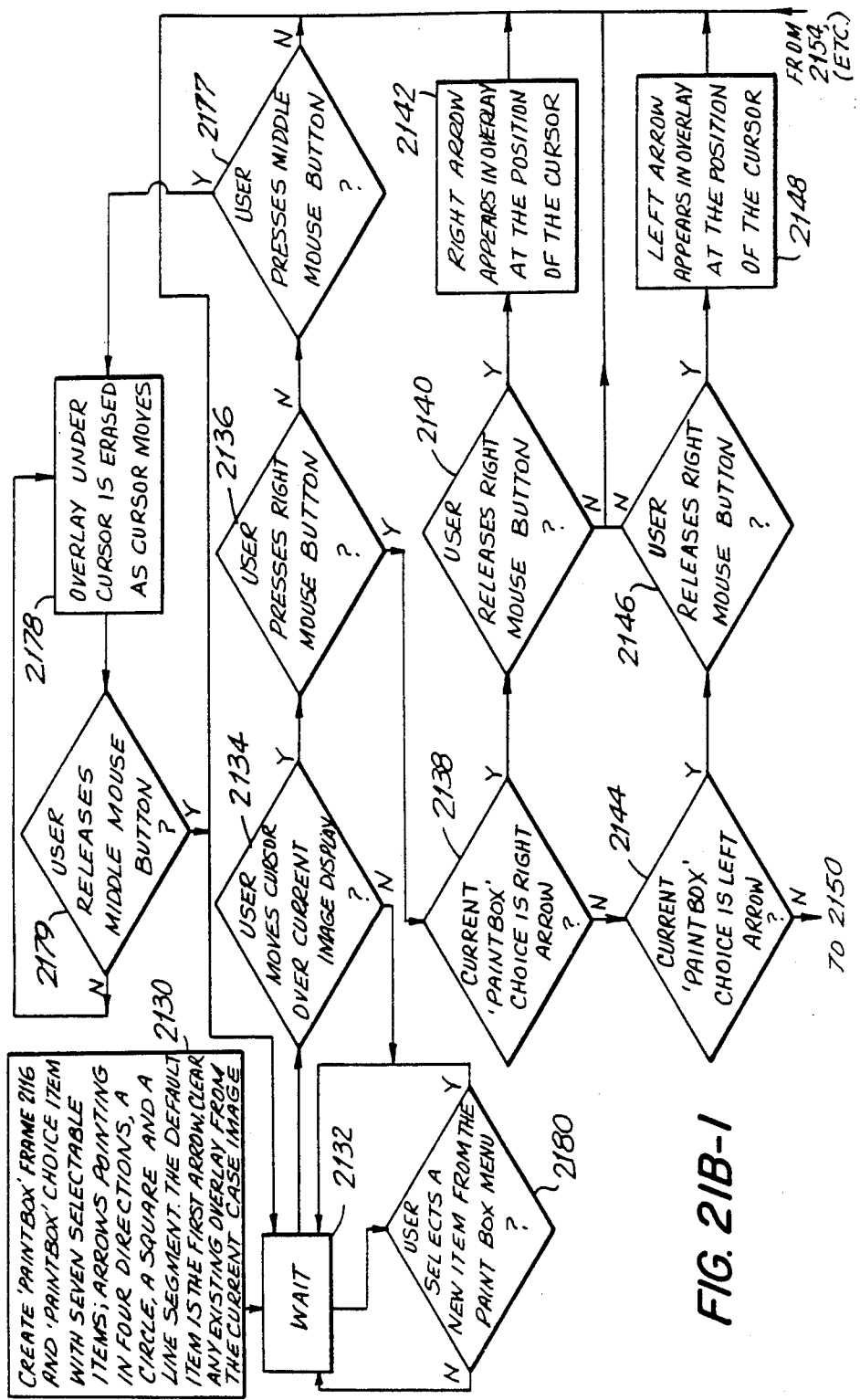
Figures 2, 21B:
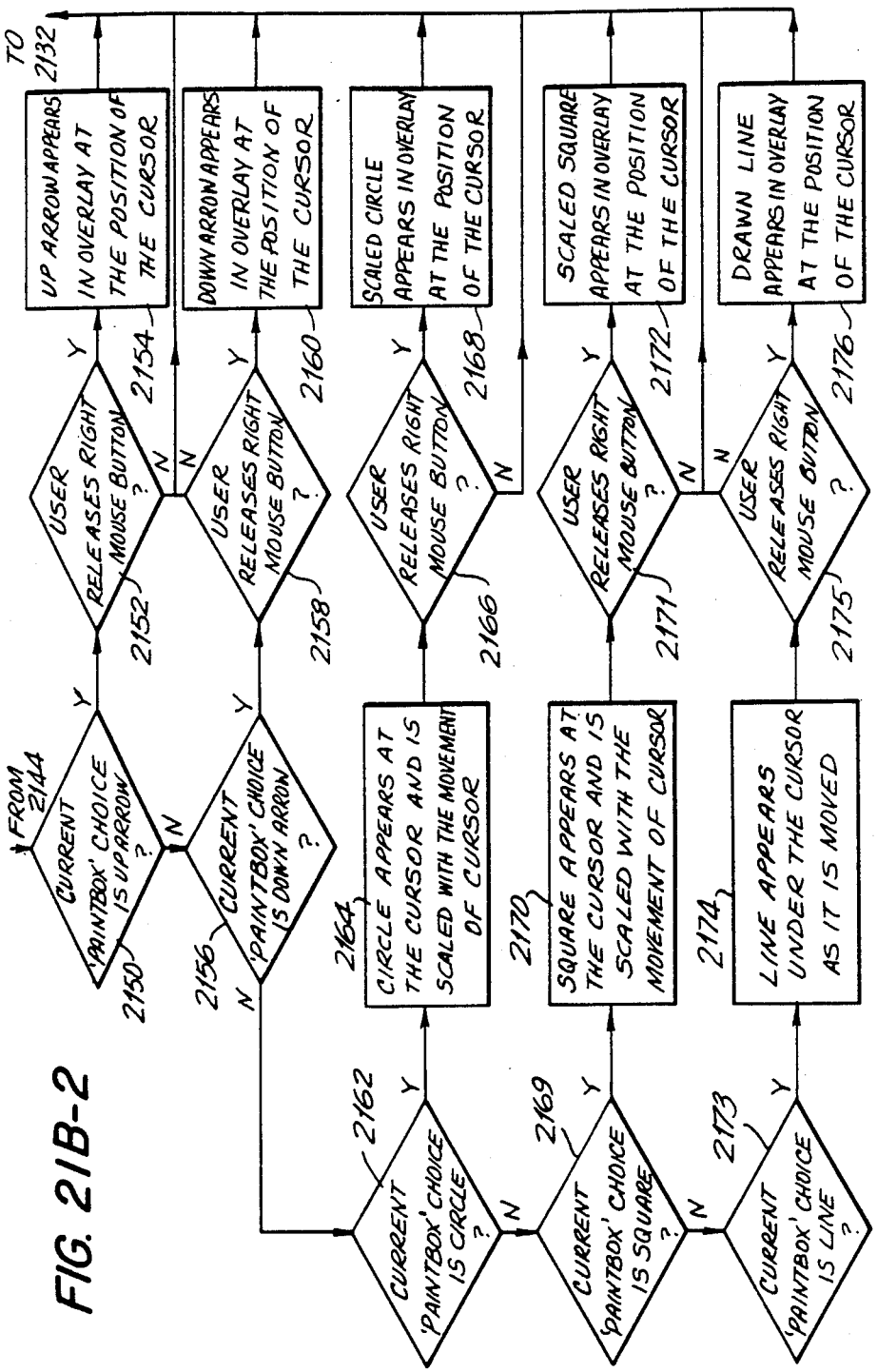

As shown by the flow charts of FIGS. 20A and 20B, slightly different "tools" are used to edit discrete features, continuous features, and scripted features in a case record. These tools are manipulated by the processor under user control, as depicted by the flow charts of FIGS. 21A and B, 22A and 23A.

Figure 24A:
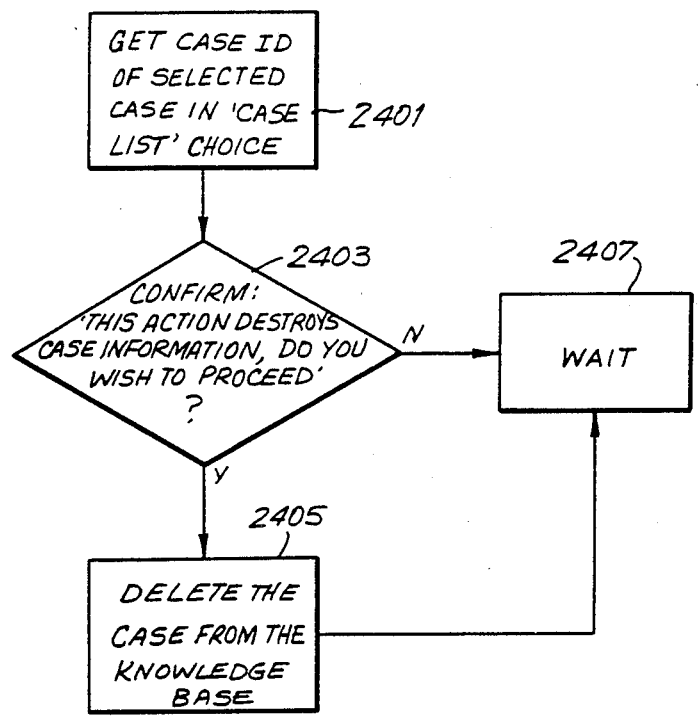
FIG. 24A is a flow chart representing the manner in which a case is deleted.
Figure 25:
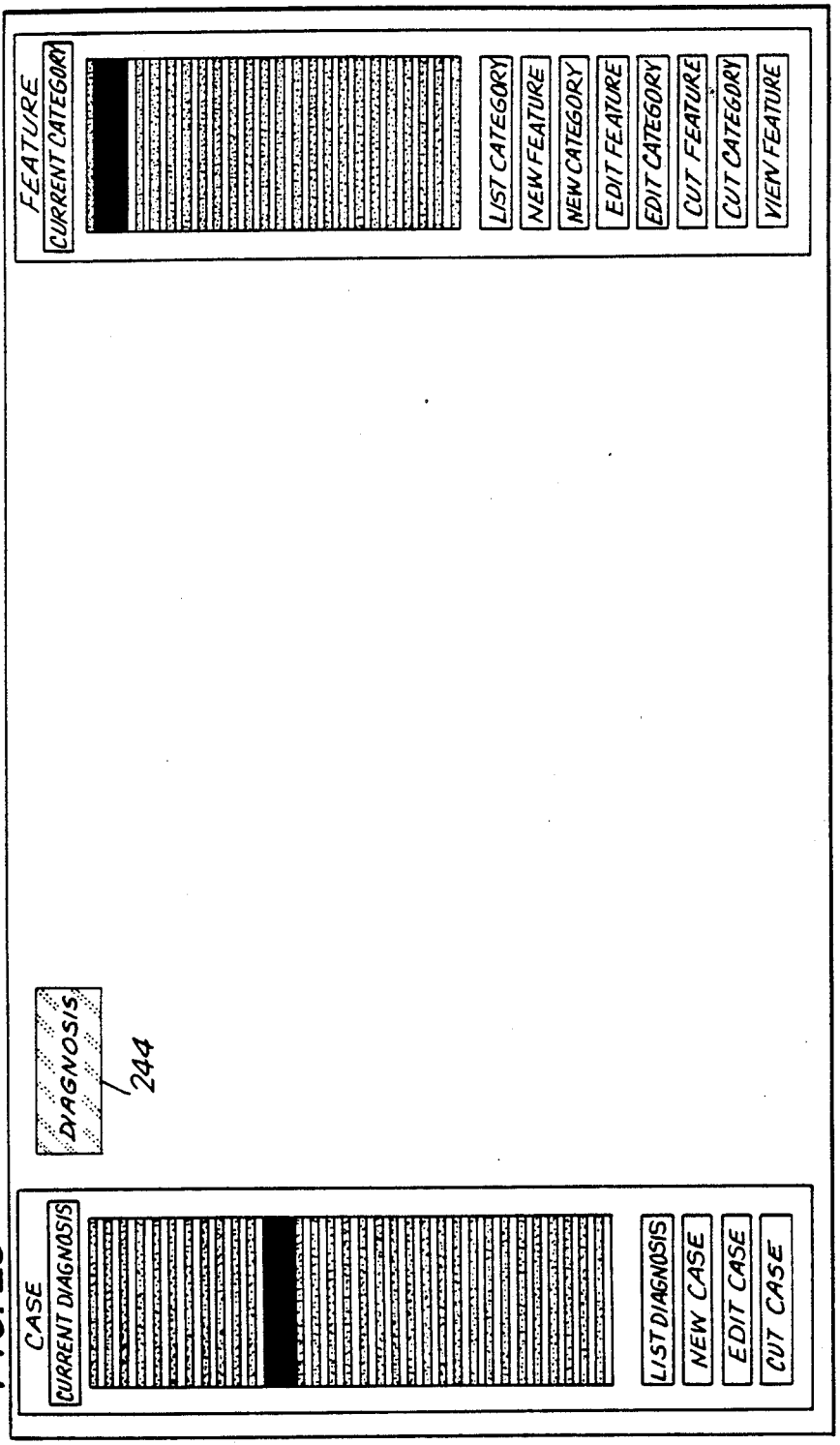
FIG. 25 is a display used in selecting a diagnosis function.
Figure 26:
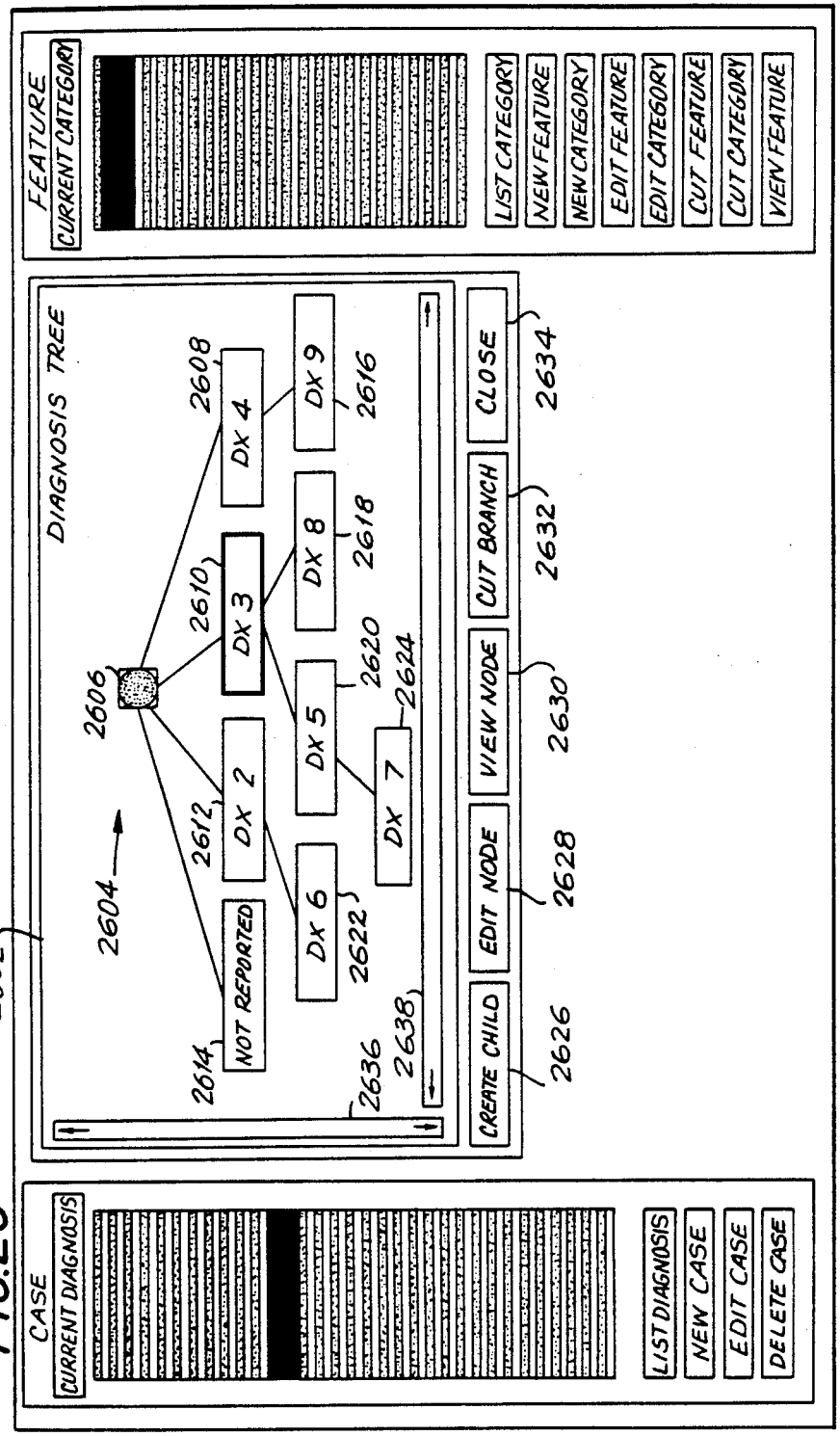
FIG. 26 is a display used in selecting a diagnosis tree.
Figures 1, 26A:
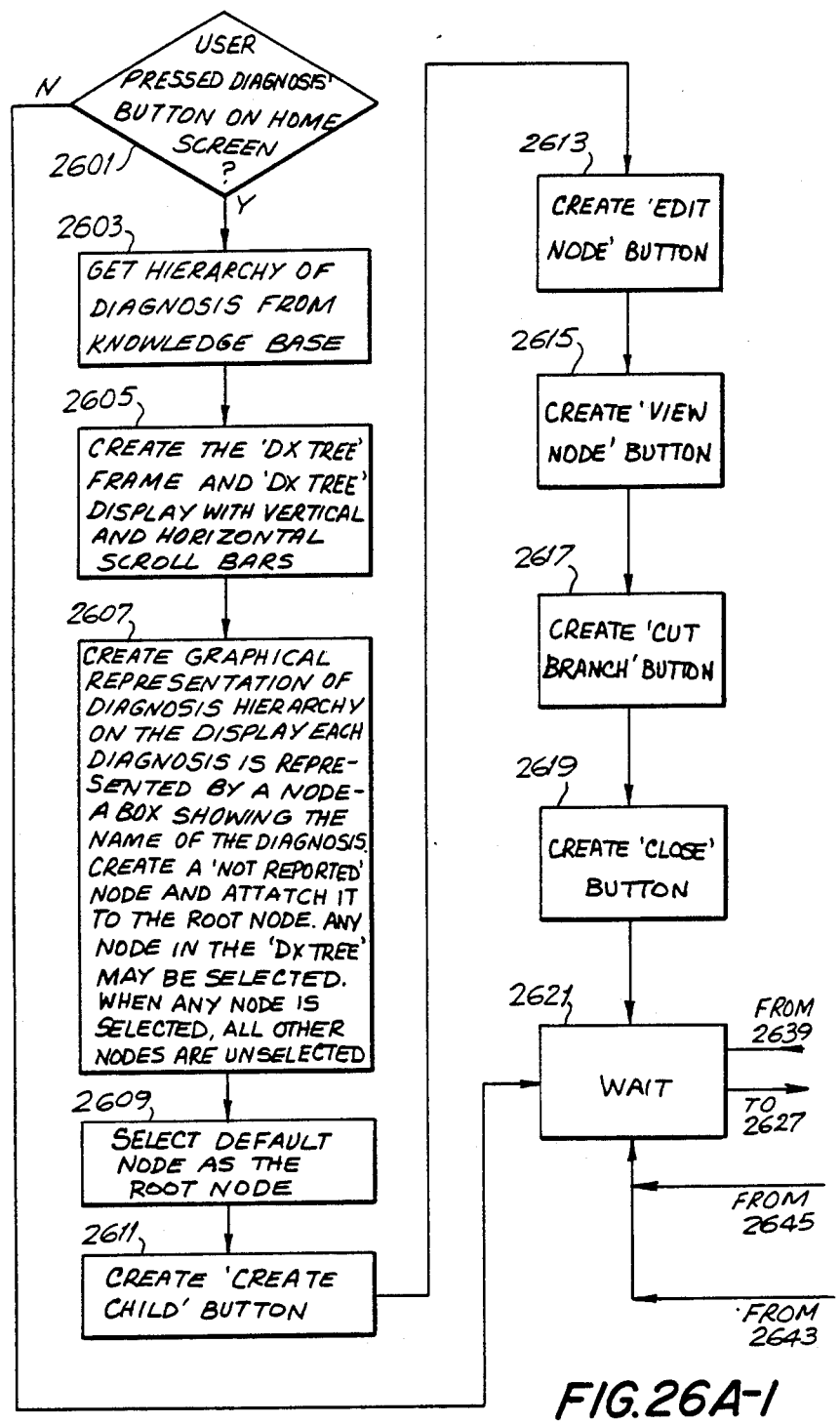
Figures 2, 26A:
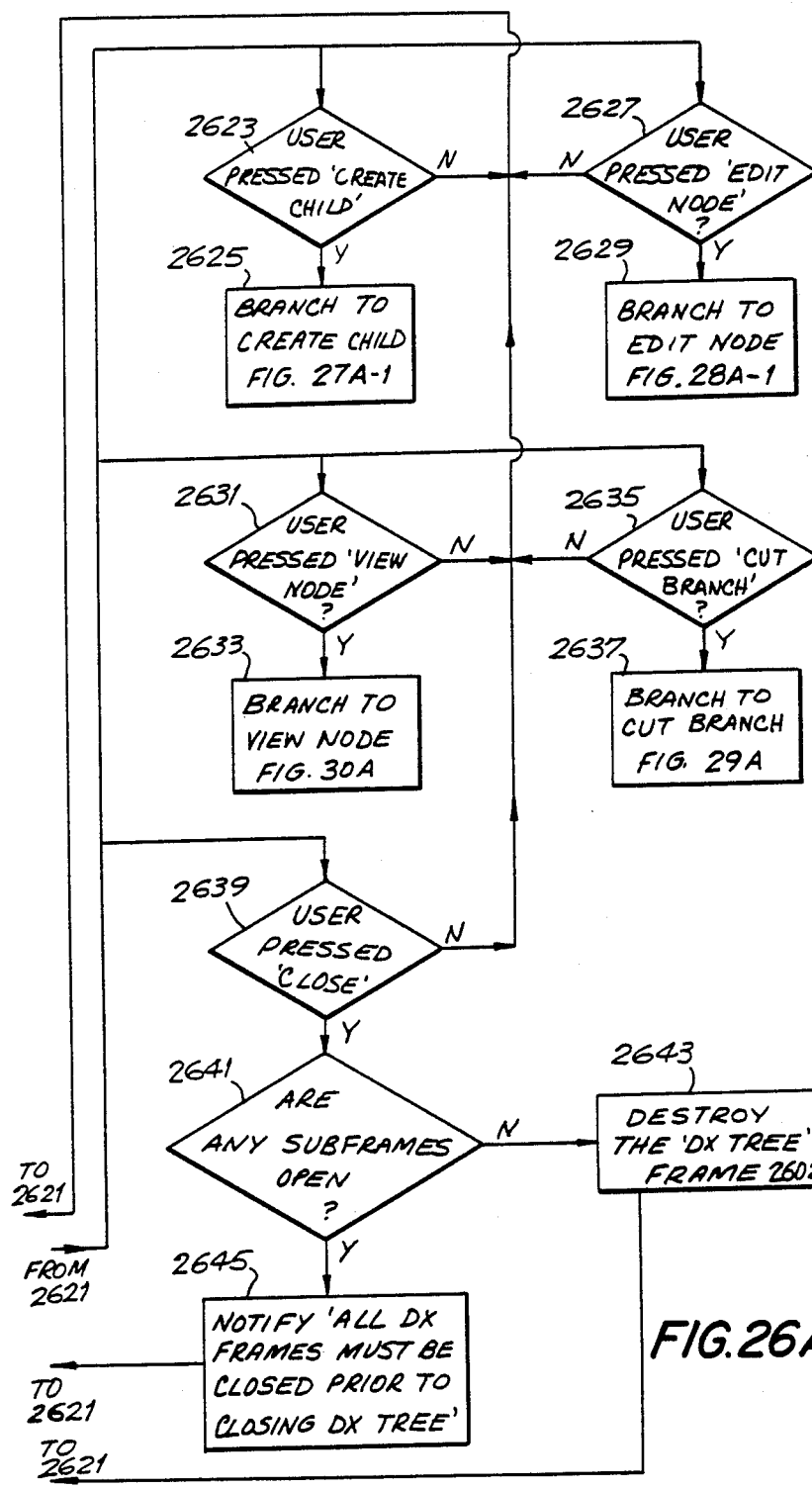
Figure 27:
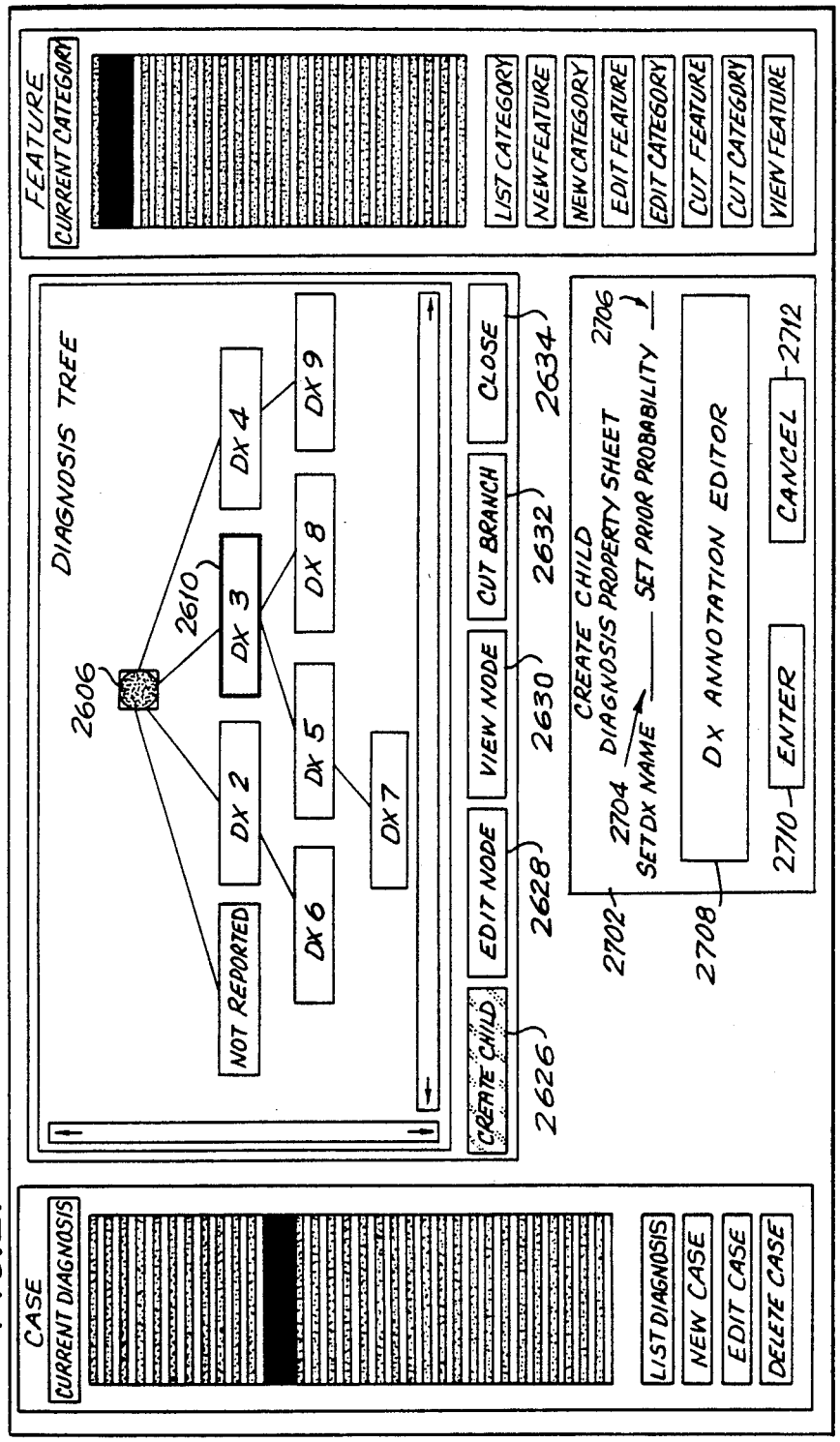
FIG. 27 is a display used in creating a "child" diagnosis node.
Figure 27A:
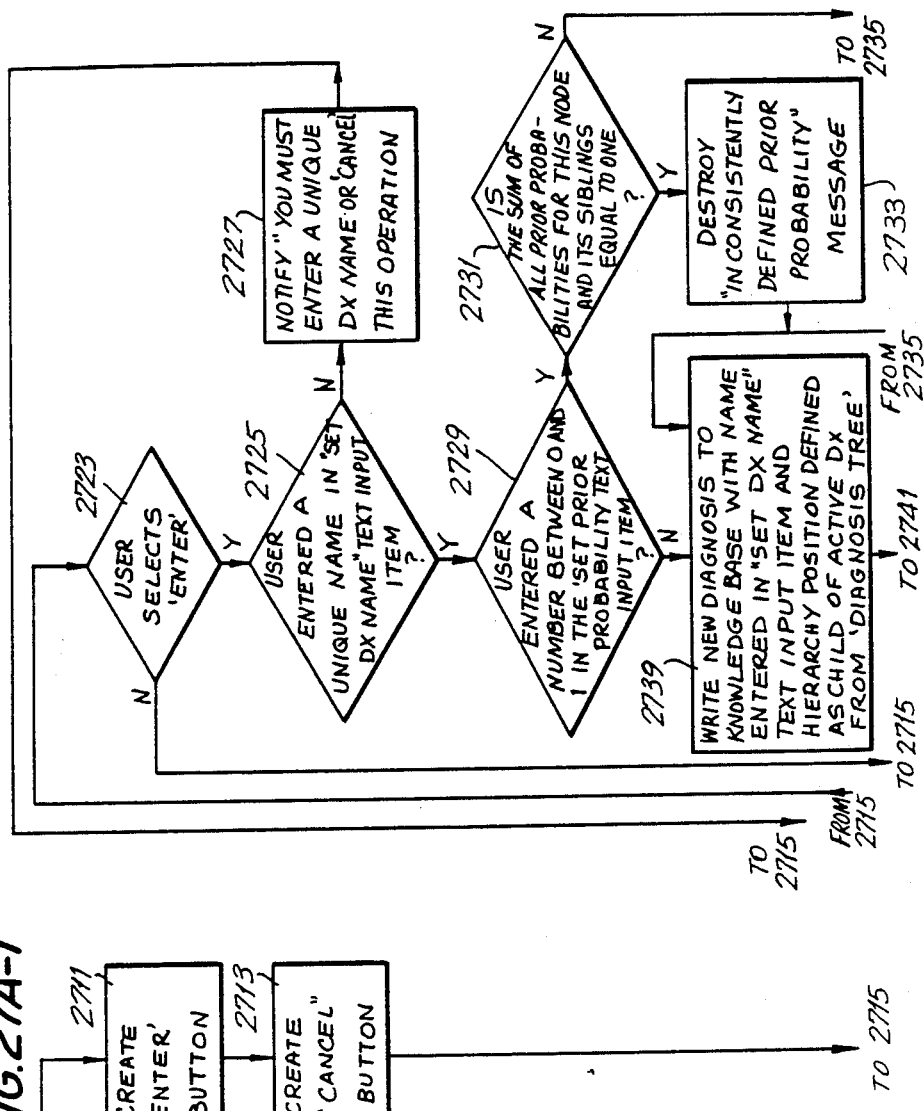
Figure 1:
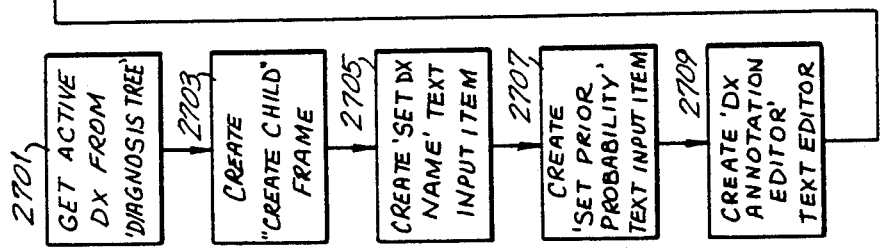
Figures 2, 27A:
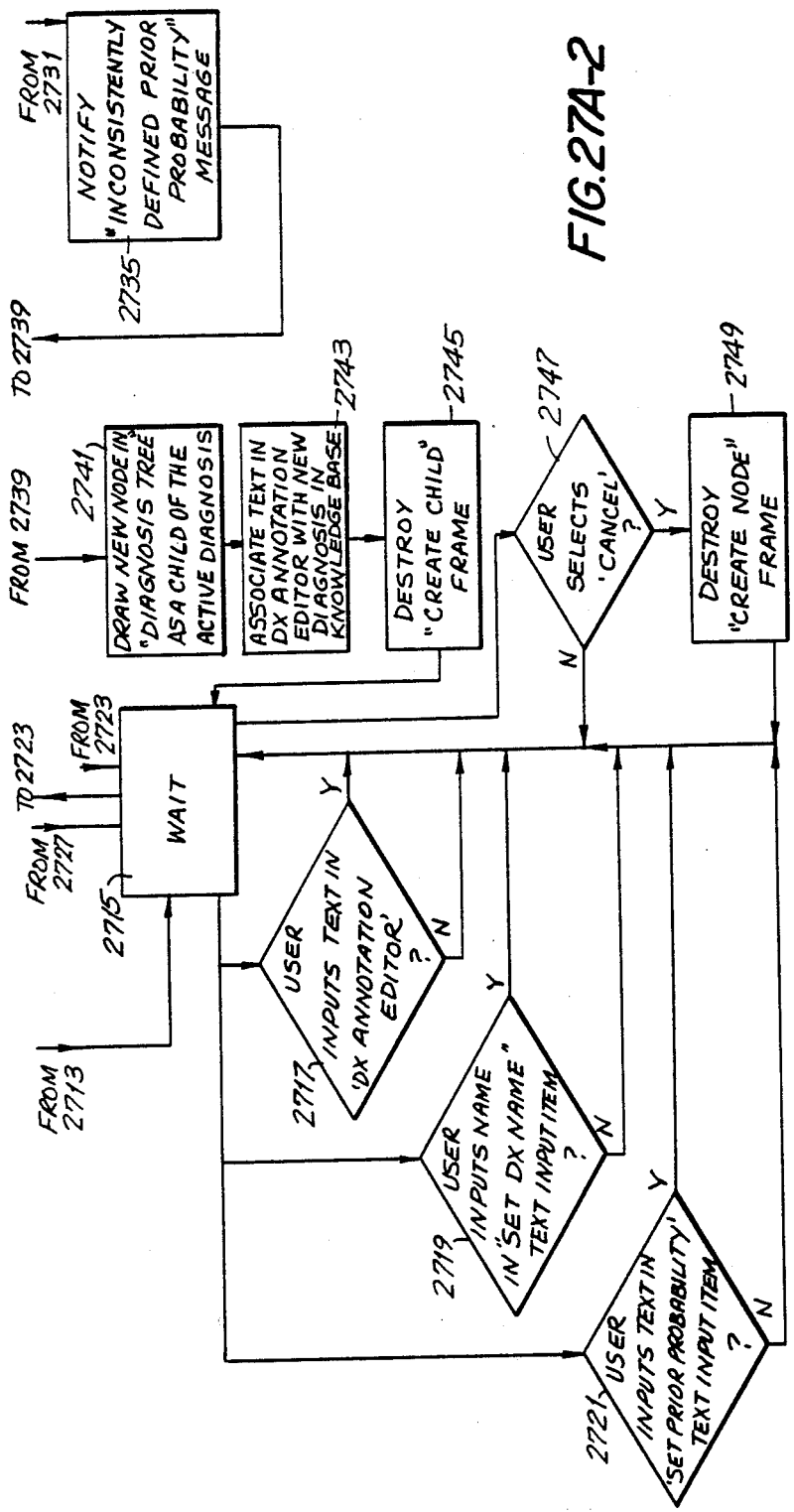
Figure 28:
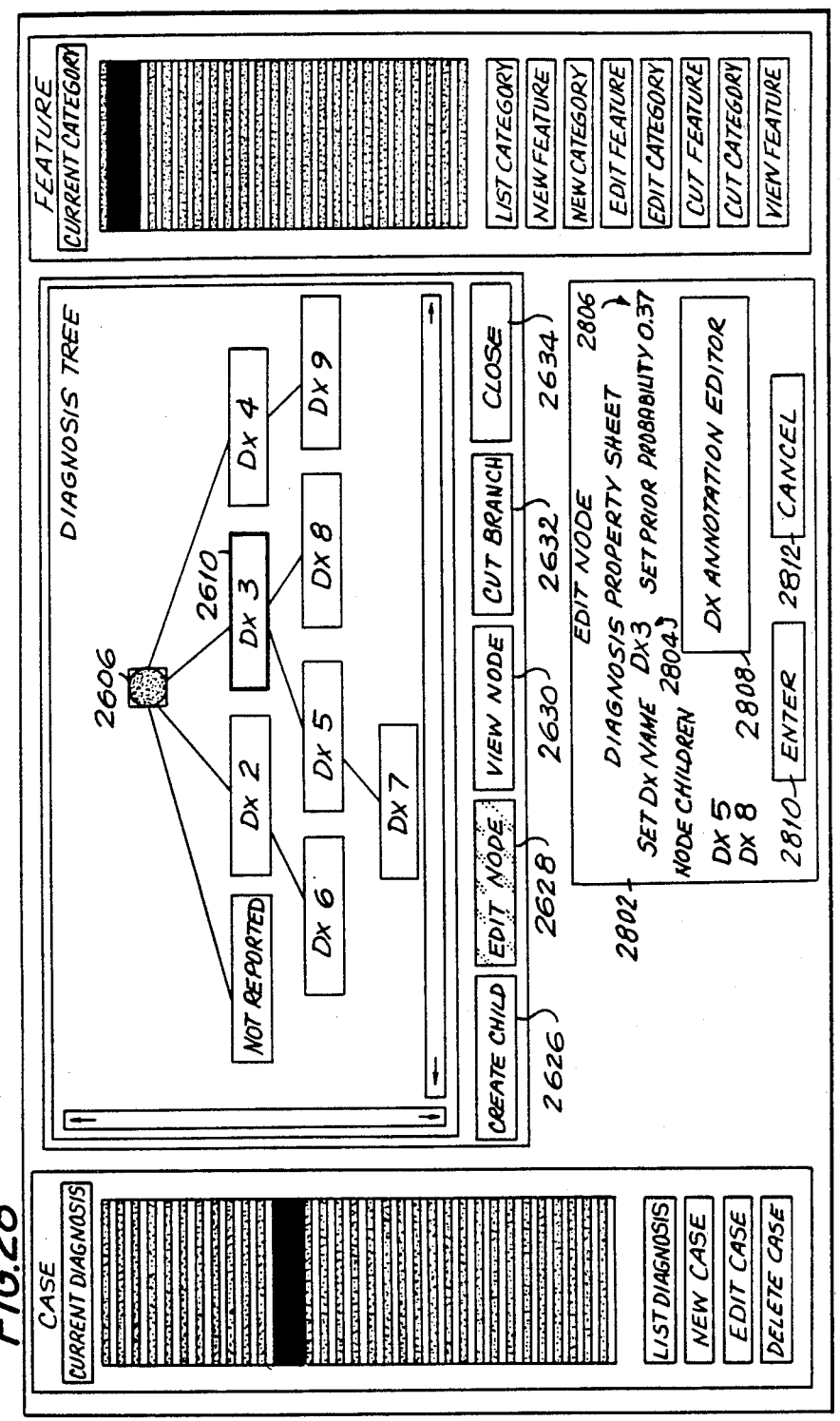
FIG. 28 is a display used in editing a diagnosis node.
Figure 28A:
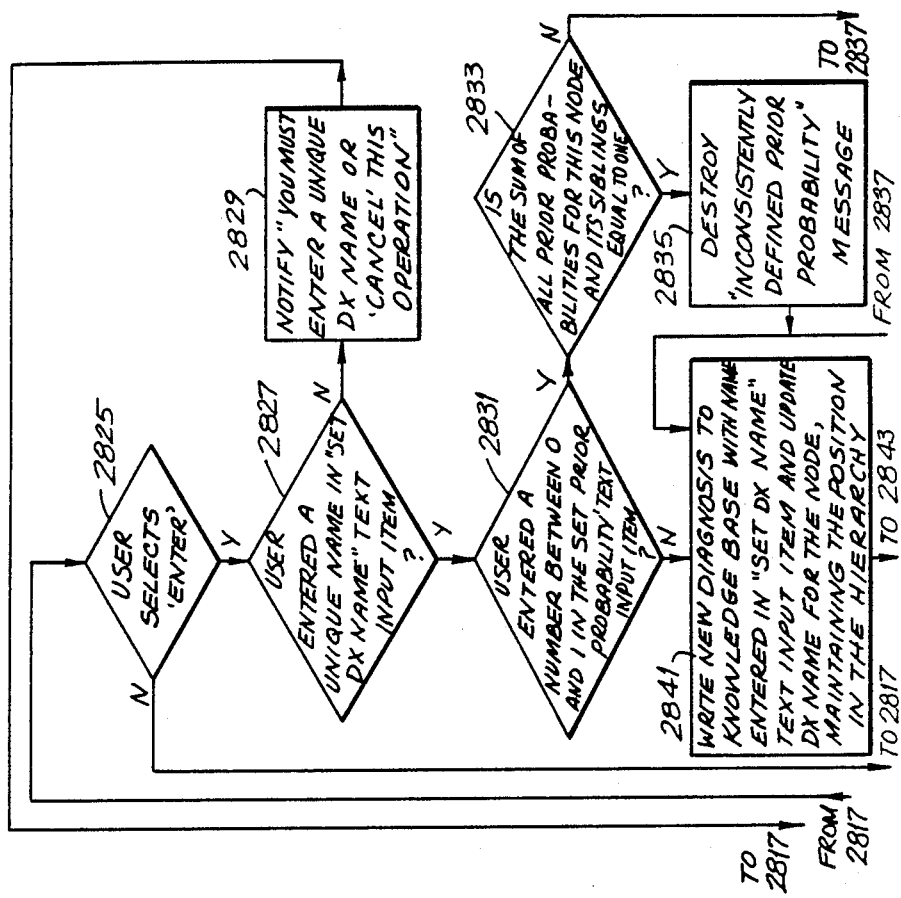
Figure 1:
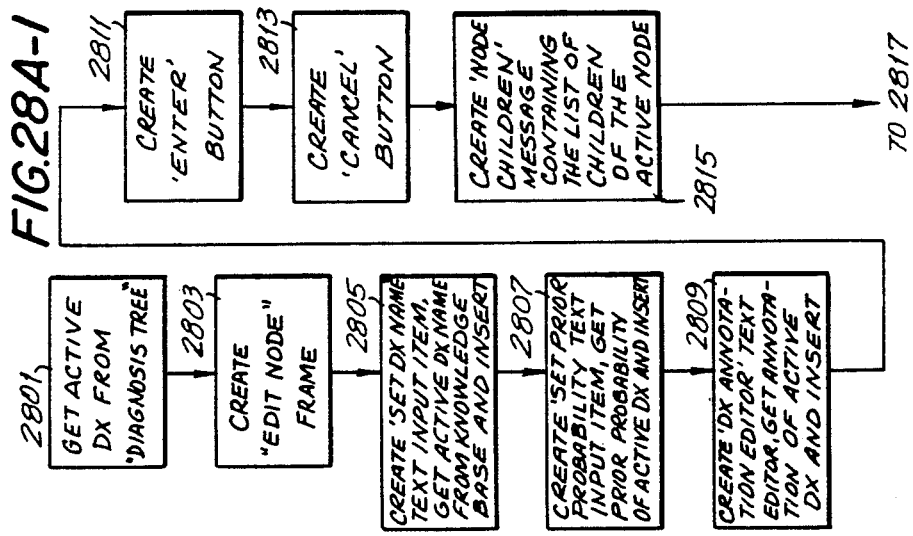
Figures 2, 28A:
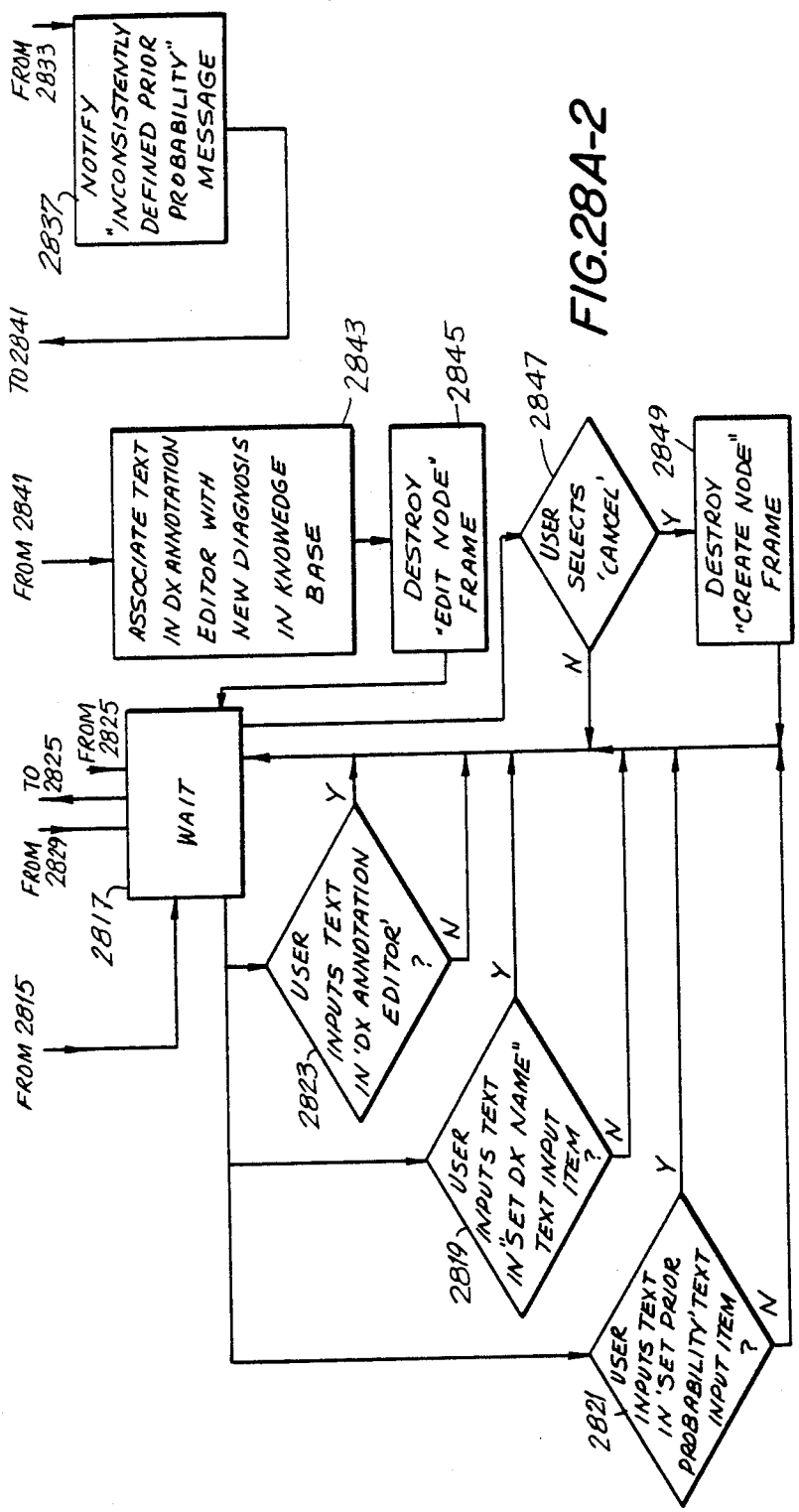
Figure 29:
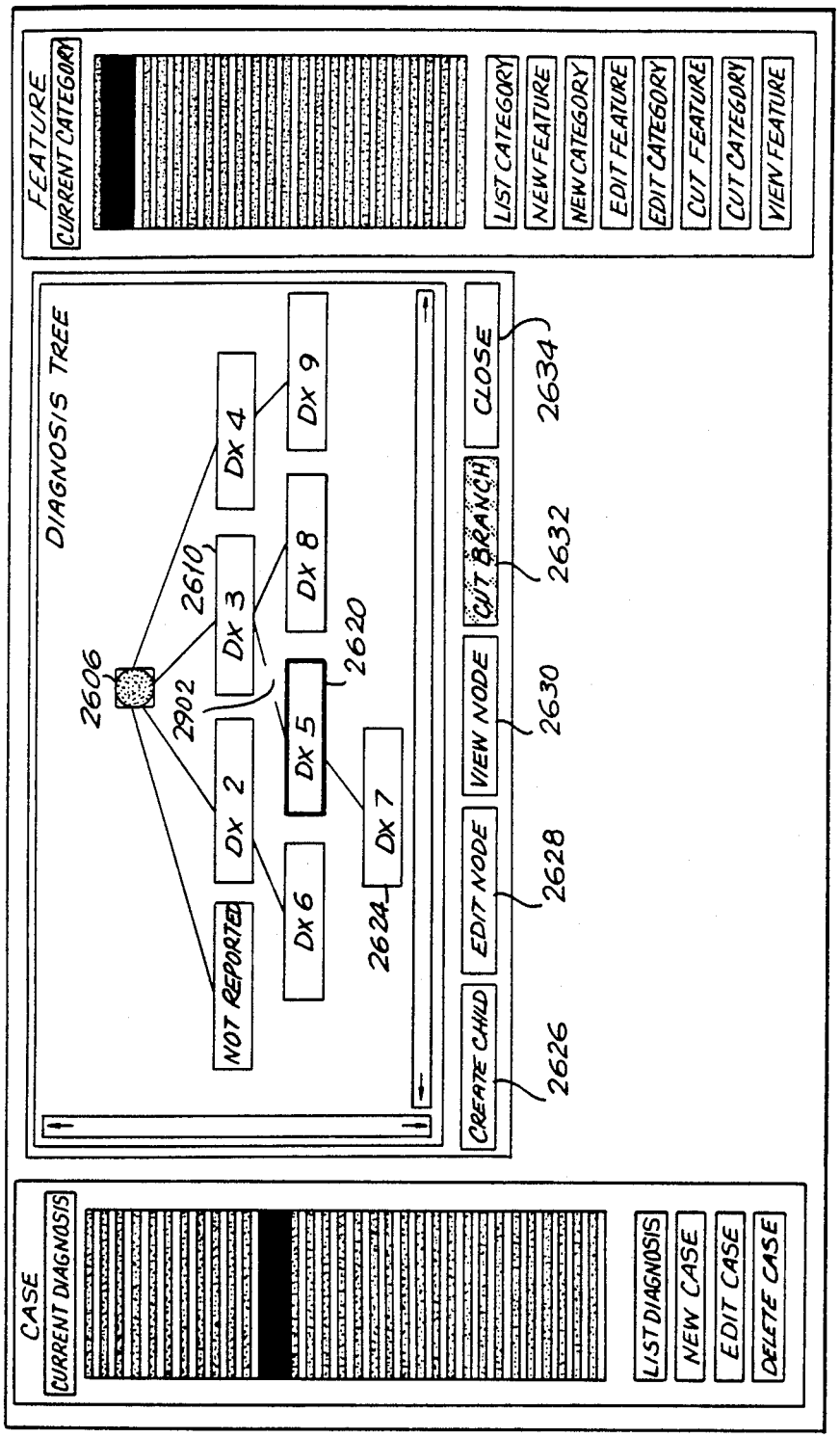
FIG. 29 is a display used in cutting a branch of a diagnosis tree.
Figure 29A:
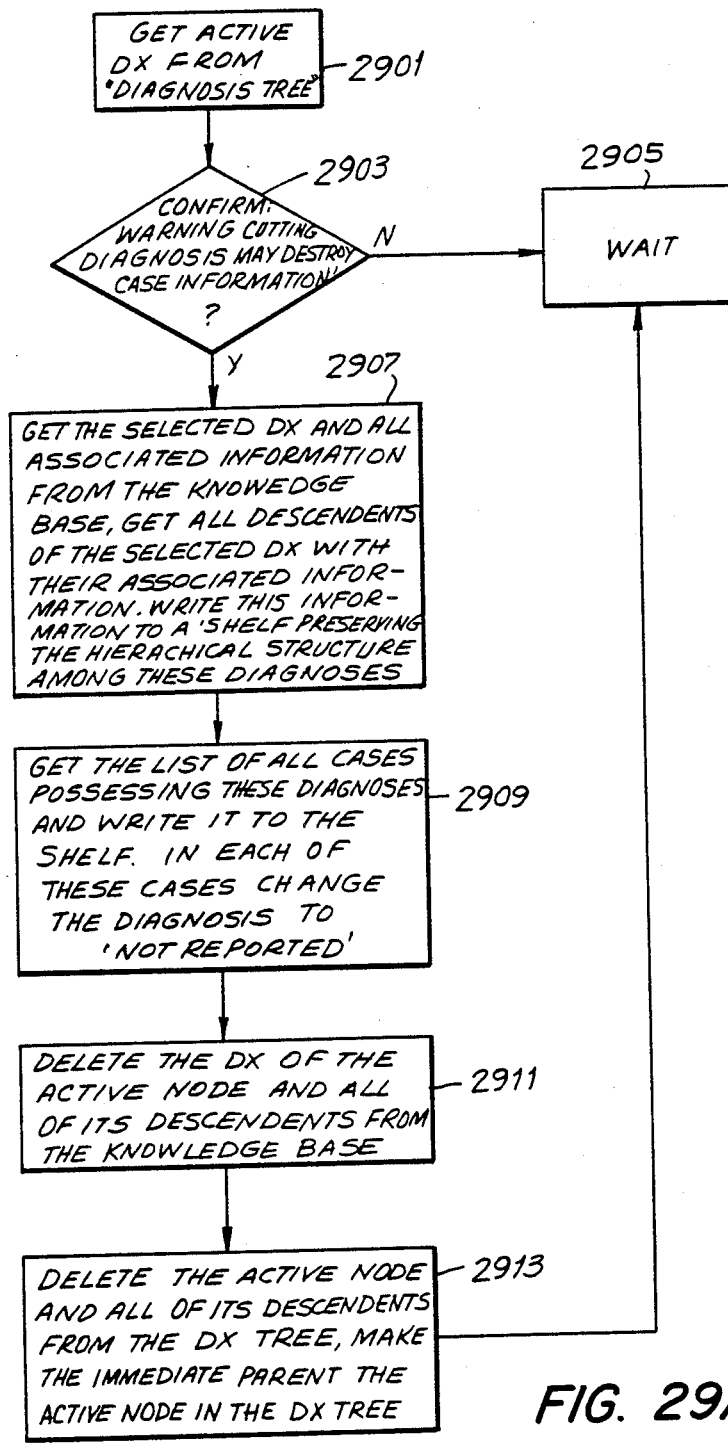
FIG. 29A is a flow chart representing the manner in which the aforementioned branch is cut.
Figure 30:
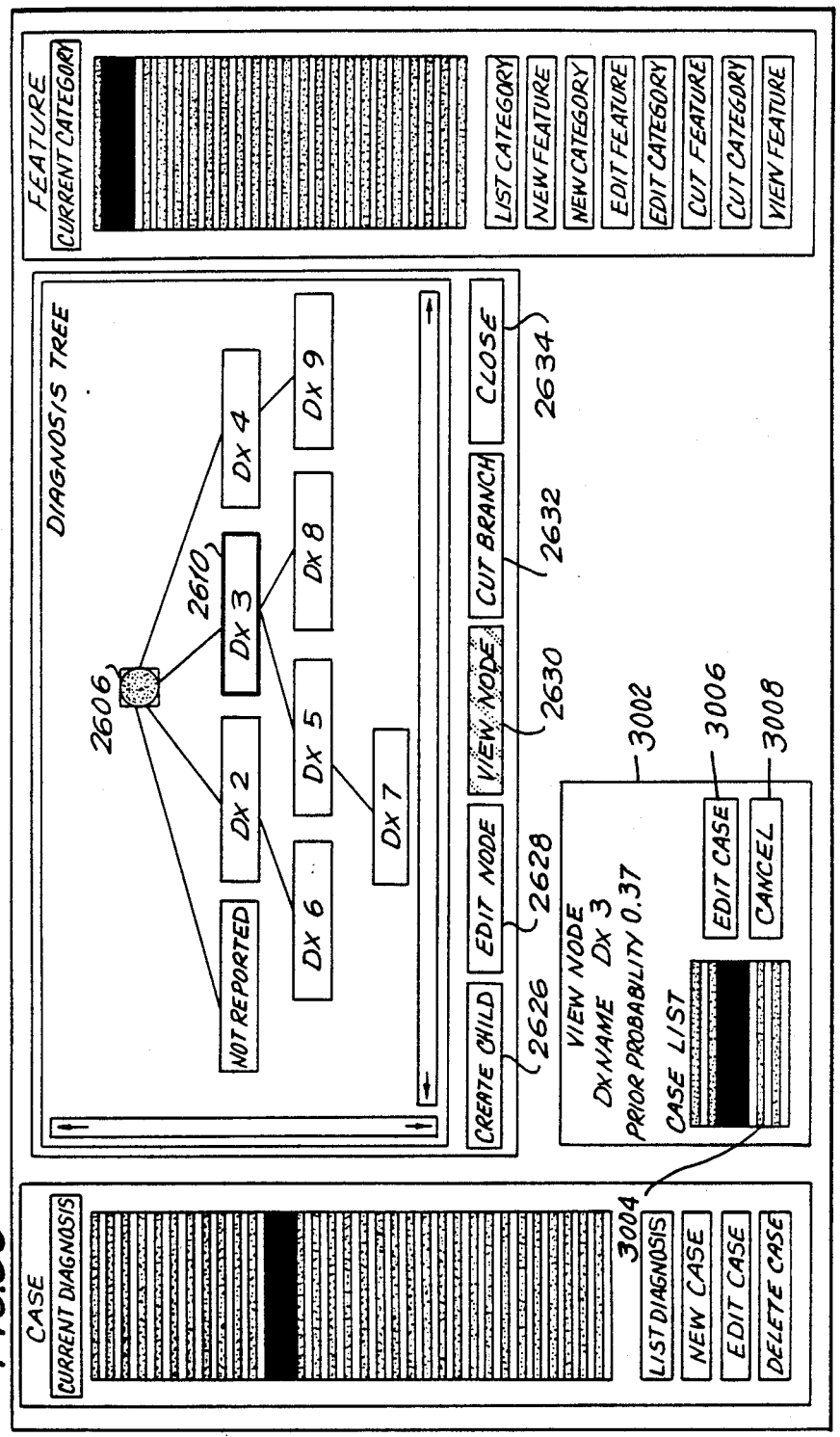
FIG. 30 is a display used in viewing a diagnosis node.
Figure 30A:
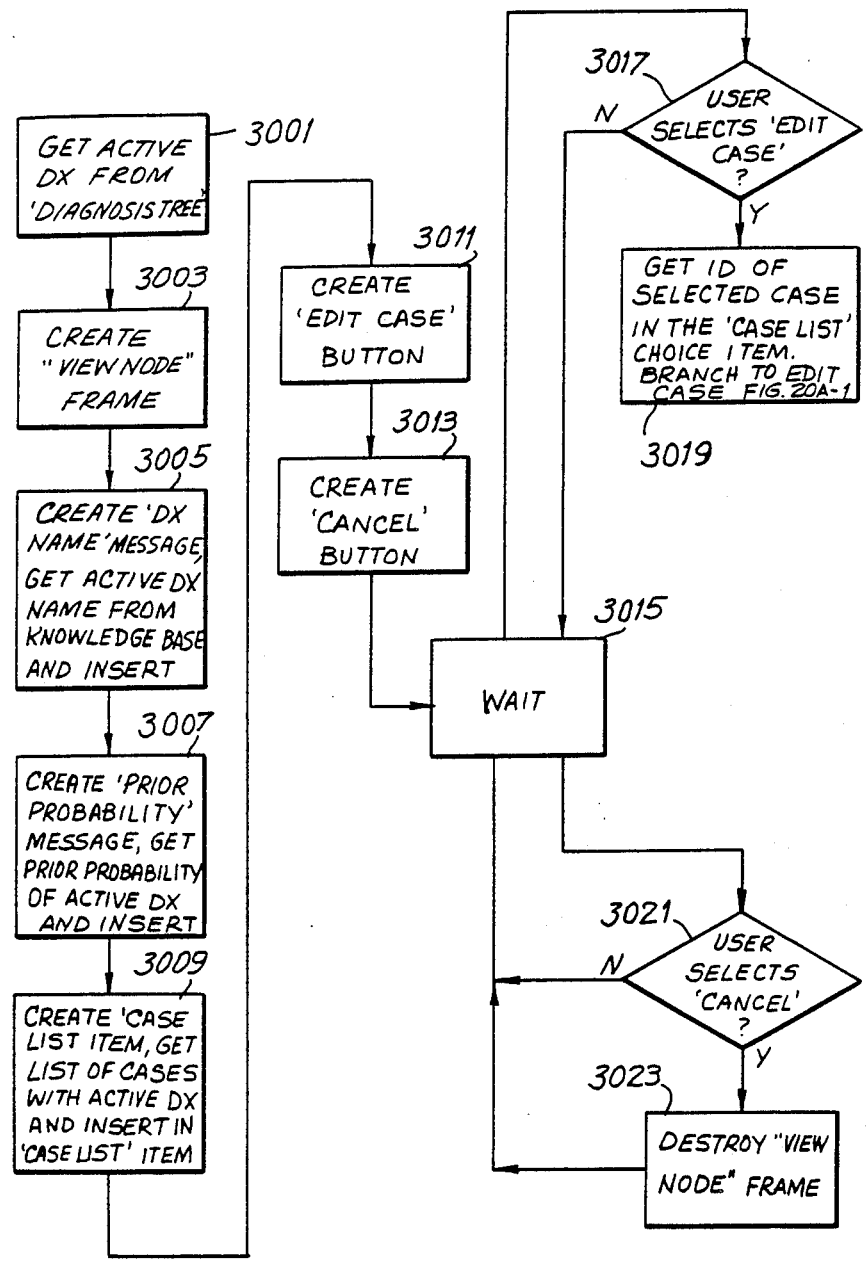
FIG. 30A is a flow chart representing the manner in which the diagnosis node is displayed.

Finally, if delete case button 214 is actuated, as represented by an affirmative answer to inquiry 1735, the processor advances to the function illustrated by the flow chart of FIG. 24A.

While the present invention has been particularly shown and described with reference to a preferred embodiment, it will be appreciated by those of ordinary skill in the art that various changes and modifications may be made without departing from the spirit and scope of the invention. For example, the instant invention is not limited solely for use with a Sun microsystem of the type described herein. It is anticipated that other data processing apparatus, or hardware, either presently commercially available or developed in the future, can be used to carry out the functions which have been described herein. It is further anticipated that the particular programs, or software, used with such hardware might exhibit routines and subroutines that differ in some respects from the routines represented by the flow charts described above. Nevertheless, the overall functions and results disclosed herein will be achieved by such hardware and software.

It also is expected that the means by which data, requests, user commands and the like may be entered into the system may differ in some respects from what has been described above. Although a keyboard and a mouse are preferred, particularly when exploiting the flexibility and ease of operation of the Sun microsystem, other input devices may be used, and some of these have been described above.

Still further, it should be recognized that the computer screens depicted in FIGS. 2-29 represent the presently contemplated best mode and preferred embodiment of the present invention. Nevertheless, other computer screen displays which furnish the user with substantially the same or similar information regarding features and case records may be adopted. It is understood that the presently described computer screens display "buttons" to exploit the flexibility of the Sun microcomputer operating and application systems. If a different data processor is used, or if the operating system is changed, or if displayed buttons no longer are applicable (for example, if a mouse is not used as the input device), the new computer screens will not display such buttons.

In developing the present invention, the separation of the various operating and data knowledge access tools into separate substantially independent sections, as represented by the feature window, the case window and the diagnosis function, has been found advantageous. Functions associated with the creation and editing features in the knowledge base, that is, the dictionary definitions and values of the respective features, affect information contained in all case records. It is helpful, therefore, to separate functions which affect the dictionary, and thus influence the entire knowledge base from functions which affect simply a particular case record. The likelihood of an author inadvertently editing or deleting a particular feature from the knowledge base (i. e. from the dictionary) thus is reduced by separating feature manipulation functions from case manipulation functions. Nonetheless, the present invention should not be construed as requiring this demarcation between the functions; and it is contemplated that, if desired, a menu capable of presenting and executing any and all functions may be presented to the user.

Although the foregoing specification has emphasized the use of the present invention in the discipline of medicine, the invention, in its broader aspects, finds ready application in a wide range of disciplines. More generally, but still not intending to limit the overall applicability thereof, this invention may be used to create a knowledge base of information and data produced by interpreting and characterizing empirical observations using the experience and knowledge of the observer. The information thus accumulated in the knowledge base may be used to reach or confirm deduced conclusions.

**\*\*CLINICAL FEATURES\*\*\***

CF Patient Descriptors

CF Age - numeric 0-20
21-30
31-40
41-50
51-60
61-70
Other

CDX F Sex - valued

Male
Female
Other

CF asbestos Exposure - valued

Present
Absent
Questionable
Unknown
Other

CF Current Sites with Positive Cytology

CDXF Positive Cytology, Right Pleura - valued

Present
Absent
Unknown
Other

CF Positive Cytology, Peritoneum - valued

Present
Absent
Unknown
Other

CF Positive Cytology, Pericardium - valued

Present
Absent
Unknown
Other

CF Prior History of Tumor

CF Previous Tumor Occurence - valued

Present
Absent
Unknown
Other

-continued

CF test - valued
boy
girl
Other
CF Previous Tumor Type - valued
Adenocarcinoma
Squamous Cell Carcinoma
Large Cell Carcinoma
Small Cell Carcinoma
Sarcoma
Lymphoma
Melanoma
Other
CF Previous Tumor Site - valued
Breast
Colon
Esophagus
Kidney
Lung
Ovary
Pancreas
Prostate
Stomach
Uterus
Other
CF Current Medical Problems
CF Congestive Heart Failure - valued
Present
Absent
Questionable
Unknown
Other
CF Myocardial Infarction - valued
Present
Absent
Questionable
Unknown
Other
CF Pulmonary Infarction - valued
Present
Absent
Questionable
Unknown
Other
CF Pulmonary Embolus - valued
Present
Absent
Questionable
Unknown
Other
CF Pneumonia - valued
Present
Absent
Questionable
Unknown
Other
CF Tuberculosis - valued
Present
Absent
Questionable
Unknown
Other
CF liver Disease - valued
Present
Absent
Questionable
Unknown
Other
CF Renal Failure - valued
Present
Absent
Questionable
Unknown
Other
CF Pancreatitis - valued
Present
Absent
Questionable
Unknown -continued Other
CF Collagen Vascular Disease - valued
Present
Absent
Questionable
Unknown
Other
CF Recent Trauma - valued
Present
Absent
Unknown
Other
CF Recent Surgery - valued
Present
Absent
Unknown
Other
CF History of Chemotherapy - valued
Present
Absent
Unknown
Other
CF History of Radiation Therapy - valued
Present
Absent
Unknown
Other
CF Current Symptoms
CF Shortness of Breath - valued
Present
Absent
Unknown
Other
CF Chest or Thoracic Pain - valued
Present
Absent
Unknown
Other
CF Ascities - valued
Present
Absent
Unknown
Other
CF Bowel Obstruction - valued
Present
Absent
Unknown
Other
CH Chest Radigraph
CF Normal CXR - valued
Yes
No
Other
CF Effusion on CXR - valued
Absent
Present - Left
Present - Right
Present - Bilateral
Questionable
Other
CF Infiltrate on CXR - valued
Present
Absent
Questionable
Other
CF Pleural Thickening on CXR - valued
Present
Absent
Questionable
Other
CF Pleural Plaque on CXR - valued
Present
Absent
Questionable
Other
CF Mass on CXR - valued
Present
Absent -continued Questionable
Other
CF Lymphadenopathy on CXR - valued
Present
Absent
Questionable
Other

*PAP Cytology*

PAP Overview
PAP Quality of Fluid - valued
Well Preserved Fluid
Moderately Preserved Fluid
Poorly Preserved Fluid
Clotted Fluid
Other
PAP Staining Reaction - valued
Adequate
Inadequate
Other
PAP Cellularity of Specimen - valued
Low Cellularity
Moderate Cellularity
High Cellularity
Other
PAP# Atypical/Suspicious Cells/Groups - valued
Absent
Few
Moderate
Many
Other
PAP Cytoplasmic Morphology
PAP Cytoplasm, Abnormal Population - valued
Pale
Delicate
Dense
Variable
Poorly Visualized
NA
Other
PAP Cytoplasm, Mesothelial Population - valued
Pale
Delicate
Dense
Variable
Poorly Visualized
NA
Other
PAP Halo Outside Cell Border - valued
Absent
Occasional
Frequent
Other
PAP Halo Inside Cell Border - valued
Absent
Occasional
Frequent
Other
PAP Cytoplasmic Pigment - valued
Absent
Yellow
Brown
Black
Green
Other
PAP Cytoplasmic Vacuoles - valued
Absent
Occasional
Frequent
Other
PAP Number of Cytoplasmic Vacuoles - valued
Primarily Single
Primarily Multiple
NA
Other
PAP Cytoplasmic Vacuolar Size - valued
Small
Large
Variable -continued NA
Other
PAP Mucin Containing Vacuoles - valued
Present
Absent
Unknown
Other
PAP Nuclear Deformation by Vacuoles - p/a
Present
Absent
Other
PAP Phagocytosis - p/a
Present
Absent
Other
PAP Nuclear Morphology
PAP Multinucleation - valued
Absent
Primarily Binucleate
Primarily > 2 Nuclei/Cell
Other
PAP Chromatin, Abnormal Population - valued
Clear
Pale
Even
Finely Granular
Coarsely Granular
Hyperchromatic
Irregular
Variable
NA
Other
aaron - p/a
Present
Absent
Other
PAP Chromatin, Mesothelial Population - valued
Clear
Pale
Even
Finely Granular
Coarsely Granular
Hyperchromatic
Irregular
Variable
NA
Other
PAP Nuclear Border Shape - valued
Smooth
Irregular
Variable
Other
PAP Nucleoli - valued
Absent
Occasional
Frequent
Other
PAP Nucleoli per Nucleus - valued
Primarily Single
Primarily Multiple
NA
Other
PAP Nucleolus Size - valued
Small
Large
Varable
Other
PAP Nucleolus Shape - valued
Round
Irregular
Variable
Other
PAP Mitoses - p/a
Present
Absent
Other
PAP Features of Cell Background
PAP Macrophages - valued Absent
Few
Moderate
Many
Other
PAP Lymphocytes - valued
Absent
Few
Moderate
Many
Other
PAP Polymorphonuclear Leucocytes - valued
Absent
Few
Moderate
Many
Other
PAP Reactive Mesothelial Cells - valued
Absent
Few
Moderate
Many
Other
PAP Activated Lymphocytes - valued
Absent
Few
Moderate
Many
Other

*Cell Block Features*

CB Overview
CB Quality of FLuild - valued
Well Preserved Fluid
Moderately Preserved Fluid
Poorly Preserved Fluid
Clotted Fluid
Other
CB Staining Reaction - valued
Adequate
Inadequate
Other
CB Cellularity of Specimen - valued
Low Cellularity
Moderate Cellularity
High Cellularity
Other
CB π Atypical/Suspicious Cells/Groups - valued
Absent
Few
Moderate
Many
Other
CB General Cell Morphology
CB Cell Shape, Abnormal Population - valued
Round
Oval
Cuboidal
Columnar
Polygonal
Spindle
Irregular
NA
Other
CB Cell Shape, Mesothelial Population - valued
Round
Oval
Cuboidal
Columnar
Polygonal
Spindle
Irregular
NA
Other
CB Nuclear Shape, Abnormal Population - valued
Round
Oval
Spindle
Irregular
Variable
NA
Other
CB Nuclear Shape, Mesotherlial Population - valued
Round
Oval
Spindle
Irregular
Variable
NA
Other
CB Pleomorphism of Size, Single Cells - valued
Minimal
Moderate
Marked
Other
CB Pleomorphism of Shape, Single Cells - valued
Minimal
Moderate
Marked
Other
CB Pleomorphism, N:C Ratio, Single Cells - valued
Minimal
Moderate
Marked
Other
CB Pleomorphism of Nuclei, Single Cells - valued
Minimal
Moderate
Marked
Other
CB Features of Cell Groups
CB Cell Groupings Present - p/a
Present
Absent
Other
CB Shape of Cell Groups - valued
Papillary
Acinar
Flat
Variable
Other
CB Cell Number in Largest Groups - numeric
2
3-4
5-10
11-20
>21
Other
CB Cell Number in Average Groups - numeric
2
3-4
5-10
11-20
>21
Other
CB Pleomorphism of Cell Size in Groups - valued
Minimal
Moderate
Marked
Other
CB Pleomorphism of Cell Shape in Groups - valued
Minimal
Moderate
Marked
Other
CB Cell Orientation in Groups - valued
Regular
Partially Disoriented
Disoriented
Other
CB Similarity to Mesothelial Cells - valued
Present
Partial
Absent
Other
CB Distinct Outer Border of Cell Groups - p/a
Present
Absent -continued Other
CB Psamomma Bodies - p/a
Present
Absent
Other
CB Connective Tissue Cores - p/a
Present
Absent
Other
CB Histochemical Stains
CB Mucicarmine - valued
Positive
Negative
Not Done
Other
CB PAS - valued
Positive
Negative
Not Done
Other
CB PAS After Diastase - valued
Reduced Positive
Residual Positive
Not Done
Other
CB Trichrome - valued
Positive
Negative
Not Done
Other
CB Colloidal Iron, Cells - valued
Positive
Negative
Not Done
Other
CB Collodal Iron, Background - valued
Positive
Negative
Not Done
Other
CB Colloidal Iron After Hyal, Cells - valued
Reduced Positive
Residual Positive
Not Done
Other
CB Colloidal Iron After Hyal, Background - valued
Reduced Positive
Residual Positive
Not Done
Other
CB Colloidal Iron After Hyal, Background - valued
Reduced Positive
Residual Positive
Not Done
Other
CB Immunoperoxidase
CB Keratin, Strength of Reaction - valued
Negative
+
++
+++
Not Done
Other
CB Keratin, % of Cells Reacting - numeric
0
1-5
6-10
11-25
26-50
51-75
76-95
96-100
Not Done
Other
CB CEA Strength of Reaction - valued
Negative
+
++

-continued

+++
Not Done
Other
CB CEA, % of Cells Reacting - numeric
0
1-5
6-10
11-25
26-50
51-75
76-95
96-100
Not Done
Other
CB GICA, Strength of Reaction - valued
Negative
+
++
+++
Not Done
Other
CB GICA, % of Cells Reacting - numeric
0
1-5
6-10
11-25
26-50
51-75
76-95
96-100
Not Done
Other
CB SSEA Strength of Reaction - valued
Negative
+
++
+++
Not Done
Other
CB SSEA, % of Cells Reacting - numeric
0
1-5
6-10
11-25
26-50
51-75
76-95
96-100
Not Done
Other
CB EMA Strength of Reaction - valued
Negative
+
++
+++
Not Done
Other
CB EMA, % of Cells Reacting - numeric
0
1-5
6-10
11-25
26-50
51-75
76-95
96-100
Not Done
Other

*Microscopic Preparation*

MP Magnification
MP 10 × Objective - valued
330 × to screen
Other
MP 45 × Objective - valued
880 × to screen
Other
MP 45 × Objective - valued
1475 × to screen
Other -continued MP 100 × Oil Immersion - valued
2800 × to screen
Other
MP Tissue Preparation
MP Staining - valued
Hemotoxalin and Eosin
Papanicalou
Mucicarmine
PAS
PAS After Diastase
Trichrome
Colloidal Iron
Collidal Iron After Hyaluronidase
Keratin
CEA
GICA
SSEA
EMA
Other
MP Hemotoxalin and Eosin - Type Not Reported
MP Papanicalou - Type Not Reported
MP Muncicarmine - Type Not Reported
MP PAS - Type Not Reported
MP PAS after Diastase - Type Not reported
MP Trichrome - Type Not Reported
MP Colloidal Iron - Type Not Reported
MP Colloidal Iron after Hyaluronidase - Type Not Reported
MP Keratin - Type Not Reported
MP CEA - Type Not Reported
MP GICA - Type Not Reported
MP SSEA - Type Not Reported
MP EMA - Type Not Reported The present invention and knowledge base created thereby also may be used as a reference work. For example, in the medical discipline, the present invention and knowledge base may assist the training of physicians. Similarly, physicians, such as pathologists, who operate outside of their area of particular expertise may find the reference presented by the present invention a valuable support. Of course, the use of this invention as an aid in medical diagnosis is a primary objective.

It is intended that the appended claims be interpreted as including the foregoing as well as other equivalents.

What is claimed is:

1. A system for creating a knowledge base of cases of diseases, each case being comprised of features observed with a disease and at least some of said cases containing one or more visual images of said features, said knowledge base being useful as a computerized aid to the cognitive process of diagnosis, said system comprising:

case identifying means for identifying a case record written into and retrievable from said system;

feature selecting means operable by a user to select from a feature bank those feature data which the user observes in one or more diseases represented by a case;

value selecting means operable by said user to select from a value bank data which the user observes in the selected feature;

edit means operable by said user to create or delete feature data in said feature bank and value data in said value bank associated with a respective feature;

display means for displaying pictorial images of one or more features associated with a disease;

storage means for storing case records, each case record including a case record identification, feature data selected for that case, value data selected for each feature, and pictorial image data representing pictorial images associated with that case; and processing means for linking feature data, value data and pictorial image data to case records, for retrieving from said storage means those case records having particular features identified by a user, for modifying feature or value data included in a retrieved case record, and for causing said display means to display pictorial images associated with said retrieved case record.

2. The system of claim 1 further comprising image generating means for generating a pictorial image of one or more features observed in a case and for producing pictorial image data representative thereof for display and for storage.

3. The system of claim 2, wherein said processing means includes overlay means for generating an overlay selected by said user for display over a displayed pictorial image; and means for storing and retrieving data representing said overlay and the position thereof relative to said displayed pictorial image.

4. The system of claim 3, wherein said display means includes means responsive to retrieval of stored overlay data by said processing means for displaying a stored pictorial image with said overlay.

5. The system of claim 3 wherein said overlay means is operative in response to manual selection by said user to indicate a selected feature.

6. The system of claim 2 wherein said feature bank includes visual feature data representing those features having visual characteristics that are observable in a pictorial image.

7. The system of claim 6 wherein said processing means includes search means responsive to the selection by said feature selecting means of feature data for searching and retrieving said case records for all cases having said selected feature data.

8. The system of claim 7 wherein said processing means includes means for supplying to said display means pictorial image data included in a case record having a selected visual feature data for displaying a pictorial image of said visual feature data.

9. The system of claim 7 wherein said display means is responsive to said search means for displaying the respective case record identifications of those case records having said selected feature data.

10. The system of claim 9 wherein said processing means further includes scroll means responsive to operation by said user for scrolling through said respective case record identifications and for causing said display means to display the scrolled case record identifications.

11. The system of claim 10 wherein said processing means further includes selecting means responsive to operation by said user for selecting a case record whose case record identification is displayed and supplying at least a portion of said case record to said display means for displaying to said user a pictorial image of the selected visual feature data included in said selected case record.

12. The stem of claim 11 wherein said processing means further includes means for causing said display means to display the number of cases stored in said storage means having said selected feature data and means for determining the distribution relative to each other of value data associated with said cases.

13. The system of claim 12 wherein said search means is further responsive to operation of said feature selecting means for selecting additional feature data and for retrieving those case records having all of the feature data selected by said user.

14. The system of claim 7 wherein said pictorial image data represent plural pictorial images, and wherein said display means displays all of the pictorial images included in a retrieved case record.

15. The system of claim 14 wherein said display means displays all of the pictorial images in relatively reduced size and said processing means includes image selecting means responsive to operation by said user for selecting one of the displayed pictorial images to be displayed in relatively magnified size.

16. The system of claim 1 wherein the value data are representative of discrete values or continuous values for a respective feature; and wherein said edit means includes:
   (a) means for selecting discrete or continuous values,
   (b)
      (i) means responsive to the selection of a discrete value to cause said display means to display preset value data already provided in said value bank which may be assigned by said user to said respective feature, and
      (ii) means responsive to manual operation by said user to enter into said value bank new discrete value data; and
   (c) means responsive to the selection of a continuous value to cause said display means to display prompts for the user to select a range for the continuous value which may be assigned by said user to said respective feature.

17. The system of claim 1 wherein the value data are representative of measured values; and wherein said processing means includes means for determining the measured value for selected features.

18. The system of claim 17 wherein said processing means includes manually operable curve tracing means for tracing an area of a feature displayed on said display means; and said means for determining the measured value operates to determine the area traced by said curve tracing means.

19. The system of claim 17 wherein said processing means includes manually operable distance measuring means for measuring the distance between points located in the pictorial image displayed by said display means.

20. The system of claim 17 wherein said processing means includes manually operable means for identifying points located in the pictorial image displayed by said display means; and said means for determining the measured value operates to calculate the density of the identified points.

21. The system of claim 1 wherein said storage means includes optical storage means for storing said pictorial image data.

22. The system of claim 21 wherein said optical storage means comprises on optically readable disk; and said storage means further includes magnetic storage means for storing said case record identification, feature data and value data.

23. The system of claim 22 wherein said processing means includes overlay means for generating an overlay selected by said user for display over a displayed pictorial image; and said magnetic storage means stores data representing said overlay and the position thereof relative to said displayed pictorial image.

24. An authoring system for providing a knowledge base for use as a computerized aid to the cognitive process of diagnosis, comprising:
   manually operative input means for use by an author to generate data, to request data, and to request predetermined processing operations on said data;
   image data input means for generating image data derived from and representing preselected visual images useful in the cognitive process of diagnosis;
   display means for displaying both alphanumeric information and visual images of image data;
   accessible storage means for storing data generated by said manually operative input means and by said image data input means; and
   programmable processing means in data communication with said manually operative input means, image data input means, display means and storage means and programmed to establish in response to said manually operative input means user-selectable diagnostic features which the user determines are characteristic of respective conditions to be diagnosed and to establish user-selectable values of said feature, said processing means also being programmed to store in said storage means image data representing visual images of at least some of said features, said processing means being further programmed to cause said display means to display prompts for guiding said user to select respective ones of the established features and to assign an established value to a selected feature which the user observes in a visual image, and said processing means being additionally programmed to link a selected feature having an assigned value with a visual image for storage in and retrieval from said storage means.

25. The system of claim 24 wherein each feature is associated with plural predetermined values, and wherein said processing means causes said display means to display said associated values when said manually operative input means is operated by an author to select a feature so that one of said values may be selected by said author, and said processing means assigns the selected value to the selected feature.

26. The system of claim 25 wherein said manually operative input means is operated by an author to select an established feature or to create a new feature for storage in said storage means, and is further operated by an author to select an established value or to create a new value for storage in said storage means.

27. The system of claim 26 wherein said processing means is further programmed to establish user-selectable categories of features in response to said manually operative input means, each category being comprised of a unique set of features, said processing means also being programmed to link a category to the set of features therein for storage in and retrieval from said storage means, and said processing means causes said display means to display a category when said manually operative input means is operated by an author to retrieve that category from said storage means and permit the author to select the displayed category and thereby retrieve and observe the features included therein.

28. The system of claim 26 wherein said processing means is programmed to establish a user-selectable value for a feature in response to said manually operative input means and to cause said display means to prompt the user to identify the feature as a particular type and to assign a value dependent upon the identified type.

29. The system of claim 28 wherein said processing means causes said display means to display only predetermined type identifications for selection by the author.

30. The system of claim 29 wherein said predetermined type identifications include "discrete" and "continuous" types; and wherein said processing means is further programmed to retrieve and display a set of values associated with said feature, if said feature is identified as a "discrete" type, and to assign a selected one of those displayed values to said feature as determined by the author, and said processing means is programmed to retrieve and display upper and lower value range limits associated with said feature, if said feature is identified as a "continuous" type, and to assign a selected segment in said range to said feature as determined by the author.

31. The system of claim 26 wherein said processing means is programmed to cause said display means to prompt the user to identify a feature as a type having a variable value and to measure a value for that feature if said author operates said manually operative input means to so identify that feature, the measurement being dependent upon physical parameters selected by said author.

32. The system of claim 31 wherein said physical parameters include length, and said processing means is programmed to measure length between points displayed in a visual image and selected by the operation by said author of said manually operative input means.

33. The system of claim 31 wherein said physcial parameters include area, and said processing means is programmed to measure area of a closed curve displayed in a visual image and selected by the operation by said author of said manually operative input means.

34. The system of claim 31 wherein said physcial parameters include density, and said processing means is programmed to measure density in response to the operation by said author of said manually operative input means to define an area on a pictorial display displayed by said display means for which density is to be calculated.

35. The system of claim 26 wherein said processing means is programmed to create a case record in response to the operation by said author of said manually operative input means, said case record being formed of plural user-selected features, each having a user-selected value, and at least one of said case records having a visual image linked to a feature therein.

36. The system of claim 35 wherein a particular feature is included in plural case records, and wherein said processing means is programmed to delete that feature from all of said case records in response to operation by said author of said manually operative input means to delete said feature from said storage means.

37. The system of claim 35 wherein said processing means is further programmed to establish in response to said manually operative input means user-selected categories of features for each case record, each category being comprised of a unique set of features and a particular category in a case record including at least some of the features in that set, said processing means being additionally programmed to delete a category of features selected by said manually operative input means from all of the case records.

38. The system of claim 55 wherein said processing means is further programmed to store case records in said storage means and to retrieve therefrom a case record selected by said manually operative input means for causing said display means to display at least selected data included in the retrieved case record.

39. The system of claim 38 wherein the selected data included in the retrieved case record that is displayed by said display means includes image data, whereby a visual image is displayed.

40. The system of claim 39 wherein said processing means is further programmed to cause said display means to display a set of overlay images and is responsive to the operation by said author of said manually operative input means to link an overlay image with a feature present in the displayed visual image and to store as part of said case record overlay data representing the location in the visual image of the overlay image linked with the feature present in said visual image.

41. The system of claim 40 wherein the selected data included in the retrieved case record that is displayed by said display means further includes overlay data, whereby an overlay image superimposed on said visual image is displayed.

42. The system of claim 24 wherein said manually operative input means comprises a keyboard.

43. The system of claim 24 wherein said manually operative input means comprises a physically movable cursor positioning means for causing a cursor displayed on said display means to be located at a position corresponding to the movement of said cursor positioning means.

44. The system of claim 43 wherein said cursor positioning means includes at least one selector switch; wherein said display means displays information linked to features, values and image data stored in said storage means; and wherein said processing means is programmed to respond to the operation of said selector switch when the cursor displayed on said display means is located at a position whereat information linked to a stored feature, value or image data is displayed to retrieve and display that linked feature, value of visual image.

45. The system of claim 24 wherein said image data input means comprises a video camera for producing video signals representing images picked up by the video camera; and digitizing means for digitizing the video signals to produce said image data.

46. The system of claim 45 wherein said image data input means further comprises a microscope optically coupled to said video camera for presenting images to the video camera.

47. The system of claim 46 wherein said processing means is in data communication with said digitizing means and is further programmed to cause said display means to display simultaneously a visual image derived from image data retrieved from said storage means and an image derived from image data produced by said digitizing means.

48. A method for creating a knowledge base of cases of diseases, each case being comprised of features observed with a disease and at least some of said cases containing one or more visual images of said features, said knowledge base being useful as a computerized aid to the cognitive process of diagnosis, said method comprising the steps of:

providing a knowledge base of features observed in examples of diseases;

selecting from the knowledge base those features which the user observes in one or more diseases represented by a case;

selecting from the knowledge base a value which the user observes in the selected feature;

editing the knowledge base by selectively adding thereto or deleting therefrom features and values associated with respective features;

generating pictorial image data representing pictorial images of one or more features associated with a disease;

displaying at least one of said pictorial images;

storing in a case record the features selected for the case, the value selected for each feature, and the pictorial image data generated for that case;

retrieving those case records having particular features identified by a user; and selectively modifying features or values included in a retrieved case record.

49. The method of claim 48, further comprising the steps of generating an overlay selected by the user for display over a displayed pictorial image; and storing data representing said overlay and the position thereof relative to said displayed pictorial image.

50. The method of claim 49, further comprising the step of retrieving said stored overlay data from storage and retrieving stored pictorial image data for display with said overlay.

51. The method of claim 49 wherein said overlay indicates a selected visual feature.

52. The method of claim 48 further comprising the step of retrieving stored pictorial image data included in a case record having a selected feature to display a pictorial image of that feature.

53. The method of claim 48 further comprising the steps of displaying identifications of the retrieved case records; selecting one of the case records whose identifications are displayed; and displaying to the user a pictorial image of the particular features included in that selected case record.

54. The method of claim 53 further comprising the steps of determining the quantity of stored cases having a particular feature; and determining the distribution relative to each other of such cases having different respective values for that feature.

55. The method of claim 48 wherein said pictorial image data represent plural pictorial images, and wherein the step of displaying comprises displaying all of the pictorial images included in a retrieved case record.

56. The method of claim 55 wherein the step of displaying includes displaying all of the pictorial images in relatively reduced size and selecting one of the displayed pictorial images for display in relatively magnified size.

57. The method of claim 48 wherein the values in the knowledge base are discrete or continuous values for a respective feature; and wherein the step of editing includes selecting a discrete value, displaying preset values already provided in the knowledge base which may be assigned by the user to the said respective feature, or selecting and entering into said knowledge base new discrete values selected by the user; or selecting a continuous value and displaying prompts for the user to select a range for the continuous value which may be assigned by said user to the said respective feature.

58. The method of claim 48 wherein the values in the knowledge base are measured values.

59. The method of claim 58 wherein the step of selecting a value includes the steps of tracing an area of a displayed pictorial image of a feature and measuring the traced area.

60. The method of claim 58 wherein the step of selecting a value includes the step of measuring the distance between points located in the displayed pictorial image.

61. The method of claim 58 wherein the step of selecting a value includes the steps of identifying points in an area of the displayed pictorial image, and measuring the density of the identified points.

62. A method of creating a knowledge base for use as a computerized aid to the cognitive process of diagnosis, comprising the steps of:

inputting into the knowledge base image data derived from and representing preselected visual images useful in the cognitive process of diagnosis;

providing in the knowledge base predetermined textual feature designations of diagnostic features which are characteristic of respective conditions that are expected to be present in a diagnosis;

providing in the knowledge base predetermined feature values for each provided diagnostic feature;

selectively displaying both alphanumeric feature designations and feature values provided in the knowledge base and visual images of the image data in the knowledge base;

displaying prompts to a user for guiding said user to select a predetermined feature designation already provided in the knowledge base and which the user observes in a displayed visual image, and displaying further prompts to said user for guiding said user to select a predetermined feature value already provided in the knowledge base and assigning that feature value to the selected feature designation;

inputting into the knowledge base said user-selected feature designation which the user determines is characteristic of a condition to be diagnosed;

inputting into the knowledge base said user-slected feature value assigned to said user-selected feature designation; and linking said selected feature having said assigned value with said displayed visual image for subsequent retrieval from the knowledge base and display.

63. The method of claim 62 wherein each predetermined feature designation is associated with plural predetermined feature values; and further comprising the steps of displaying said associated feature values when a feature designation is selected from the knowledge base so that one of said feature values may be assigned to that feature designation.

64. The method of claim 63 wherein the steps of inputting feature designations and feature values into the knowledge base comprise selecting an established feature designation already in the knowledge base or creating a new feature designation for storage in the knowledge base, and selecting an established feature value already in the knowledge base or creating a new feature value for storage in the knowledge base.

65. The method of claim 64 further comprising the steps of inputting into the knowledge base user-selectable categories of features, each category being comprised of a unique set of feature designations; linking a category in the knowledge base to the set of feature designations therein; and displaying a category to permit the selection of the displayed category and thereby retrieve and observe the feature designations included therein.

66. The method of claim 64 wherein the step of selecting a feature value comprises the steps of displaying prompts to a user to prompt the user to identify the feature designation as a particular type, and assigning a value dependent upon the identified type.

67. The method of claim 66 wherein particular feature type identifications include "discrete" and "continuous" types; and wherein the step of assigning a value comprises the steps of retrieving and displaying a set of feature values associated with said feature designation if said feature designation is identified as a "discrete" type, and assigning a selected one of those displayed values to said feature designation; and retrieving and displaying upper and lower value range limits associated with said feature designation if said feature designation is identified as a "continuous" type, and assigning a selected segment in said range to said feature designation.

68. The method of claim 64 wherein the step of selecting a feature value comprises the steps of displaying prompts to a user to prompt the user to identify a feature value designation as a type having a variable feature value, and measuring a value for that feature designation dependent upon selected physical parameters therein.

69. The method of claim 68 wherein said physical parameters include length, and said step of measuring comprises measuring the length between selected points displayed in a visual image.

70. The method of claim 68 wherein said physical parameters include area, and said step of measuring comprises measuring the area of a selected closed curve displayed in a visual image.

71. The method of claim 68 wherein said physical parameters include density, and said step of measuring comprises measuring density of a selected area on a pictorial display.

72. The method of claim 64 further comprising the step of creating a case record formed of plural user-selected feature designations, each having a user-selected feature value, and at least one of said case records having a visual image linked to a feature designation therein.

73. The method of claim 72 wherein a particular feature designation is included in plural case records, and further comprising the step of deleting that feature designation from all of said case records so as to delete said feature designation from said knowledge base.

74. The method of claim 72 further comprising the steps of establishing user-selected categories of feature designations for each case record, each category being comprised of a unique set of feature designations and a particular category in a case record including at least some of the feature designations in that set; and deleting a selected category of feature designations from all of the case records.

75. The method of claim 72 further comprising the steps of displaying a set of overlay images, linking an overlay image with a feature designation present in the displayed visual image; and storing as part of said case record overlay data representing the location in the visual image of the overlay image linked with the feature designation present in said visual image, such that when the case record is retrieved, an overlay image on said visual image is displayed.

76. A computerized aid to the cognitive process of diagnosis comprising:
textual knowledge base means for storing text data including: (a) case information representing multiple case records each of which includes data indicative of features that characterize the case, and (b) feature information representing multiple feature records each of which is comprised of data indicative of the components of which the features that characterize a case are formed;
image knowledge base means for storing image data representing images of features which are included in the case records stored in the textual knowledge base means;
inquiry entry means for use by an operator to enter text inquiry data designating case or feature records for selectively retrieving case information text data or feature information text data from said textual knowledge base means, and for retrieving image data from said image knowledge base means;
processor means responsive to said text inquiry data to retrieve case or feature information text data from said textual knowledge base means and to retrieve image data from said image knowledge base means in response to text inquiry data designating feature records; and
picture display means responsive to said processor means for displaying pictures corresponding to the image data retrieved from said image knowledge base means in response to said text inquiry data.

77. A computerized aid to the cognitive process of pathology diagnosis comprising:
textual knowledge base means for storing text data including case information which is represented by multiple case records each of which is comprised of feature value data of clinical and histological features that characterize respective diseases;
image base means for storing image data representing images of disease states, including images of clinical and histological features which characterize those diseases, corresponding to the case records stored in the textual knowledge base means;
inquiry entry means for use by an operator to enter inquiry data designating clinical or histological features for selectively retrieving at least one case record from said textual knowledge base means and for retrieving from said image base means those images of clinical and histological features having the feature value data included in the retrieved case records;
processor means responsive to said inquiry data for retrieving feature, case or disease information from the textual knowledge base means and for retrieving image data from the image base means; and
picture display means responsive to said processor means for displaying pictures of those histological features corresponding to the image data retrieved from said image base means in response to the inquiry.

78. A method of utilizing a computerized aid to the cognitive process of diagnosis of the type having a knowledge base for storing textual data including case information representing multiple case records each comprised of data indicative of features which characterize that case and feature information represented by multiple feature values each comprised of data indicative of the components of which the feature which characterizes a case is formed, an image base for storing accessible image data representing features which are included in the stored case records, and a picture display for displaying pictures accessed from the image base, said method comprising the steps of:

entering text inquiry data designating features and feature values for selectively retrieving from said knowledge base data indicative of features and feature values and for retrieving from said image base image data representing designated features;

processing said text inquiry data to select those case records containing the designated features and image data representing said designated features;

selectively displaying textual information derived at least from said designated features; and displaying pictures of said designated features derived from the image data stored in said image base and included in a stored case record having the designated features.

* * * * *